US012704513B2

(12) United States Patent
Setliff et al.

(10) Patent No.: US 12,704,513 B2
(45) Date of Patent: Aug. 11, 2026

(54) SYSTEMS AND METHODS FOR SIMULTANEOUS DETECTION OF ANTIGENS AND ANTIGEN SPECIFIC ANTIBODIES

(71) Applicant: VANDERBILT UNIVERSITY, Nashville, TN (US)

(72) Inventors: Marion Francis Setliff, Nashville, TN (US); Ivelin Stefanov Georgiev, Brentwood, TN (US); Andrea Shiakolas, Nashville, TN (US)

(73) Assignee: VANDERBILT UNIVERSITY

( * ) Notice: Subject to any disclaimer, the term of this patent is extended or adjusted under 35 U.S.C. 154(b) by 705 days.

(21) Appl. No.: 17/266,169

(22) PCT Filed: Jul. 26, 2019

(86) PCT No.: PCT/US2019/043570

§ 371 (c)(1),
(2) Date: Feb. 5, 2021

(87) PCT Pub. No.: WO2020/033164

PCT Pub. Date: Feb. 13, 2020

(65) Prior Publication Data

US 2021/0302422 A1 Sep. 30, 2021

Related U.S. Application Data

(60) Provisional application No. 62/854,437, filed on May 30, 2019, provisional application No. 62/818,864, filed on Mar. 15, 2019, provisional application No. 62/716,013, filed on Aug. 8, 2018.

(51) Int. Cl.
*G01N 33/566* (2006.01)

(52) U.S. Cl.
CPC ....... *G01N 33/566* (2013.01); *G01N 2458/10* (2013.01)

(58) Field of Classification Search
CPC ......................... G01N 33/566; G01N 2458/10
See application file for complete search history.

(56) References Cited

U.S. PATENT DOCUMENTS

| | | | |
|---|---|---|---|
| 4,342,566 A | 8/1982 | Theofilopoulos et al. | |
| 5,079,155 A | 1/1992 | Cox et al. | |
| 5,084,169 A | 1/1992 | Noble et al. | |
| 5,804,440 A | 9/1998 | Burton et al. | |
| 6,096,441 A | 8/2000 | Barbas et al. | |
| 8,110,351 B2 | 2/2012 | Bosnes | |
| 9,689,024 B2 | 6/2017 | Hindson et al. | |
| 2011/0061874 A1 | 3/2011 | Stamoulis | |
| 2018/0073014 A1 | 3/2018 | Emig et al. | |
| 2018/0127743 A1* | 5/2018 | Vigneault | C12N 15/1062 |
| 2018/0208975 A1* | 7/2018 | Peterson | C12Q 1/6876 |
| 2022/0315982 A1* | 10/2022 | Setliff | C12Q 1/6804 |

FOREIGN PATENT DOCUMENTS

| | | | |
|---|---|---|---|
| WO | 94/29348 | 12/1994 | |
| WO | 2014144495 | 9/2014 | |
| WO | 2017/053902 | 3/2017 | |
| WO | WO-2017053902 A1 * | 3/2017 | A61P 35/00 |

OTHER PUBLICATIONS

Chen, Bing, and James J Chou. "Structure of the transmembrane domain of HIV-1 envelope glycoprotein." The FEBS journal vol. 284,8 (2017): 1171-1177. doi:10.1111/febs.13954 (Year: 2017).*

Kumar, P., Bartoszek, A.E., Moran, T.M., Gorski, J., Bhattacharyya, S., Navidad, J.F., Thakar, M.S., Malarkannan, S. High-throughput Detection Method for Influenza Virus. J. Vis. Exp. (60), e3623, DOI : 10.3791/3623 (2012) (Year: 2012).*

McLellan, Jason S et al. "Structure and function of respiratory syncytial virus surface glycoproteins." Current topics in microbiology and immunology vol. 372 (2013): 83-104. doi:10.1007/978-3-642-38919-1_4 (Year: 2013).*

Lee, C G et al. "Respiratory syncytial virus stimulation of vascular endothelial cell growth Factor/Vascular permeability factor." American journal of respiratory cell and molecular biology vol. 23,5 (2000): 662-9. doi:10.1165/ajrcmb.23.5.4188 (Year: 2000).*

Lynch, Rebecca M et al. "HIV-1 fitness cost associated with escape from the VRC01 class of CD4 binding site neutralizing antibodies." Journal of virology vol. 89,8 (2015): 4201-13. doi:10.1128/JVI.03608-14 (Year: 2015).*

Huang, Wen-Lin et al. "Prediction of linear B-cell epitopes of hepatitis C virus for vaccine development." BMC medical genomics vol. 8 Suppl 4,Suppl 4 (2015): S3. doi:10.1186/1755-8794-8-S4-S3 (Year: 2015).*

Gershoni, Jonathan M et al. "Epitope mapping: the first step in developing epitope-based vaccines." BioDrugs : clinical immunotherapeutics, biopharmaceuticals and gene therapy vol. 21,3 (2007): 145-56. doi:10.2165/00063030-200721030-00002 (Year: 2007).*

Wikipedia entry for "RNA Viruses". https://en.wikipedia.org/wiki/RNA_virus. Accessed on Oct. 18, 2023. (Year: 2023).*

Office Action received in connection with corresponding Application No. Canadian 3,108,770, dated Nov. 14, 2023, 4 pages.

Extended European Search Report received in EP 19848398.4 dated Mar. 28, 2022, 6 pages.

Adler, A.S., Mizrahi, R.A., Spindler, M.J., Adams, M.S., Asensio, M.A., Edgar, R.C., Leong, J., Leong, R., Roalfe, L., White, R., et al. (2017a). Rare, high-affinity anti-pathogen antibodies from human repertoires, discovered using microfluidics and molecular genomics. MAbs 9, 1282-1296.

Adler, A.S., Mizrahi, R.A., Spindler, M.J., Adams, M.S., Asensio, M.A., Edgar, R.C., Leong, J., Leong, R., and Johnson, D.S. (2017b). Rare, high-affinity mouse anti-PD-1 antibodies that function in checkpoint blockade, discovered using microfluidics and molecular genomics. MAbs 9, 1270-1281.

(Continued)

*Primary Examiner* — Gregory S Emch
*Assistant Examiner* — Mckenzie A Dunn
(74) *Attorney, Agent, or Firm* — Meunier Carlin & Curfman LLC

(57) ABSTRACT

The present disclosure relates to a system for simultaneous detection of antigens and antigen specific antibodies, and methods of use thereof.

15 Claims, 21 Drawing Sheets

Specification includes a Sequence Listing.

(56) References Cited

OTHER PUBLICATIONS

Alamyar, Eltaf, et al. "IMGT/HighV-QUEST: the IMGT® web portal for immunoglobulin (IG) or antibody and T cell receptor (TR) analysis from NGS high throughput and deep sequencing." Immunome res 8.1 (2012): 26.
Bönisch, Maximilian, et al. "Novel CH1: CL interfaces that enhance correct light chain pairing in heterodimeric bispecific antibodies." Protein Engineering, Design and Selection 30.9 (2017): 685-696.
Bonsignori, Mattia, et al. "Inference of the HIV-1 VRC01 antibody lineage unmutated common ancestor reveals alternative pathways to overcome a key glycan barrier." Immunity 49.6 (2018): 1162-1174.
Brekke, Ole Henrik, and Inger Sandlie. "Therapeutic antibodies for human diseases at the dawn of the twenty-first century." Nature reviews Drug discovery 2.1 (2003): 52-62.
Briggs, Adrian W., et al. "Tumor-infiltrating immune repertoires captured by single-cell barcoding in emulsion." BioRxiv (2017): 134841.
Briney, Bryan, et al. "Commonality despite exceptional diversity in the baseline human antibody repertoire." Nature 566.7744 (2019): 393-397.
Buchacher, A., et al. "Generation of human monoclonal antibodies against HIV-1 proteins; electrofusion and Epstein-Barr virus transformation for peripheral blood lymphocyte immortalization." AIDS research and human retroviruses 10.4 (1994): 359-369.
Busse, Christian E., et al. "Single-cell based high-throughput sequencing of full-length immunoglobulin heavy and light chain genes." European journal of immunology 44.2 (2014): 597-603.
Chen, Shifu, et al. "fastp: an ultra-fast all-in-one FASTQ reprocessor." Bioinformatics 34.17 (2018): i884-i890.
Crooke, Stanley T., et al. "Pharmacokinetic properties of several novel oligonucleotide analogs in mice." Journal of Pharmacology and Experimental Therapeutics 277.2 (1996): 923-937.
DeFalco, Jeff, et al. "Non-progressing cancer patients have persistent B cell responses expressing shared antibody paratopes that target public tumor antigens." Clinical Immunology 187 (2018): 37-45.
DeKosky, Brandon J., et al. "High-throughput sequencing of the paired human immunoglobulin heavy and light chain repertoire." Nature biotechnology 31.2 (2013): 166-169.
Dingens, Adam S., et al. "An antigenic atlas of HIV-1 escape from broadly neutralizing antibodies distinguishes functional and structural epitopes." Immunity 50.2 (2019): 520-532.
Do Kwon, Young, et al. "Crystal structure, conformational fixation and entry-related interactions of mature ligand-free HIV-1 Env." Nature structural & molecular biology 22.7 (2015): 522.
Eyer, Klaus, et al. "Single-cell deep phenotyping of IgG-secreting cells for high-resolution immune monitoring." Nature biotechnology 35.10 (2017): 977.
Georgiev, Ivelin S., et al. "Delineating antibody recognition in polyclonal sera from patterns of HIV-1 isolate neutralization." Science 340.6133 (2013): 751-756.
Georgiev, Ivelin S., et al. "Single-chain soluble BG505. SOSIP gp140 trimers as structural and antigenic mimics of mature closed HIV-1 Env." Journal of virology 89.10 (2015): 5318-5329.
Georgiou, George, et al. "The promise and challenge of high-throughput sequencing of the antibody repertoire." Nature biotechnology 32.2 (2014): 158-168.
Gierahn, T. M., et al. "Seq-Well: Portable, low-cost rna sequencing of single cells at high throughput". (2017). Nature Methods. https://doi.org/10.1038/nmeth.4179.
Guindon, Stéphane, et al. "Estimating maximum likelihood phylogenies with PhyML." Bioinformatics for DNA sequence analysis. Humana Press, 2009. 113-137.
Gupta, Namita T., et al. "Change-O: a toolkit for analyzing large-scale B cell immunoglobulin repertoire sequencing data." Bioinformatics 31.20 (2015): 3356-3358.
Huang, Jinghe, et al. "Broad and potent neutralization of HIV-1 by a gp41-specific human antibody." Nature 491.7424 (2012): 406-412.
Kabanov, Alexander V., et al. "A new class of antivirals: antisense oligonucleotides combined with a hydrophobic substituent effectively inhibit influenza virus reproduction and synthesis of virus-specific proteins in MDCK cells." FEBS letters 259.2 (1990): 327-330.
Köhler, Georges, and Cesar Milstein. "Continuous cultures of fused cells secreting antibody of predefined specificity." nature 256.5517 (1975): 495-497.
Köster, Sarah, et al. "Drop-based microfluidic devices for encapsulation of single cells." Lab on a Chip 8.7 (2008): 1110-1115.
Kotecha, Nikesh, Peter O. Krutzik, and Jonathan M. Irish. "Web-based analysis and publication of flow cytometry experiments." Current protocols in cytometry 53.1 (2010): 10-17.
Lee, Jeong Hyun, et al. "A broadly neutralizing antibody targets the dynamic HIV envelope trimer apex via a long, rigidified, and anionic β-hairpin structure." Immunity 46.4 (2017): 690-702.
Letsinger, Robert L., et al. "Cholesteryl-conjugated oligonucleotides: synthesis, properties, and activity as inhibitors of replication of human immunodeficiency virus in cell culture." Proceedings of the National Academy of Sciences 86.17 (1989): 6553-6556.
Manoharan et al., "Chemical Modifications to Improve Uptake and Bioavailability of Antisense Oligonucleotides", Ann. NY Acad. Sciences, 1992, 660, 306-309.
Manoharan, Muthiah, et al. "Cholic acid-oligonucleotide conjugates for antisense applications." Bioorganic & Medicinal Chemistry Letters 4.8 (1994): 1053-1060.
Manoharan, Muthiah, et al. "Introduction of a lipophilic thioether tether in the minor groove of nucleic acids for antisense applications." Bioorganic & Medicinal Chemistry Letters 3.12 (1993): 2765-2770.
Manoharan, Muthiah, et al. "Oligonucleotide conjugates: alteration of the pharmacokinetic properties of antisense agents." Nucleosides, Nucleotides & Nucleic Acids 14.3-5 (1995): 969-973.
Manoharan, Muthiah, Kathleen L. Tivel, and P. Dan Cook. "Lipidic nucleic acids." Tetrahedron Letters 36.21 (1995): 3651-3654.
Mason, Derek M., et al. "High-throughput antibody engineering in mammalian cells by CRISPR/Cas9-mediated homology-directed mutagenesis." Nucleic acids research 46.14 (2018): 7436-7449.
Mazutis, Linas, et al. "Single-cell analysis and sorting using droplet-based microfluidics." Nature protocols 8.5 (2013): 870-891.
Mimitou, Eleni P., et al. "Multiplexed detection of proteins, transcriptomes, clonotypes and CRISPR perturbations in single cells." Nature methods 16.5 (2019): 409-412.
Mishra, Rakesh Kumar, et al. "Improved leishmanicidal effect of phosphorotioate antisense oligonucleotides by LDL-mediated delivery." Biochimica et Biophysica Acta (BBA)-Gene Structure and Expression 1264.2 (1995): 229-237.
Oberhauser, Berndt, and Ernst Wagner. "Effective incorporation of 2'-O-methyl-oligoribonuclectides into liposomes and enhanced cell association through modification with thiocholesterol." Nucleic Acids Research 20.3 (1992): 533-538.
Pedregosa, Fabian, et al. "Scikit-learn: Machine learning in Python." the Journal of machine Learning research 12 (2011): 2825-2830.
Percival-Alwyn, Jennifer L., et al. "Generation of potent mouse monoclonal antibodies to self-proteins using T-cell epitope "tags"." MAbs. vol. 7. No. 1. Taylor & Francis, 2015.
Peterson, Vanessa M., et al. "Multiplexed quantification of proteins and transcripts in single cells." Nature biotechnology 35.10 (2017): 936-939.
Ponsel, Dirk, et al. "High affinity, developability and functional size: the holy grail of combinatorial antibody library generation." Molecules 16.5 (2011): 3675-3700.
Rajewsky, Klaus. "Clonal selection and learning in the antibody system." Nature 381.6585 (1996): 751-758.
Ringe, Rajesh P., et al. "Improving the expression and purification of soluble, recombinant native-like HIV-1 envelope glycoprotein trimers by targeted sequence changes." Journal of virology 91.12 (2017).
Saison-Behmoaras, T., et al. "Short modified antisense oligonucleotides directed against Ha-ras point mutation induce selective cleavage of the mRNA and inhibit T24 cells proliferation." The EMBO journal 10.5 (1991): 1111-1118.

(56) References Cited

OTHER PUBLICATIONS

Sanders, Rogier W., et al. "A next-generation cleaved, soluble HIV-1 Env trimer, BG505 SOSIP. 664 gp140, expresses multiple epitopes for broadly neutralizing but not non-neutralizing antibodies." PLoS pathog 9.9 (2013): e1003618.
Sarzotti-Kelsoe, Marcella, et al. "Optimization and validation of the TZM-bl assay for standardized assessments of neutralizing antibodies against HIV-1." Journal of immunological methods vol. 409 (2014): 131-46. doi:10.1016/j.jim.2013.11.022.
Scheid, Johannes F., et al. "A method for identification of HIV gp140 binding memory B cells in human blood." Journal of immunological methods 343.2 (2009): 65-67.
Scheid, Johannes F., et al. "Broad diversity of neutralizing antibodies isolated from memory B cells in HIV-infected individuals." Nature 458.7238 (2009): 636-640.
Setliff, Ian, et al. "Multi-donor longitudinal antibody repertoire sequencing reveals the existence of public antibody clonotypes in HIV-1 infection." Cell host & microbe 23.6 (2018): 845-854.
Shea, Regan G., James C. Marsters, and Norbert Bischofberger. "Synthesis, hybridization properties and antiviral activity of lipid-oligodeoxynucleotide conjugates." Nucleic acids research 18.13 (1990): 3777-3783.
Shembekar, Nachiket, et al. "Single-cell droplet microfluidic screening for antibodies specifically binding to target cells." Cell reports 22.8 (2018): 2206-2215.
Soto, Cinque, et al. "High frequency of shared clonotypes in human B cell receptor repertoires." Nature 566.7744 (2019): 398-402.
Stiegler, Gabriela, et al. "A potent cross-clade neutralizing human monoclonal antibody against a novel epitope on gp41 of human immunodeficiency virus type 1." AIDS research and human retroviruses 17.18 (2001): 1757-1765.
Stoeckius, Marlon, et al. "Simultaneous epitope and transcriptome measurement in single cells." Nature methods 14.9 (2017): 865-868.
Svinarchuk, F. P., et al. "Inhibition of HIV proliferation in MT-4 cells by antisense oligonucleotide conjugated to lipophilic groups." Biochimie 75.1-2 (1993): 49-54.
Tan, Yann-Chong, et al. "Barcode-enabled sequencing of plasmablast antibody repertoires in rheumatoid arthritis." Arthritis & rheumatology 66.10 (2014): 2706-2715.
Tiller, Thomas, et al. "Efficient generation of monoclonal antibodies from single human B cells by single cell RT-PCR and expression vector cloning." Journal of immunological methods 329.1-2 (2008): 112-124.
TriLink cat No. S-9011, Aug. 31, 2018, 2 pages.
Walker, Laura M., et al. "Broad and potent neutralizing antibodies from an African donor reveal a new HIV-1 vaccine target." Science 326.5950 (2009): 285-289.
Walker, Laura M., et al. "Broad neutralization coverage of HIV by multiple highly potent antibodies." Nature 477.7365 (2011): 466-470.
Wang, Bo, et al. "Functional interrogation and mining of natively paired human V H: V L antibody repertoires." Nature biotechnology 36.2 (2018): 152-155.
Weaver, Grant C., et al. "In vitro reconstitution of B cell receptor-antigen interactions to evaluate potential vaccine candidates." Nature protocols 11.2 (2016): 193.
Whittle, James RR, et al. "Flow cytometry reveals that H5N1 vaccination elicits cross-reactive stem-directed antibodies from multiple Ig heavy-chain lineages." Journal of virology 88.8 (2014): 4047-4057.
Wilson, Patrick C., and Sarah F. Andrews. "Tools to therapeutically harness the human antibody response." Nature Reviews Immunology 12.10 (2012): 709-719.
Wu, Xueling, et al. "Maturation and diversity of the VRC01-antibody lineage over 15 years of chronic HIV-1 infection." Cell 161.3 (2015): 470-485.
Wu, Xueling, et al. "Rational design of envelope identifies broadly neutralizing human monoclonal antibodies to HIV-1." Science 329.5993 (2010): 856-861.
Xu, George J., et al. "Comprehensive serological profiling of human populations using a synthetic human virome." Science 348. 6239:aaa0698 (2015).
Ye, Jian, et al. "IgBLAST: an immunoglobulin variable domain sequence analysis tool." Nucleic acids research 41.W1 (2013): W34-W40.
Zoller, Mark J. "New recombinant DNA methodology for protein engineering." Current opinion in biotechnology 3.4 (1992): 348-354.
International Search Report and Written Opinion dated Oct. 16, 2019, from International Application No. PCT/US2019/043570, 13 pages.

* cited by examiner

G

| CDRH3 | CDRL3 |
|---|---|
| AMRDYCRDDNCNKWDLRH | QHRET |
| AMRDYCRDDNCNKWDLRH | QHRET |
| AMRDYCRDDNCNRWDLRH | QHRET |
| AMRDYCRDDNCNRWDLRH | QHRET |
| AMRDYCRDDSCNIWDLRH | QHRET |
| AMRDYCRDDNCNIWDLRH | QHRET |
| VRTAYCERDPCKGWVFPH | QFLEN |
| VRTAYCERDPCKGWVFPH | QFLEN |
| VRRGHCDHCYEWTLQH | QDRQS |
| VRRGHCDHCYEWTLQH | QDRQS |
| VRRGHCDHCYEWTLQH | QDRQS |
| VRRGSCDYCGDFPWQY | QQFEF |
| VRRGSCGYCGDFPWQY | QQFEF |
| VRRGSCGYCGDFPWQY | QQFEF |
| VRGSSCCGGRRHCNGADCFNWDFQY | QCLEA |
| VRGRSCCGGRRHCNGADCFNWDFQY | QCLEA |
| VRGKSCCGGRRYCNGADCFNWDFEH | QSFEG |
| VRGKSCCGGRRYCNGADCFNWDFEH | QSFEG |
| VRGKSCCHGRRYCNGADCFNWDFEH | QCMEG |
| VRGKSCCHGRRYCNGADCFNWDFEH | QCMEG |
| VRGKSCCHGRRYCNGADCFNWDFEH | QCMEG |
| VRGRSCCDGRRYCNGADCFNWDFEH | QCFEG |
| TRGKYCTARDYYNWDFEH | QQYEF |
| TRGKYCTARDYYNWDFEH | QQYEF |
| TRGKYCTARDYYNWDFEH | QQYEF |
| TRGKYCTARDYYNWDFEH | QQYEF |
| TRGKYCTARDYYNWDFEH | QQYEF |
| TRGKYCTARDYYNWDFEY | QQYEF |
| TRGKNCDDNWDFEH | QQYEF |
| TRGKNCNYNWDFEH | QQYEF |

| Name | VH Gene | VH % Identity | CDRH3 Length | VDJ Junction | VL Gene | VL % Identity | CDRL3 Length | VJ Junction | Specificity (ELISA) |
|---|---|---|---|---|---|---|---|---|---|
| 2723-2121 | IGHV4-39 | 86.55 | 21 | ARHRADYDFWNGNNLRGYFDP | IGKV3-20 | 94.33 | 9 | QQYGSSPTT | HIV |
| 2723-2304 | IGHV4-39 | 85.22 | 21 | ARHRADYDFWGGSNLRGYFDP | IGKV3-20 | 90.07 | 9 | QQYGTSPTT | HIV |
| 2723-422 | IGHV4-39 | 85.91 | 21 | ARHRANYDFWGGSNLRGYFDP | IGKV3-20 | 88.65 | 9 | QQYGTSPTT | HIV |
| 2723-2859 | IGHV1-69 | 90.97 | 15 | VTMSGYHVSNTYLDA | IGKV3-20 | 94.68 | 9 | QQYANSPLT | Flu |
| 2723-3415 | IGHV1-18 | 91.32 | 9 | ARGRVYSDY | IGKV3-20 | 95.74 | 10 | QQSGTSPPWT | Flu |

I

A

C

| Virus Phenotype | Env-Pseudoviruses | $IC_{50}$ (mg/ml) | |
|---|---|---|---|
| | | 2723-2121 | VRC01 |
| Tier 1 | MW965_26 | 0.067 | 0.025 |
| | MN_3 | <0.020 | 0.044 |
| | 6644_V2_C33 | 2.441 | 0.139 |
| Tier 2 (Sorting antigens) | BG505_W6M_C2 | >50 | 0.035 |
| | BG505_W6M_C2_T332N | >50 | 0.060 |
| | ZA097 | >50 | 0.090 |
| Tier 2 (Global Panel) | TR0_11 | >50 | 0.226 |
| | CH119_10 | >50 | 0.710 |
| | CNE55 | >50 | 0.156 |
| | 25710_2_43 | 21.568 | 0.470 |
| | CE0217 | >50 | 0.136 |
| | X1632_S2_B10 | >50 | 0.150 |
| | X2278_C2_B6 | >50 | 0.091 |
| | 246_F3_C10_2 | >50 | 0.321 |
| | 398_F1_F6_20 | 1.760 | 0.130 |
| | CE1176_A3 | >50 | 1.170 |
| | BJOX002000_03_2 | >50 | >50 |
| Control | MLV | >50 | >50 |

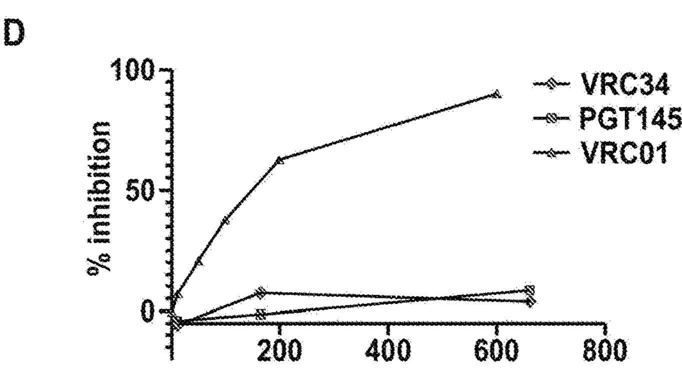

Ramos B Cell Lines

| Summary | |
|---|---|
| Sequencing | paired end (150 cycles + 150 cycles) |
| Mean length before filtering | 150 bp, 150 bp |
| Mean length after filtering | 53 bp, 53 bp |
| Insert size peak | 52 bp |

| Before filtering | |
|---|---|
| Total reads | 46.683278 M |
| Total bases | 7.002492 G |
| Q20 bases | 5.890977 G (84.126864%) |
| Q30 bases | 5.343662 G (76.310871%) |

| After filtering | |
|---|---|
| Total reads | 46.317712 M |
| Total bases | 2.473195 G |
| Q20 bases | 2.438363 G (98.591592%) |
| Q30 bases | 2.358131 G (95.347568%) |

| Filtering results | |
|---|---|
| Reads passed filters | 46.317712 M |
| Reads with low quality | 253.286000 K (0.542563%) |
| Reads with too many N | 94 (0.000201%) |
| Reads too short | 112.186000 K (0.240313%) |

FIG. 6

Donor NIH45

Summary

| | |
|---|---|
| Sequencing | paired end (150 cycles + 150 cycles) |
| Mean length before filtering | 149 bp, 149 bp |
| Mean length after filtering | 55 bp, 55 bp |
| Insert size peak | 52 bp |

Before filtering

| | |
|---|---|
| Total reads | 39.610554 M |
| Total bases | 5.940879 G |
| Q20 bases | 4.959718 G (83.484582%) |
| Q30 bases | 4.463982 G (75.140098%) |

After filtering

| | |
|---|---|
| Total reads | 36.922686 M |
| Total bases | 2.061362 G |
| Q20 bases | 1.992712 G (96.669638%) |
| Q30 bases | 1.910089 G (92.661463%) |

Filtering results

| | |
|---|---|
| Reads passed filters | 36.922686 M |
| Reads with low quality | 1.506144 K (3.802381%) |
| Reads with too many N | 158 (0.000399%) |
| Reads too short | 1.181566 M (2.982958%) |

Antigen screening library
- BG505sc Wild type
- BG505sc N160K
- BG505sc N169E
- BG505sc D368R
- (HA NC99)

SYSTEMS AND METHODS FOR SIMULTANEOUS DETECTION OF ANTIGENS AND ANTIGEN SPECIFIC ANTIBODIES

CROSS REFERENCE TO RELATED APPLICATIONS

This application is a National Phase Application of PCT/US2019/043570, filed Jul. 26, 2019, which claims the benefit of U.S. Provisional Patent Application Ser. No. 62/716,013 filed Aug. 8, 2018, U.S. Provisional Patent Application Ser. No. 62/818,864 filed Mar. 15, 2019, and U.S. Provisional Patent Application Ser. No. 62/854,437 filed May 30, 2019, the disclosures of which are expressly incorporated herein by reference.

STATEMENT REGARDING FEDERALLY SPONSORED RESEARCH

This invention was made with government support under Grant No. R01 AI131722 awarded by the National Institutes of Health. The government has certain rights in the invention.

FIELD

The present disclosure relates to systems and methods for simultaneous detection of antigens and antigen specific antibodies.

BACKGROUND

The human immune system participates in complex interactions with virtually all other systems in the body. In particular, the B-cell component of the adaptive immune response plays a role in various disease settings, including infectious disease, cancer, autoimmunity, cardiovascular, hematologic, and neurologic diseases. In addition, antibodies (a product of B cells) are effectively used in diagnostics and therapeutics. Despite decades of antibody discovery efforts, there is still limited public data linking human antibody sequence to antigen specificity. This is because the processes of obtaining antibody sequence and binding information are typically decoupled and low throughput. While next-generation sequencing (NGS) of B-cell receptor (BCR) transcripts enables high-throughput interrogation of the BCR sequence repertoire, uniting these BCR sequence with cognate antigen specificity requires production and characterization of sequences of interest one at a time.

To date, the process of isolating potent neutralizing antibodies from human samples or immunized animal models has been driven by a variety of methods like single-cell sorting, screens of immortalized B cells or hybridomas, and B cell culture. However, initial screening of cell supernatants is low-throughput and typically restricted to few antigens, which limits the number of antibodies that can be characterized and the ability to detect cross-reactivity. An alternative to screening supernatants of cultured or immortalized B cells is to screen surface-expressed BCRs via antigen-specific B cell sorting. In antigen-specific B cell sorting, an antigen is conjugated to a fluorophore and used to stain a B cell population of interest. This allows identification of rare clones, but the subsequent determination of BCR sequences requires cloning $V_H$ and $V_\kappa/V_\lambda$ genes and Sanger sequencing for each individual B cell. Notably, none of these traditional methods are conducive to recovering antibody sequence and function simultaneously.

An alternative to in vivo methods is to utilize in vitro display technologies, such as phage, yeast, ribosome, mammalian or other display of single-chain variable fragments (scFV), antigen-binding fragments (Fab), other antibody fragments, or, in some cases, full-length IgG. These display technologies often suffer from high immunogenicity, inferior biophysical properties, and lack of desired antibody function. What is needed are novel systems and methods for rapidly screening antibody-secreting or antibody-expressing cells in a parallel manner against a panel of candidate antibody binding partners.

SUMMARY

Disclosed herein are systems and methods for simultaneous detection of antigens and antigen specific antibodies. In some aspects, disclosed herein is a system for simultaneous detection of an antigen and an antibody that specifically binds said antigen, comprising: a plurality of barcode-labeled antigens; a population of B-cells; and a pool of cell barcode-labeled beads.

In some embodiments, the barcode-labeled antigens are labeled with a first barcode comprising a DNA sequence or an RNA sequence. In some embodiments, the cell barcode-labeled beads are labeled with a second barcode comprising a DNA sequence or an RNA sequence.

In some embodiments, the barcode-labeled antigens comprise an antigen from a pathogen or an animal. In some embodiments, the antigen from a pathogen comprises an antigen from a virus. In some embodiments, the antigen from a virus comprises an antigen from human immunodeficiency virus (HIV), an antigen from influenza virus, or an antigen from respiratory syncytial virus (RSV). In some embodiments, the antigen from HIV comprises HIV-1 Env. In some embodiments, the antigen from influenza virus comprises hemagglutinin (HA). In some embodiments, the antigen from RSV comprises an RSV F protein.

In some embodiments, the antigen from an animal comprises an antigen from a human.

In some embodiments, the population of B-cells comprise a memory B-cell, a plasma cell, a naïve B cell, an activated B-cell, or a B-cell line. In some embodiments, the B-cell line comprises VRC01, PGT128, PGT145, VRC34, 10E8, 447-52D, Fe53, or CH65.

In another aspect, disclosed herein is a method for simultaneous detection of an antigen and an antigen specific antibody, comprising:

- labeling a plurality of antigens with unique antigen barcodes;
- providing a plurality of barcode-labeled antigens to a population of B-cells;
- allowing the plurality of barcode-labeled antigens to bind to the population of B-cells; washing unbound antigens from the population of B-cells;
- separating the B-cells into single cell emulsions;
- introducing into each single cell emulsion a unique cell barcode-labeled bead; preparing a single cell cDNA library from the single cell emulsions;
- performing PCR amplification reactions to produce a plurality of amplicons, wherein the amplicons comprise: 1) the cell barcode and the antigen barcode, and 2) the cell barcode and i) an immunoglobulin heavy chain (VDJ) sequence, or ii) an immunoglobulin light chain (VJ) sequence; and
- sequencing the plurality of amplicons.

Also disclosed herein is a set of PCR primers for performing PCR amplification reactions to produce a plurality of amplicons, wherein the amplicons comprise: 1) the cell barcode and the antigen barcode, and 2) the cell barcode and i) an immunoglobulin heavy chain (VDJ) sequence, or ii) an immunoglobulin light chain (VJ) sequence.

DESCRIPTION OF DRAWINGS

The accompanying figures, which are incorporated in and constitute a part of this specification, illustrate aspects described below.

Figure 2:
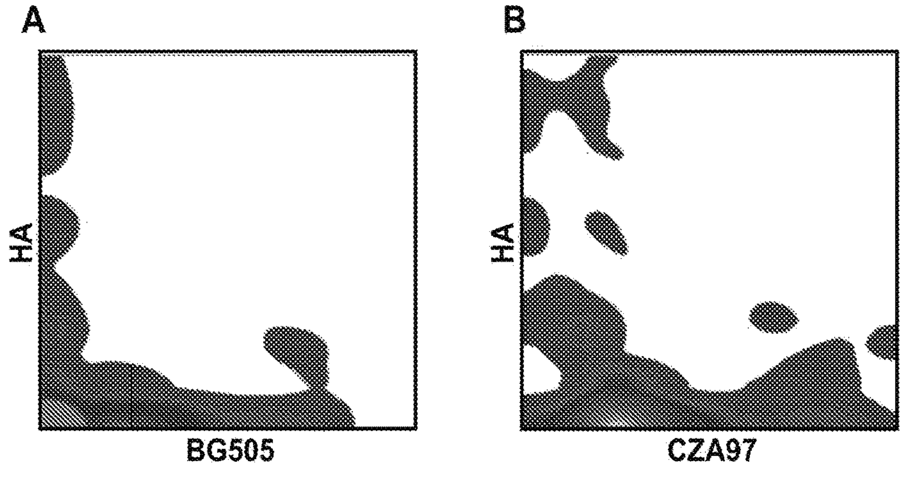
FIG. 2. LIBRA-seq applied to a human B cell sample from HIV-infected donor NIAID 45. (A-C) After bioinformatic processing and filtering of cells recovered from single-cell sequencing, the LIBRA-seq score for each antigen was plotted for each cell possessing high-confidence antigen mapping and a functional heavy and light chain (total=848). Each axis represents the minimum to maximum LIBRA-seq score for each antigen. Density of total cells is shown, with purple to yellow indicating lowest to highest number of cells, respectively. LIBRA-seq scores for (A.) HA (x-axis) and BG505 (y-axis), (B.) HA (x-axis) and CZA97 (y-axis), and (C.) BG505 (x-axis) and CZA97 (y-axis) are shown. (D-G) 30 linked VRC01 lineage B cells were identified and examined for phylogenetic relatedness to known lineage members as well as for sequence features. (D.) Phylogenetic tree showing relatedness of previously identified VRC01 lineage members (black) and members newly identified using LIBRA-seq (red). Each row represents an antibody. Sequences were aligned using clustal W and a maximum likelihood tree was inferred using maximum likelihood inference. The resulting tree was visualized using an inferred VRC01 unmutated common ancestor (UCA) (accession MK032222) as the root. (E.) For each antibody isolated from LIBRA-seq, a heat map of the LIBRA-seq scores for each antigen (BG505, CZA97, and HA) is shown. Light to dark blue represents low (minimum=0) to high (maximum=1) scores, respectively. (F.) Levels of somatic hypermutation (SHM) at the nucleotide level for the heavy and light chain variable genes as reported by IMGT are displayed as bars, with the numerical percentage value listed to the right of the bar length of the bar corresponds to level of SHM. (G.) Amino acid sequences of the complementarity determining region 3 for the heavy chain (CDRH3) and the light chain (CDRL3) for each antibody. (H-J) Antigen specificity as predicted by LIBRA-seq was validated for a subset of monoclonal antibodies not belonging to the VRC01 lineage. (H.) Genetic characterization and antigen specificity as determined by ELISA of newly identified antibodies from donor NIAID 45. Percent identity is calculated at the nucleotide level, and CDR length and sequences are noted at the amino acid level. (I.) LIBRA-seq scores for HA vs maximum Env (the maximum LIBRA-seq score between CZA97 and BG505). The 5 antibodies tested by ELISA are shown as dots in magenta (influenza-specific) and green (HIV-specific). (J.) ELISA binding data for HIV-specific antibodies 2723-2121, 2723-2304, and 2723-422 (top), and for influenza-specific antibodies 2723-3415 and 2723-2859 (bottom), against each of BG505, CZA97, and HA.
Figure 2:
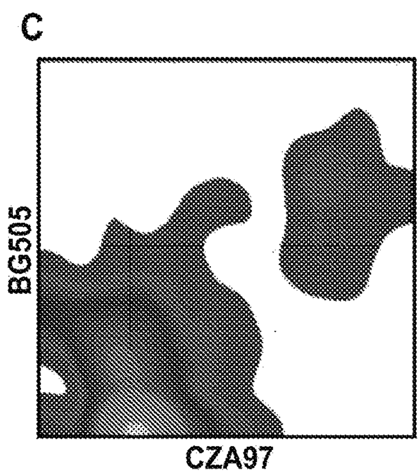
Figure 2:
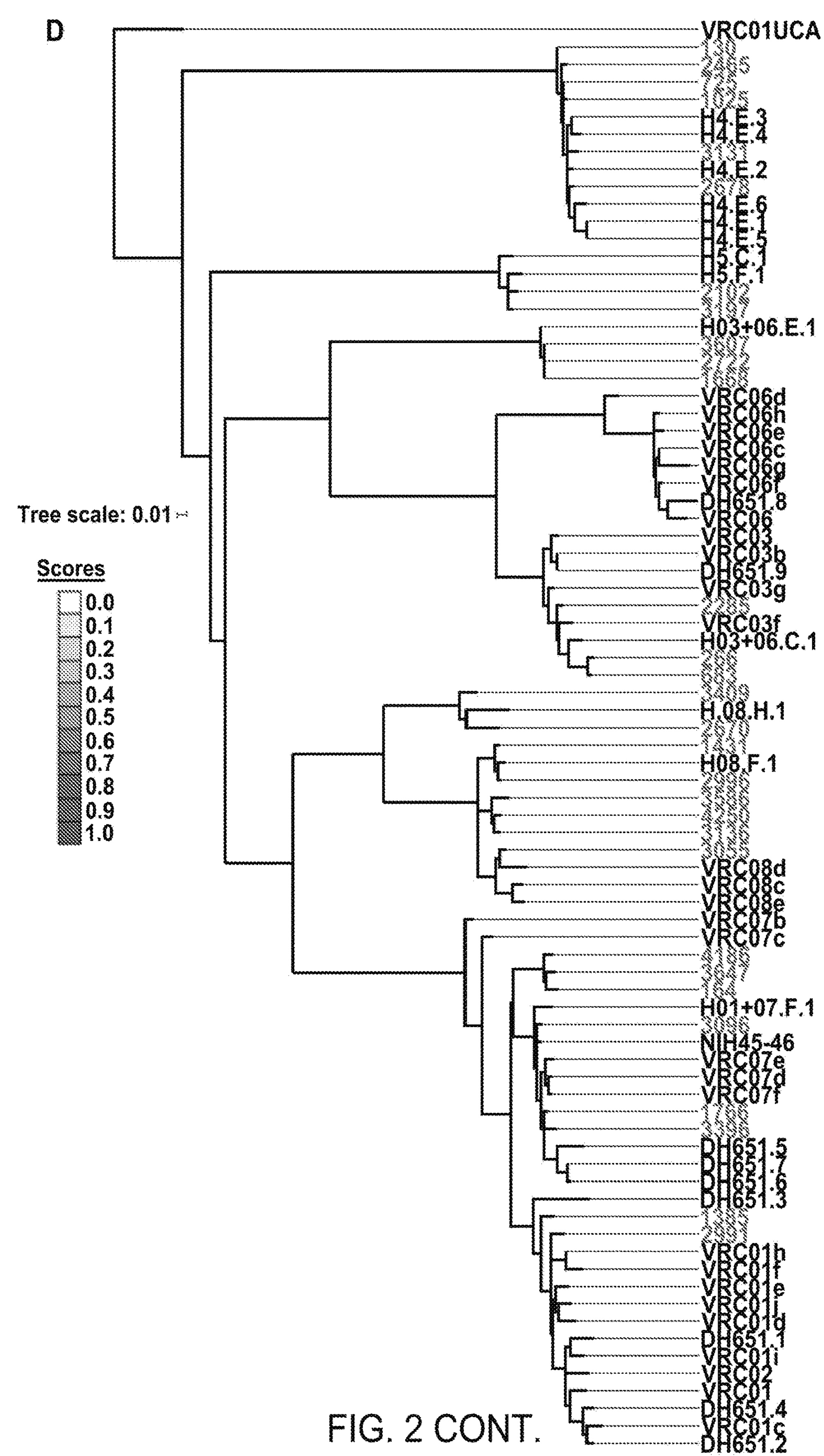
Figure 2:
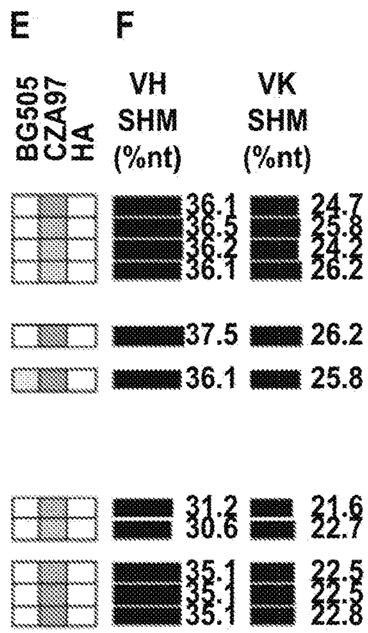
Figure 2:
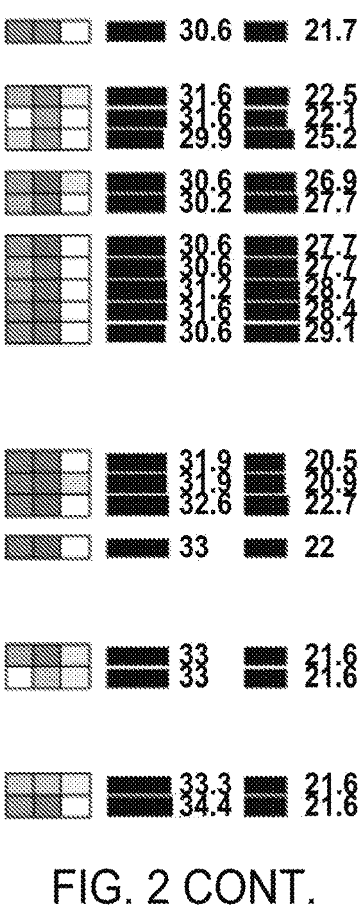
Figure 2:
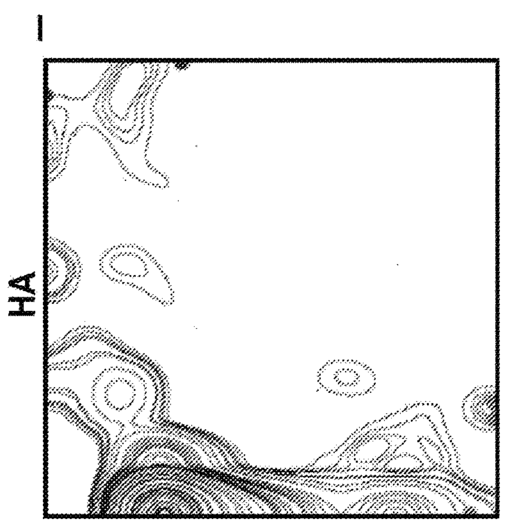
Figure 2:
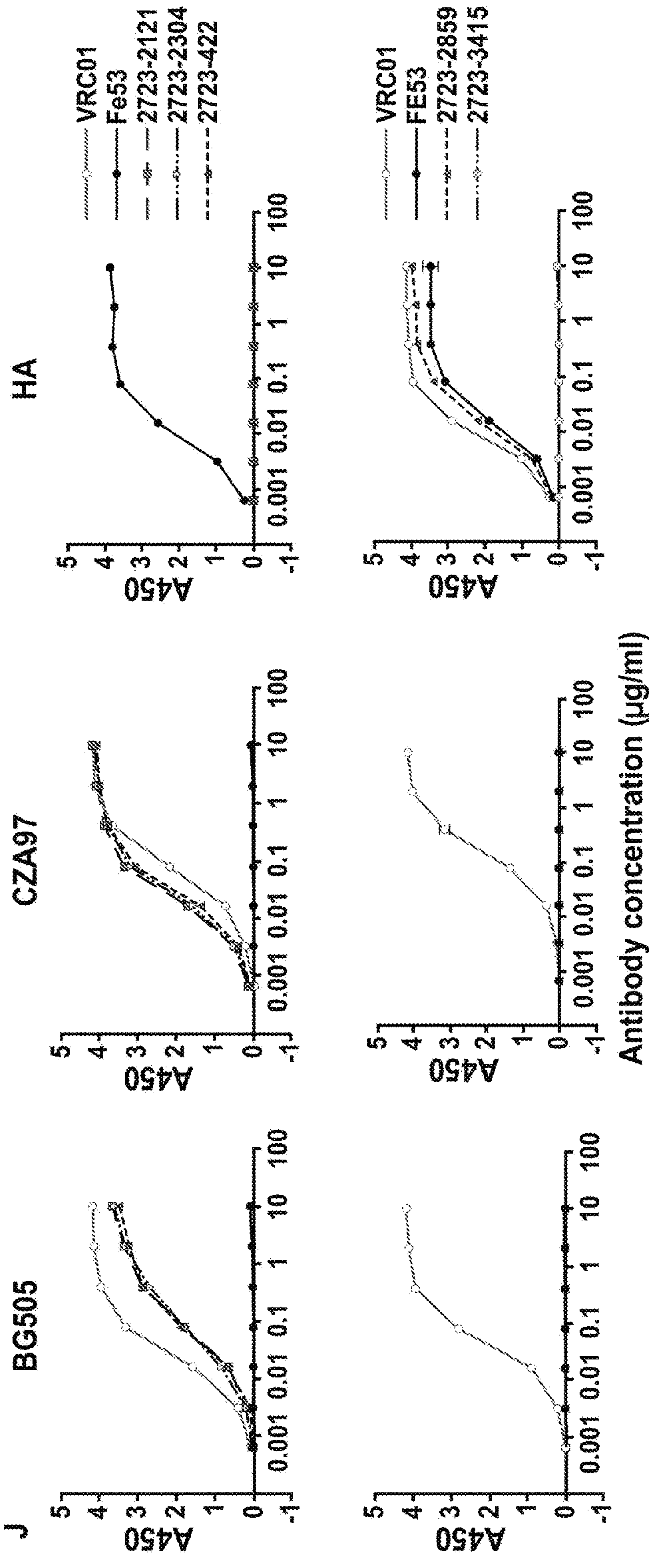

```
Sequences disclosed in FIG. 2G:
                                      (SEQ ID NO: 21)
AMRDYCRDDNCNKWDLRH;

                                      (SEQ ID NO: 51)
QHRET;

                                      (SEQ ID NO: 22)
AMRDYCRDDNCNRWDLRH;

                                      (SEQ ID NO: 52)
QHRET;

                                     (SEQ ID NO: 23)
AMRDYCRDDSCNIWDLRH;

                                      (SEQ ID NO: 53)
QHRET;

                                     (SEQ ID NO: 24)
AMRDYCRDDNCNIWDLRH;

                                      (SEQ ID NO: 54)
QHRET;

                                     (SEQ ID NO: 25)
VRTAYCERDPCKGWVFPH;

                                      (SEQ ID NO: 55)
QFLEN;

                                     (SEQ ID NO: 26)
VRRGHCDHCYEWTLQH;

                                      (SEQ ID NO: 56)
QDRQS;

                                     (SEQ ID NO: 27)
VRRGSCDYCGDFPWQY;

                                      (SEQ ID NO: 57)
QQFEF;

                                     (SEQ ID NO: 28)
VRRGSCGYCGDFPWQY;

                                      (SEQ ID NO: 58)
QQFEF;

                                     (SEQ ID NO: 29)
VRGSSCCGGRRHCNGADCFNWDFQY;
```

-continued (SEQ ID NO: 59)
QCLEA;

(SEQ ID NO: 30)
VRGRSCCGGRRHCNGADCFNWDFQY;

(SEQ ID NO: 60)
QCLEA;

(SEQ ID NO: 31)
VRGKSCCGGRRYCNGADCFNWDFEH;

(SEQ ID NO: 61)
QSFEG;

(SEQ ID NO: 32)
VRGKSCCHGRRYCNGADCFNWDFEH;

(SEQ ID NO: 62)
QCMEG;

(SEQ ID NO: 33)
VRGRSCCDGRRYCNGADCFNWDFEH;

(SEQ ID NO: 63)
QCFEG;

(SEQ ID NO: 34)
TRGKYCTARDYYNWDFEH;

(SEQ ID NO: 64)
QQYEF;

(SEQ ID NO: 35)
TRGKYCTARDYYNWDFEY;

(SEQ ID NO: 65)
QQYEF;

(SEQ ID NO: 36)
TRGKNCDDNWDFEH;

(SEQ ID NO: 66)
QQYEF;

(SEQ ID NO: 37)
TRGKNCNYNWDFEH;

(SEQ ID NO: 67)
QQYEF.

Sequences disclosed in FIG. 2H:

(SEQ ID NO: 38)
ARHRADYDFWNGNNLRGYFDP;

(SEQ ID NO: 68)
QQYGSSPTT;

(SEQ ID NO: 39)
ARHRADYDFWGGSNLRGYFDP;

(SEQ ID NO: 69)
QQYGTSPTT;

(SEQ ID NO: 40)
ARHRANYDFWGGSNLRGYFDP;

(SEQ ID NO: 70)
QQYGTSPTT;

(SEQ ID NO: 41)
VTMSGYHVSNTYLDA;

(SEQ ID NO: 71)
QQYANSPLT;

(SEQ ID NO: 42)
ARGRVYSDY (SEQ ID NO: 72)
QQSGTSPPWT.

Figure 3:
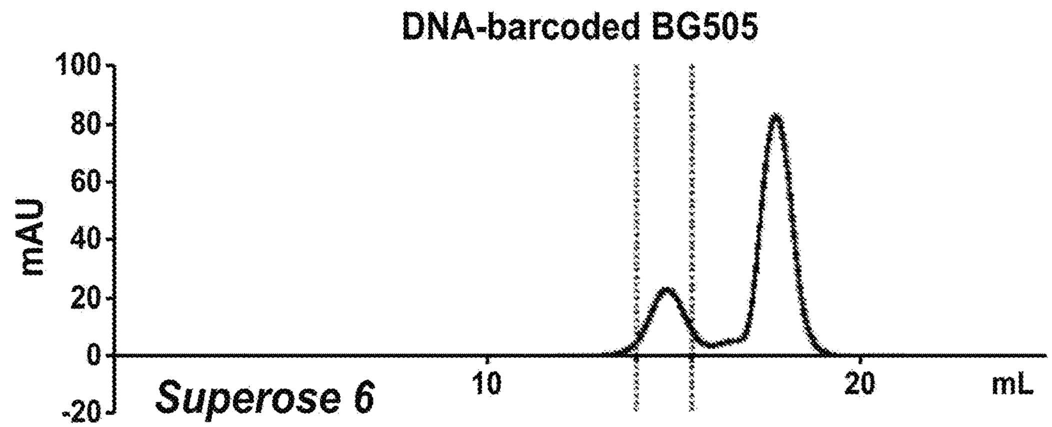
Figure 3:
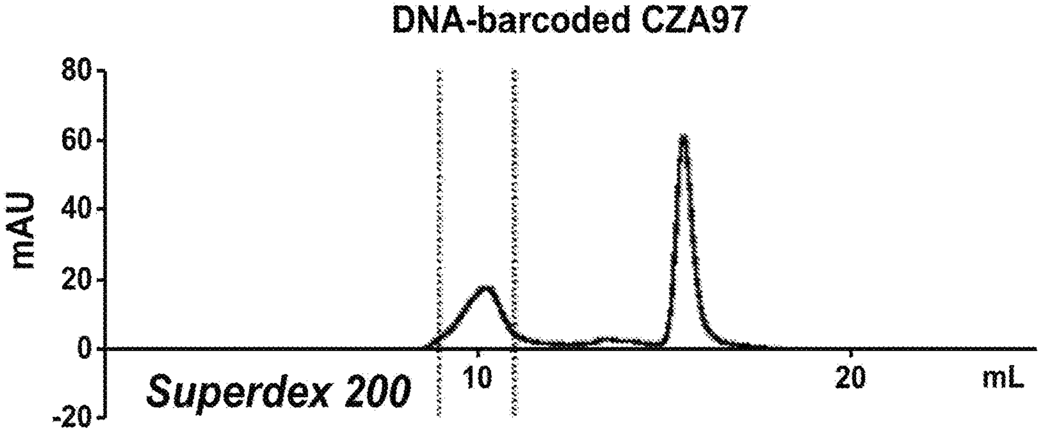
Figure 3:
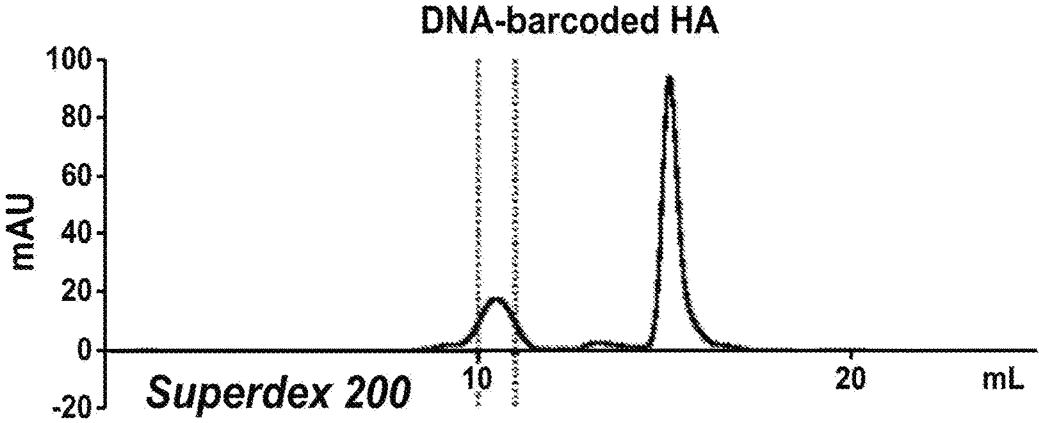
Figure 3:
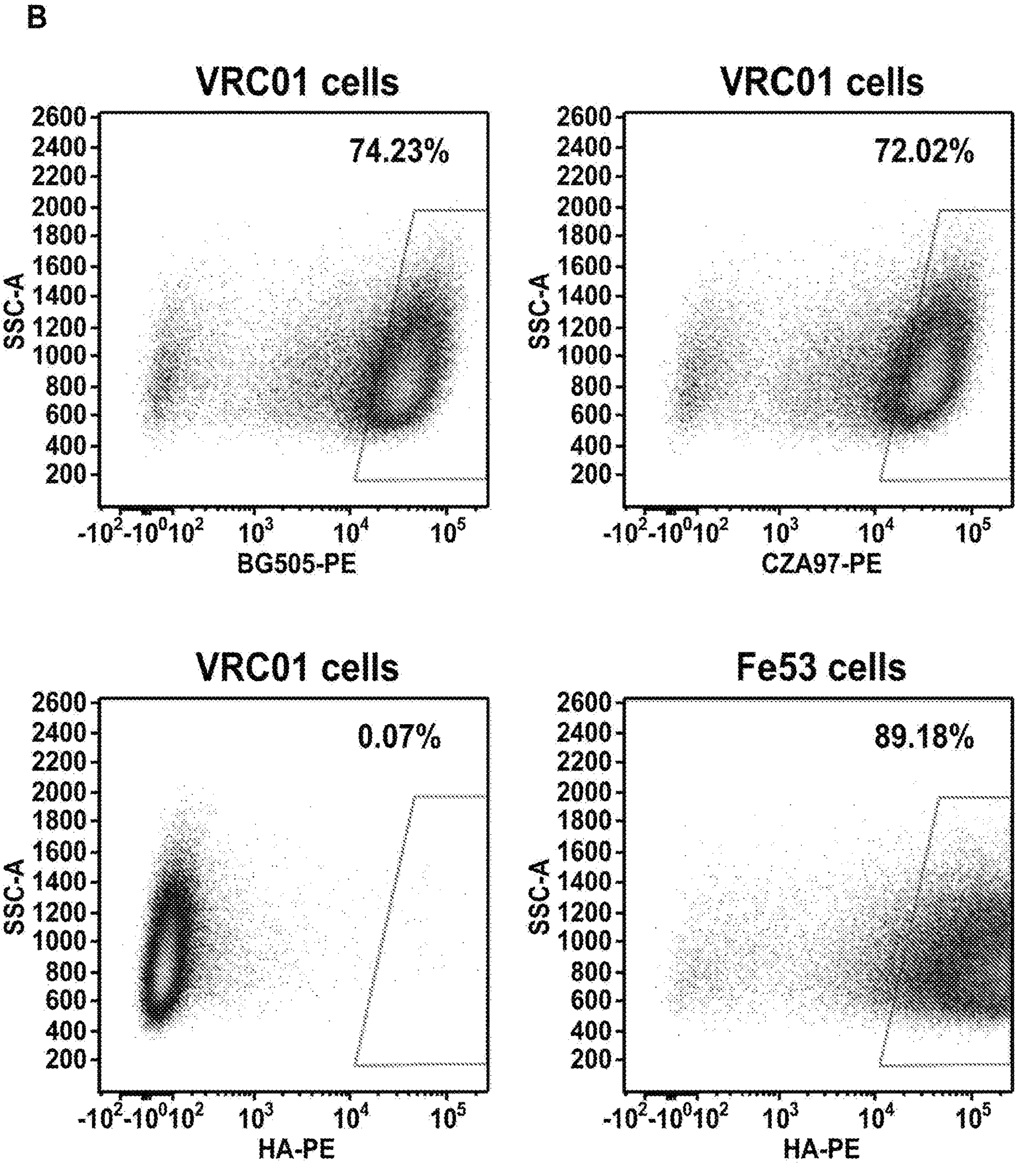

FIG. 3. Purification of DNA-barcoded antigens. (A.) After barcoding each antigen with a unique oligonucleotide, antigen-oligo complexes are run on size exclusion chromatography to remove excess, unconjugated oligonucleotide from the reaction mixture. DNA-barcoded BG505 was run on the Superose 6 Increase 10/300 GL column and DNA-barcoded CZA97 and DNA-barcoded HA were run on the Superdex 200 Increase 10/300 GL on the AKTA FPLC system. For size exclusion chromatography, dotted lines indicate DNA-barcoded antigens and fractions taken. The second peak indicates excess oligonucleotide from the conjugation reaction. (B.) Binding of VRC01 or Fe53 Ramos B-cell lines to DNA-barcoded, fluorescently labeled antigens via flow cytometry. VRC01 cells bind to DNA-barcoded BG505-PE, DNA-barcodedCZA97-PE and not DNA-barcoded HA-PE. Fe53 cells bind to DNA-barcoded HA-PE.

Figure 4:
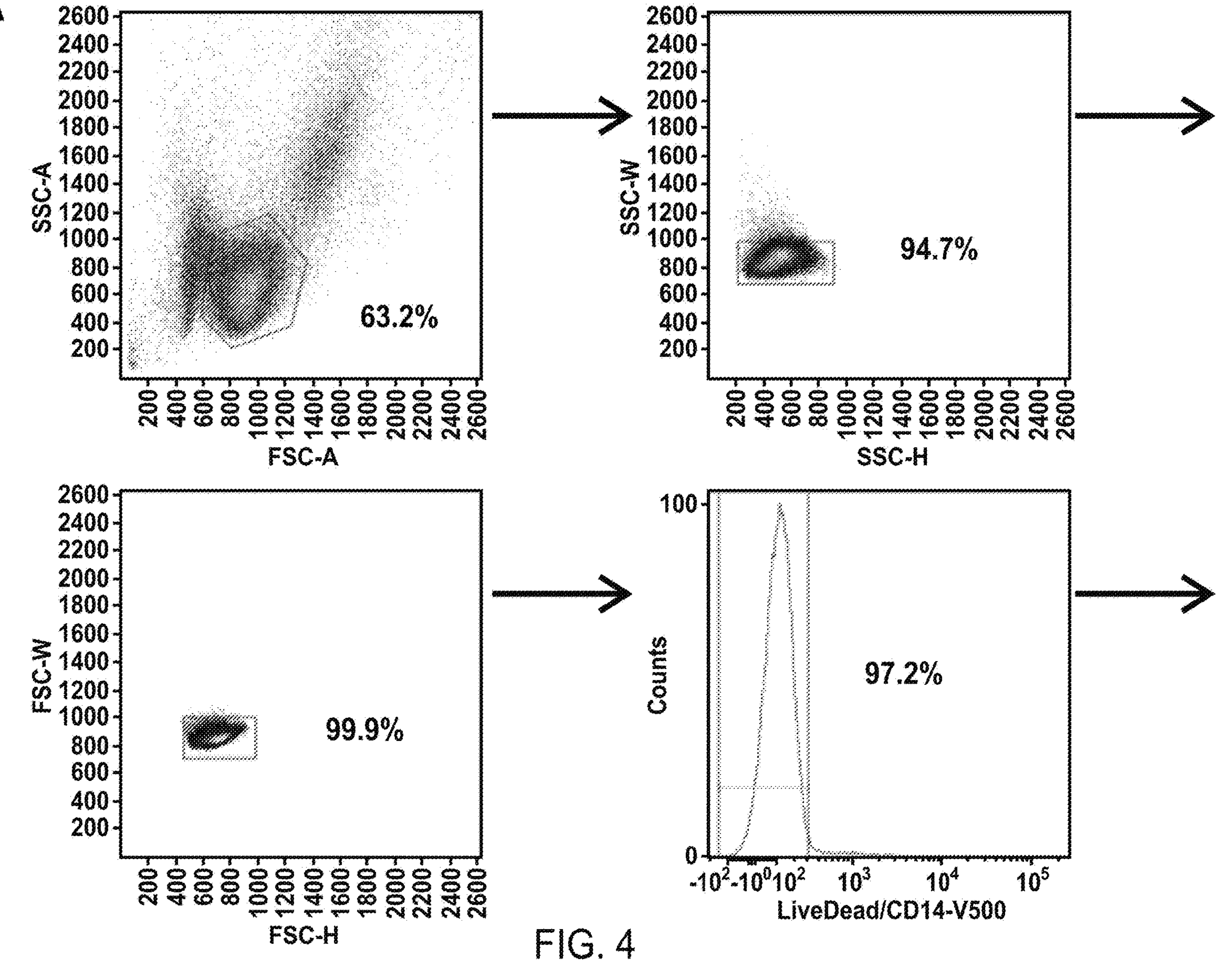
Figure 4:
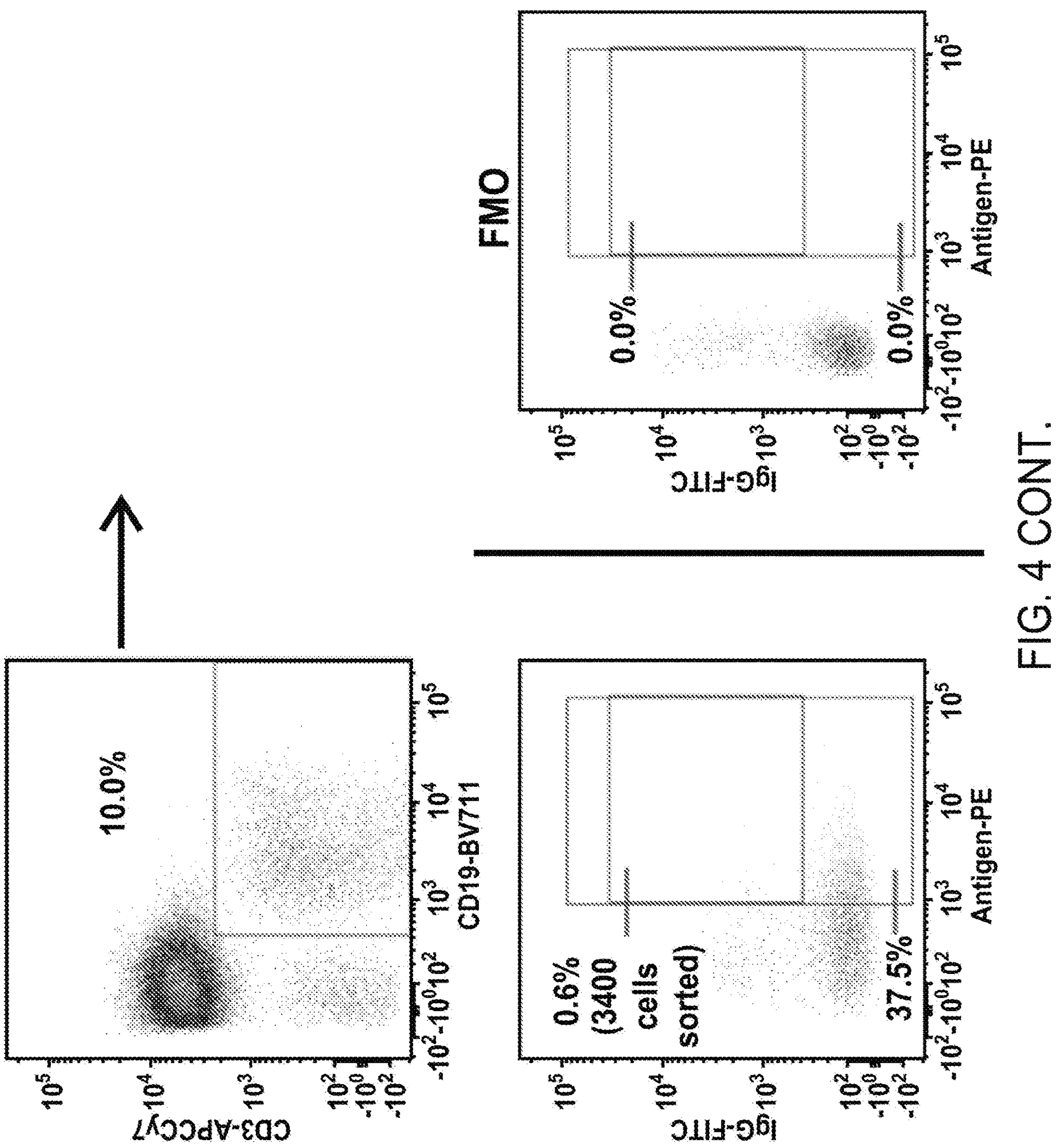
Figure 4:
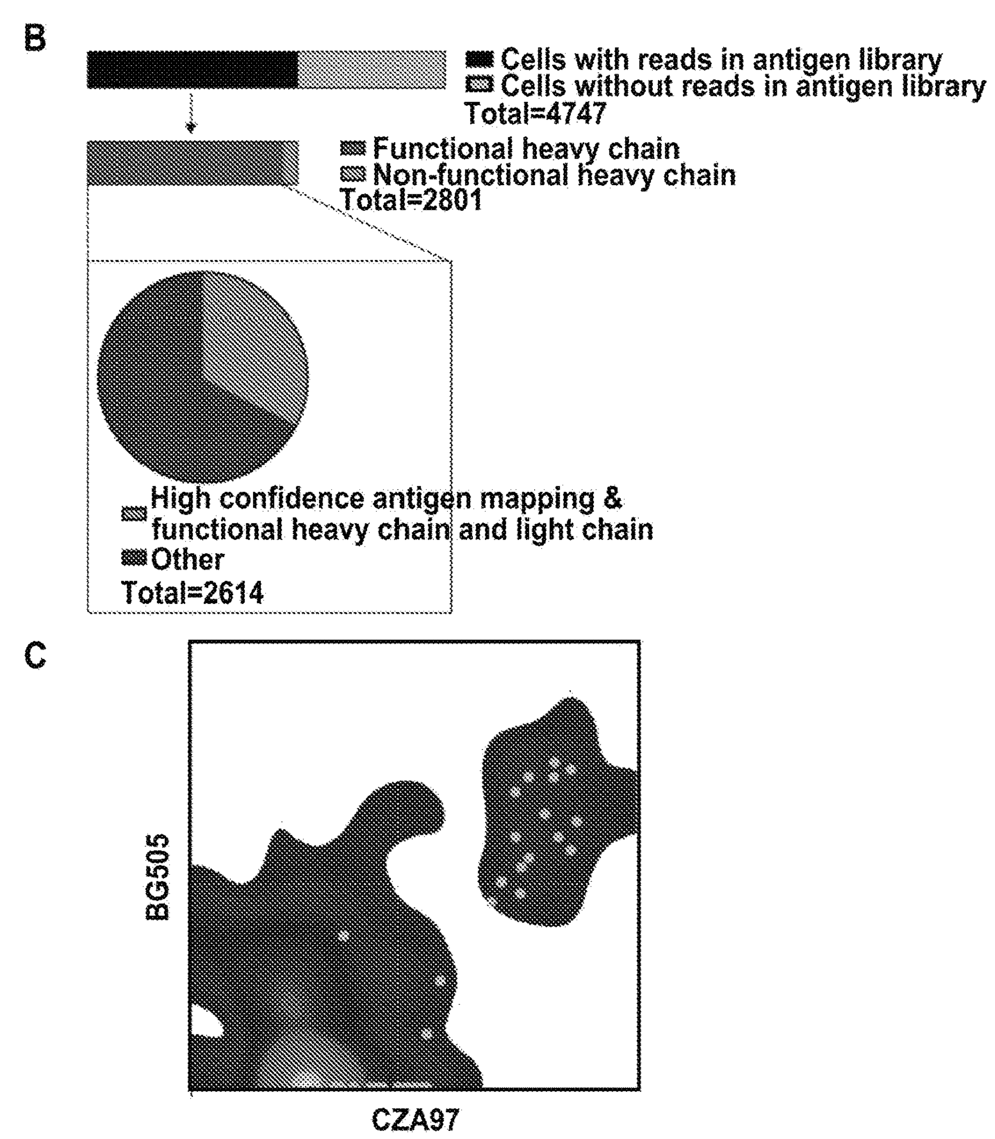

FIG. 4. Identification of antigen-specific B cells from donor NIAID 45 PBMCs (A.) Gating scheme for fluorescence activated cell sorting of donor NIAID 45 PBMCs. Cells were stained with LiveDead-V500, CD14-V500, CD3-APCCy7, CD19-BV711, IgG-FITC, and a DNA-barcoded antigen screening library consisting of BG505-PE, CZA97-PE, and HA-PE. Gates as drawn are based on gates used during the sort, and percentages from the sort are listed. These plots show a starting number of 50,187 total events. For IgG positive, antigen positive cells, 18 cells are shown in the plot, but in reality, 3400 IgG positive, antigen positive cells were sorted and supplemented with 13,000 antigen positive B cells for single cell sequencing. A small aliquot of donor 45 PBMCs were used for fluorescence minus one (FMO) staining, and were stained with the same antibody panel as listed above without the antigen screening library. (B.) Number of recovered linked cells. 4747 cells were recovered by cellranger from the BCR sequencing libraries as having BCR contigs, of which 2801 had reads in the antigen barcode libraries. Of these, 848 had functional heavy and light chain sequences and high-confidence antigen mapping information. (C.) LIBRA-seq scores for BG505 (x-axis) and CZA97 (y-axis) are shown. Each axis represents the minimum to maximum LIBRA-seq score for each antigen. Density of total cells is shown, with purple to yellow indicating lowest to highest number of cells. Overlaid on the density plot are the 30 VRC01 lineage members indicated in light blue.

Figure 5:
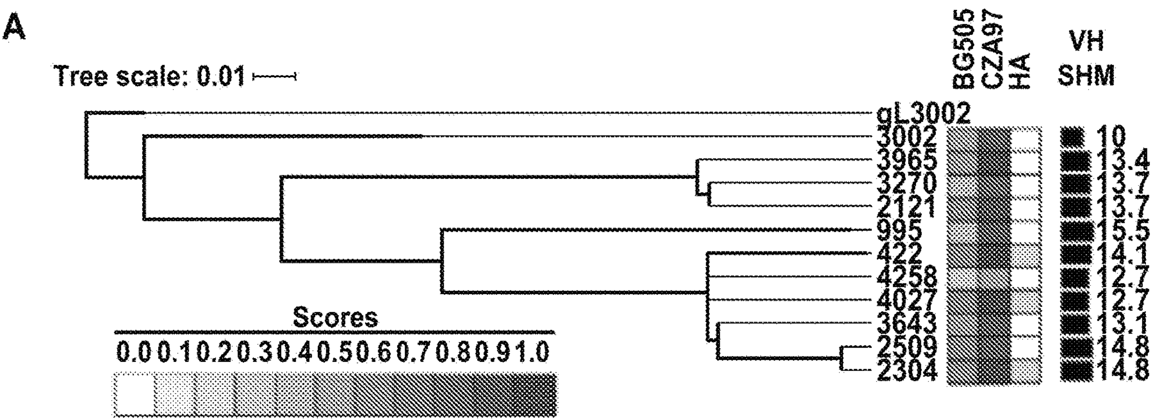

FIG. 5. Antibody lineage 2121 is neutralizing and directed to the CD4 binding site. (A.) Phylogenetic tree showing relatedness antibody lineage 2121, isolated from donor 45 using LIBRA-seq. Each row represents an antibody, with sequences that were recombinantly expressed and tested for binding by ELISA are shown in red. Sequences recovered with LIBRA-seq, along with germline-reverted 3002 (since it had the least amount of heavy chain somatic hypermutation) were aligned using clustal W and a maximum likelihood tree was inferred using PhyML. The resulting tree was visualized using germline-reverted 3002 as the root. For each antibody isolated from LIBRA-seq, a heat map of the LIBRA-seq scores for each antigen (BG505, CZA97, and HA) is shown. Light to dark blue represents low to high scores. Amount of somatichypermutation (SHM) at the nucleotide level for the heavy and light chain variable genes are displayed as bars, with the numerical percentage value listed to the right of the bar. Length of the bar corresponds to amount of mutation. Lineage 2121 uses IGHV4-39 and IGKV3-20. Amino acid sequences of the complementarity determining region 3 for the heavy chain (CDRH3) and the light chain(CDRL3) for each antibody. (B.) Binding of BG505 DS-SOSIP trimer to (a) PGT145 IgG, (b) VRC01

IgG, (c) 17b IgG, and (d) 2723-2121 IgG. (C.) Neutralization of Tier 1, Tier 2, and control viruses by antibody 2723-2121 and VRC01. (D.) Inhibition of BG505 DS-SOSIP binding to 2723-2121 IgG in presence of VRC34 Fab(diamond), PGT145 Fab (square) and VRC01 Fab (triangle).

```
                                    (SEQ ID NO: 43)
ARHRADFDFWNRGNLRGYFDP;

                                     (SEQ ID NO:73)
QQYGTSPTT;

                                    (SEQ ID NO: 44)
ARHRADYDFWNGNNLRGYFDP;

                                    (SEQ ID NO: 74)
QQYGSSPTT;

                                    (SEQ ID NO: 45)
ARHRAGYDFWSGSNLRGYFDP;

                                    (SEQ ID NO: 75)
QQYGSSPAT;

                                    (SEQ ID NO: 46)
ARHRANYDFWGGSNLRGYFDP;

                                    (SEQ ID NO: 76)
QQYGTSPTT;

                                    (SEQ ID NO: 47)
ARHRADYDFWGGSNLRGYFDP;

                                     (SEQ ID NO:77)
QQYGTSPTT.
```

Figure 6:
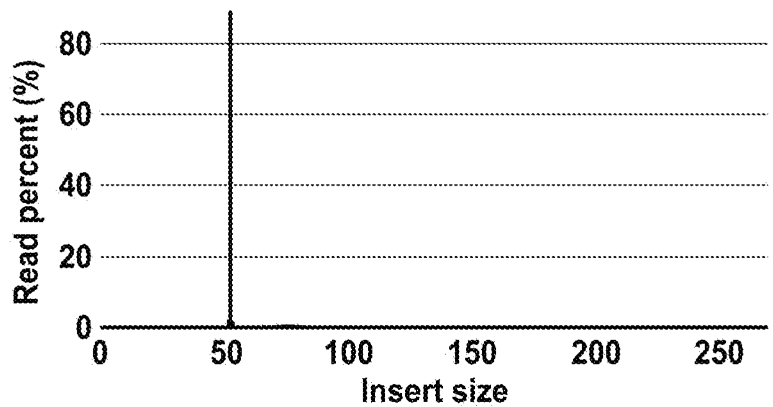
Figure 6:
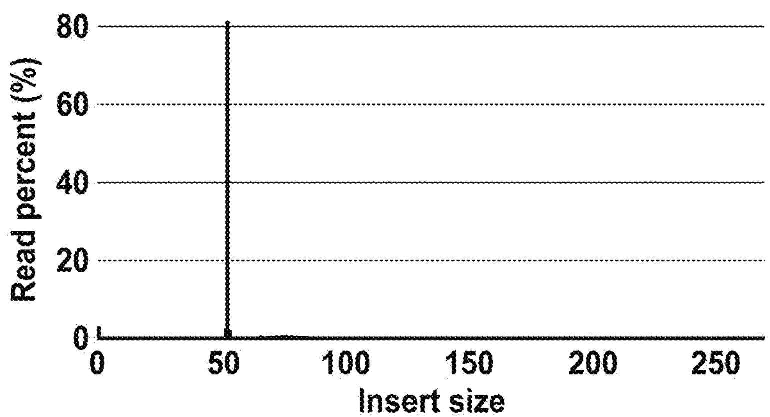

FIG. 6. Sequencing preprocessing and quality statistics. (A.) Quality filtering of the antigen barcode FASTQ files. fastp was used to trim adapters and remove low-quality reads using default parameters. Shown are read and base statistics generated from the output html report from each of the Ramos B cell experiment (left) and primary B cell experiment from donor NIH45 (right). (B.) Shown is a distribution of insert sizes of the antigen barcode reads from the Ramos B cellline experiment, as output from the fastp html report (C.) Shown is a distribution of insert sizes of the antigen barcode reads from the donor NIH45 experiment, as output from the fastp html report.

Figure 7:
Figure 7:
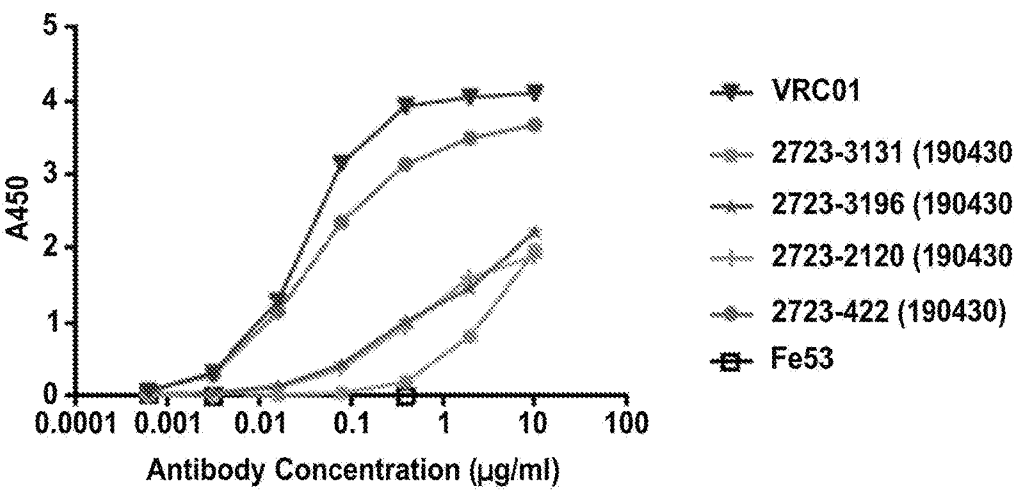
Figure 7:
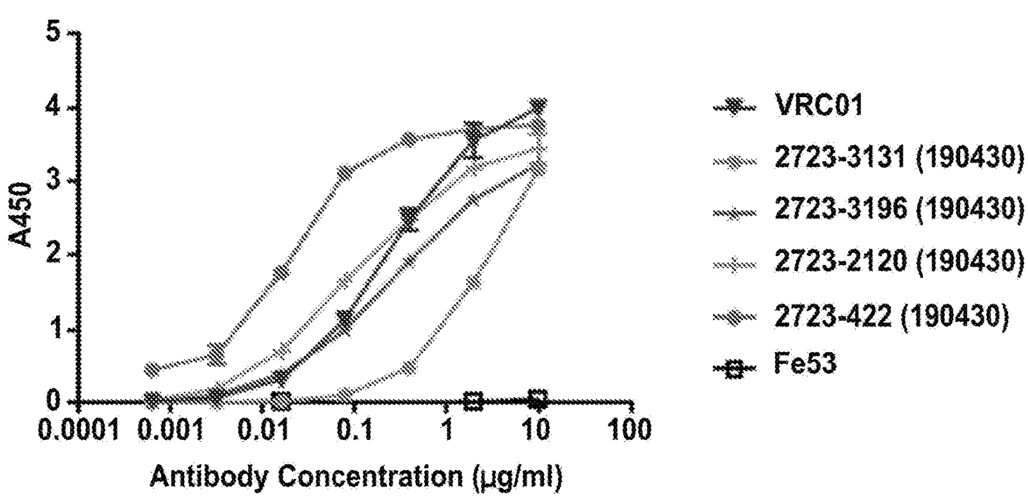
Figure 7:
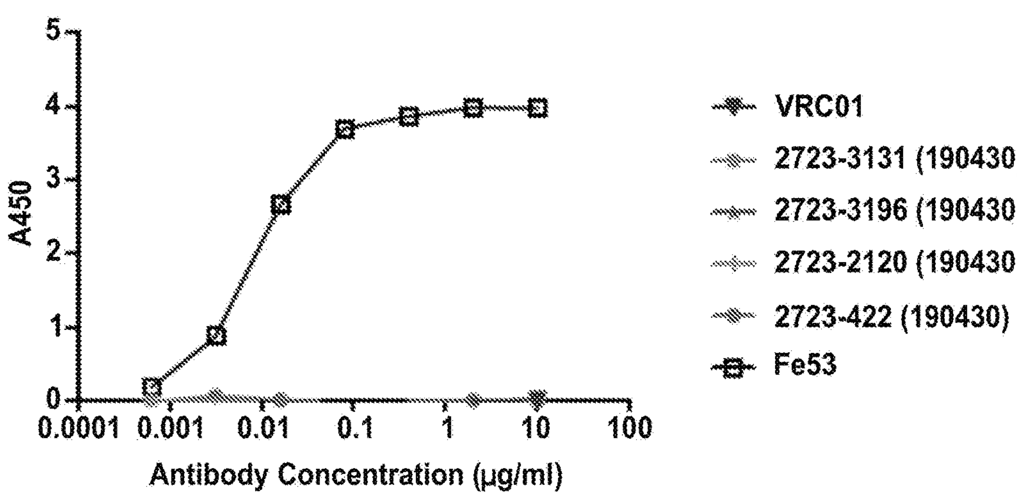

FIG. 7. ELISA binding of additional LIBRA-seq-identified antibodies to recombinant HIV-1 Env (left and middle) and influenza HA (right) antigen proteins. Antibodies from donor 45 from the Vanderbilt HIV infection cohort were tested for binding to the same antigens as used in the LIBRA-seq screening library. Recombinant VRC01 (cyan) and Fe53 (purple) were used as controls.

Figure 8:
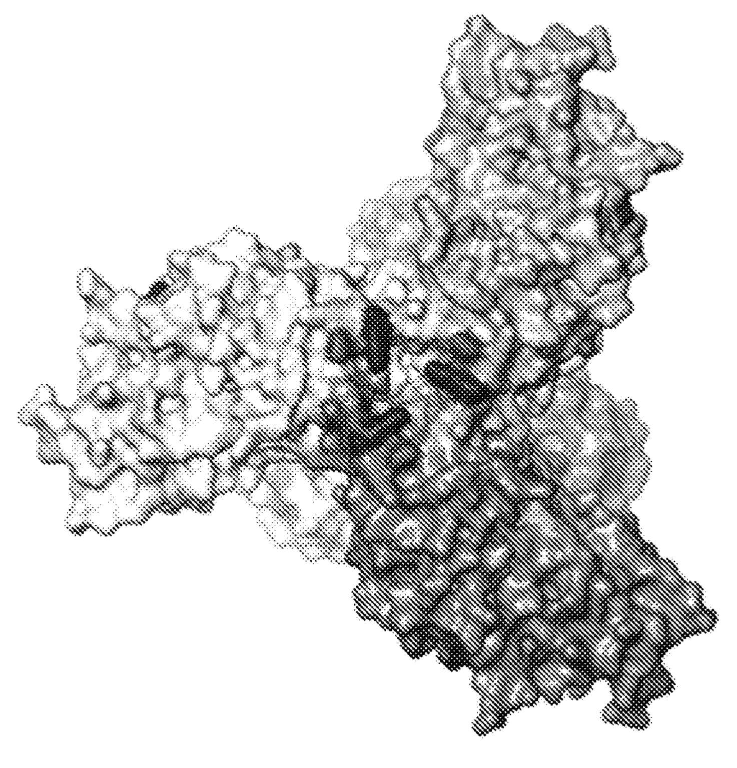

FIG. 8. High-throughput epitope mapping to determine residue-level epitope information. A structural model of trimeric HIV-1 Env stabilized in a closed prefusion conformation is shown with highlighted epitope-specific mutations (colors). In addition, an influenza HA control (not pictured) was also used as part of the antigen screening library. The results for VRC01 B cells are a reduction in signal for the D368R antigen compared to other HIV-1 Env variants.

Figure 9:
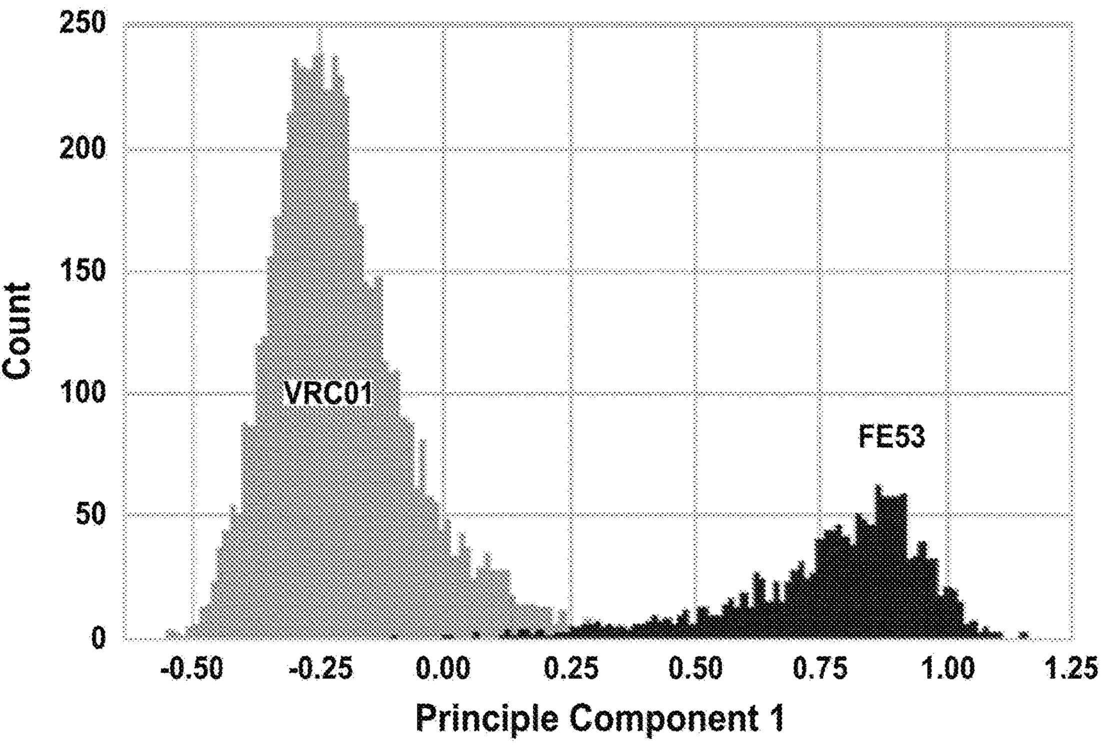

FIG. 9. A single principal component (PC) separates 7046 cells by antigen specificity, for the experiment represented in FIG. 8.

Figure 10:
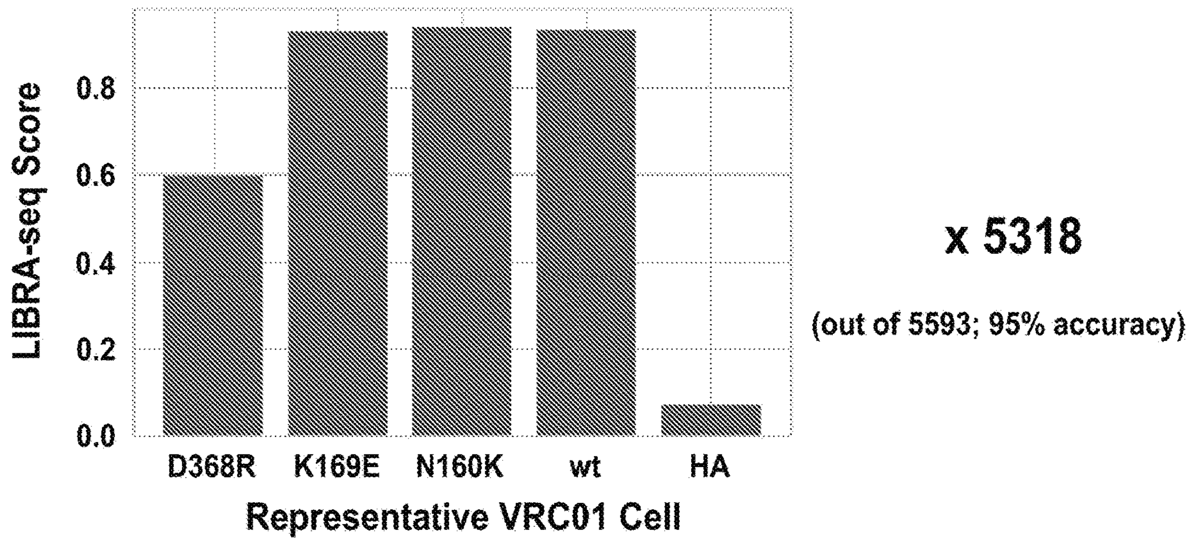

FIG. 10. Single VRC01 cells and their binding pattern (reduction in D368R signal, no effect on other Env variants, and low signal for HA), with epitope mapped to HIV-1 Env CD4bs. Out of 5593 VRC01 cells, this epitope pattern was observed for ~95% of the cells. Shown are the LIBRA-seq scores (blue bars) for a representative VRC01 cell with this epitope pattern.

Figure 11:
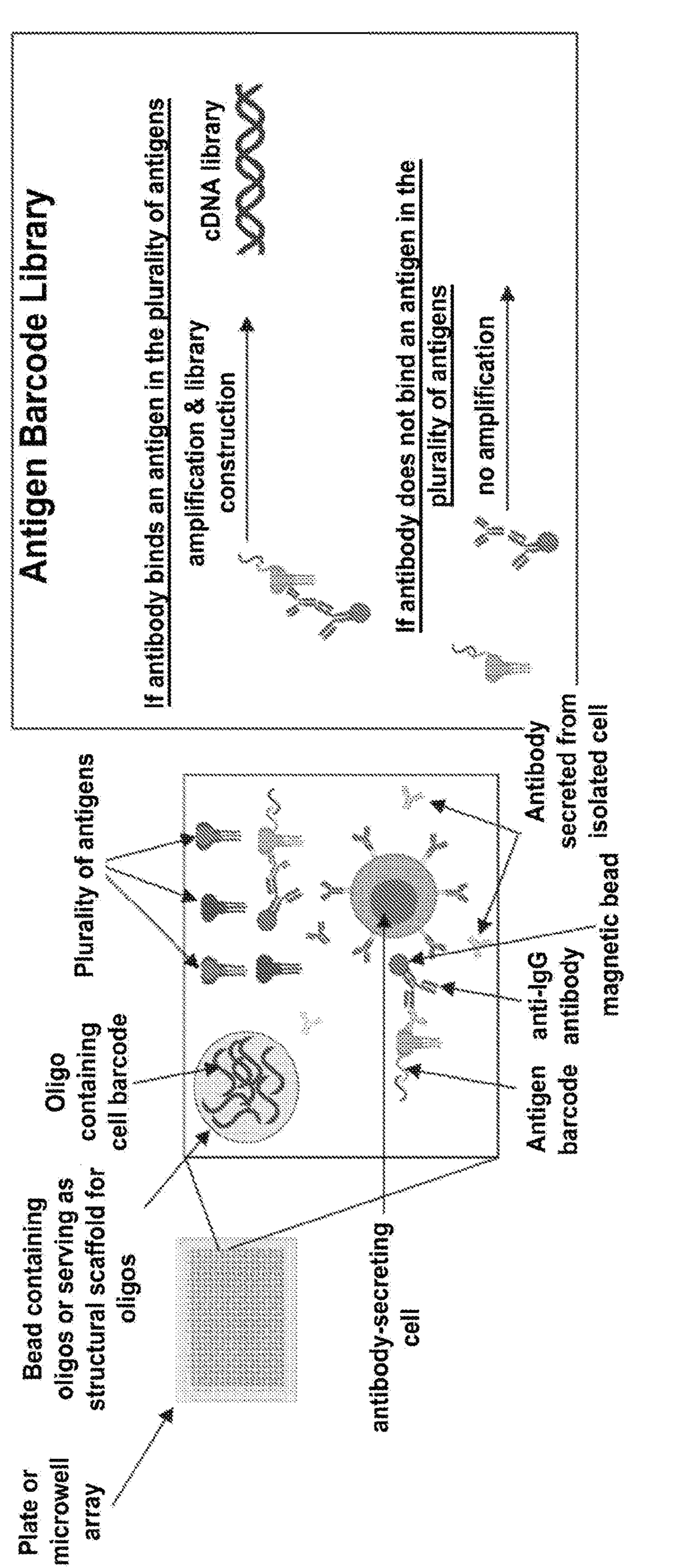

FIG. 11. Diagram of LIBRA-seq application to antibody-secreting cells.

Figure 12:
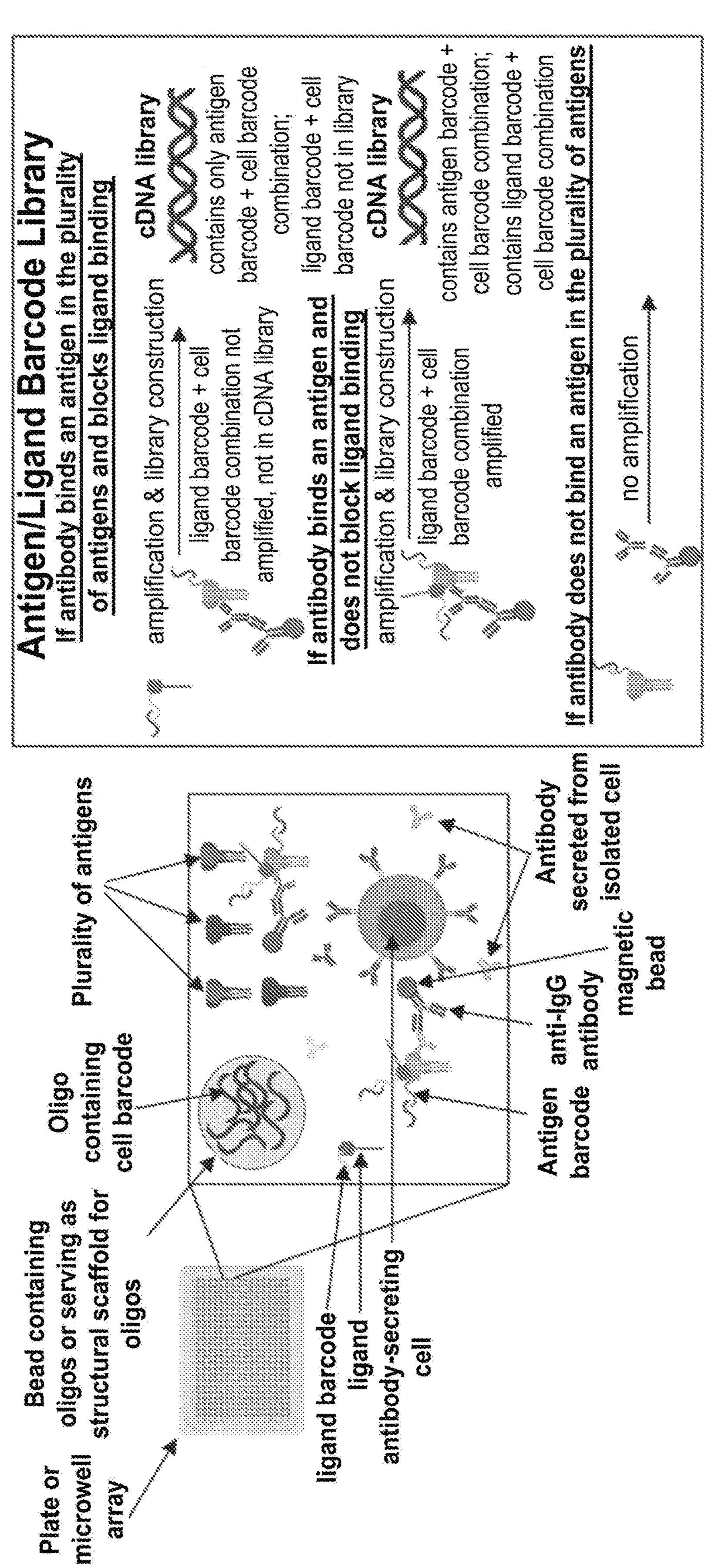

FIG. 12. Diagram of a ligand-blocking assay using LIBRA-seq to screen antibody-secreting cells.

DETAILED DESCRIPTION

Disclosed herein are systems and methods for simultaneous detection of antigens and antigen specific antibodies.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

"Nucleotide," "nucleoside," "nucleotide residue," and "nucleoside residue," as used herein, can mean a deoxyribonucleotide, ribonucleotide residue, or another similar nucleoside analogue. A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3-AMP (3-adenosine monophosphate) or 5'-GMP (5'-guanosine monophosphate). There are many varieties of these types of molecules available in the art and available herein.

The method and the system disclosed here including the use of primers, which are capable of interacting with the disclosed nucleic acids, such as the antigen barcode as disclosed herein. In certain embodiments the primers are used to support DNA amplification reactions. Typically, the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically, the disclosed primers hybridize with the disclosed nucleic acids or region of the nucleic acids or they hybridize with the complement of the nucleic acids or complement of a region of the nucleic acids.

The term “amplification” refers to the production of one or more copies of a genetic fragment or target sequence, specifically the “amplicon”. As it refers to the product of an amplification reaction, amplicon is used interchangeably with common laboratory terms, such as “PCR product.”

The term “polypeptide” refers to a compound made up of a single chain of D- or L-amino acids or a mixture of D- and L-amino acids joined by peptide bonds.

As used herein, the term “antigen” refers to a molecule that is capable of binding to an antibody. In some embodiment, the antigen stimulates an immune response such as by production of antibodies specific for the antigen. Antigens of the present invention can be, for example, an antigen from human immunodeficiency virus (HIV), an antigen from influenza virus, or an antigen from respiratory syncytial virus (RSV). Antigens of the present invention can also be, for example, a human antigen (e.g. VEGF, or an oncogene-encoded protein).

In the present invention, “specific for” and “specificity” means a condition where one of the molecules is involved in selective binding. Accordingly, an antibody that is specific for one antigen selectively binds that antigen and not other antigens.

The term “antibodies” is used herein in a broad sense and includes both polyclonal and monoclonal antibodies. In addition to intact immunoglobulin molecules, also included in the term “antibodies” are fragments or polymers of those immunoglobulin molecules, and human or humanized versions of immunoglobulin molecules or fragments thereof, as long as they are chosen for their ability to specifically interact with the HIV virus, such that the HIV viral infection is prevented, inhibited, reduced, or delayed. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

Each antibody molecule is made up of the protein products of two genes: heavy-chain gene and light-chain gene. The heavy-chain gene is constructed through somatic recombination of V, D, and J gene segments. In human, there are 51 VH, 27 DH, 6 JH, 9 CH gene segments on human chromosome 14. The light-chain gene is constructed through somatic recombination of V and J gene segments. There are 40 Vκ, 31 Vλ, 5 Jκ, 4 Jλ gene segments on human chromosome 14 (80 VJ). The heavy-chain constant domains that correspond to the different classes of immunoglobulins are called α, δ, ε, γ, and μ, respectively. The “light chains” of antibodies from any vertebrate species can be assigned to one of two clearly distinct types, called kappa (κ) and lambda (λ), based on the amino acid sequences of their constant domains.

The term “monoclonal antibody” as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include “chimeric” antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment.

Pepsin treatment yields a fragment that has two antigen combining sites and is still capable of cross linking antigen.

As used herein, the term "antibody or antigen binding fragment thereof" or "antibody or fragments thereof" encompasses chimeric antibodies and hybrid antibodies, with dual or multiple antigen or epitope specificities, and fragments, such as F(ab')2, Fab', Fab, Fv, sFv, scFv and the like, including hybrid fragments. Thus, fragments of the antibodies that retain the ability to bind their specific antigens are provided. For example, fragments of antibodies which maintain HIV virus binding activity are included within the meaning of the term "antibody or antigen binding fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or antigen binding fragment thereof" are conjugates of antibody fragments and antigen binding proteins (single chain antibodies). Also included within the meaning of "antibody or antigen binding fragment thereof" are immunoglobulin single variable domains, such as for example a nanobody.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Systems and Methods

Disclosed herein are systems and methods for simultaneous detection of antigens and antigen specific antibodies. In some aspects, disclosed herein is a system for simultaneous detection of an antigen and an antibody that specifically binds said antigen, comprising: a plurality of barcode-labeled antigens; a population of B-cells; and a pool of cell barcode-labeled beads.

In some embodiments, the barcode-labeled antigens are labeled with a first barcode comprising a DNA sequence or an RNA sequence. In some embodiments, the barcode-labeled antigens are labeled with a first barcode comprising a DNA sequence. In some embodiments, the barcode-labeled antigens are labeled with a first barcode comprising an RNA sequence.

In some embodiments, the cell barcode-labeled beads are labeled with a second barcode comprising a DNA sequence or an RNA sequence. In some embodiments, the cell barcode-labeled beads are labeled with a second barcode comprising a DNA sequence. In some embodiments, the cell barcode-labeled beads are labeled with a second barcode comprising an RNA sequence. In some embodiments, the cell barcode-labeled beads are labeled with a barcode on the inside of the bead. In some embodiments, the cell barcode-labeled beads are labeled with a barcode encapsulated within the bead. In some embodiments, the cell barcode-labeled beads are labeled with a barcode on the outside of the bead.

These oligos, which contain the cell barcode, both: (1) enable amplification of cellular mRNA transcripts through the template switch oligo that is part of the oligo containing the cell barcode, and (2) directly anneal to the antigen barcode-containing oligos from the antigen. In some embodiments, the oligos delivered from the beads have the general structure: P5_PCR_handle-Cell_barcode-UMI-Template_switch_oligo.

In some embodiments, the barcode-labeled antigens comprise an antigen from a pathogen or an animal. In some embodiments, the barcode-labeled antigens comprise an antigen from a pathogen. In some embodiments, the barcode-labeled antigens comprise an antigen from an animal. In some embodiments, the animal is a mammal, including, but not limited to, primates (e.g., humans and nonhuman primates), cows, sheep, goats, horses, dogs, cats, rabbits, rats, mice and the like. In some embodiments, the subject is a human.

In some embodiments, the antigen from a pathogen comprises an antigen from a virus. In some embodiments, the antigen from a virus comprises an antigen from human immunodeficiency virus (HIV), an antigen from influenza virus, or an antigen from respiratory syncytial virus (RSV).

In some embodiments, the antigen from a virus comprises an antigen from human immunodeficiency virus (HIV). In some embodiments, the antigen from a virus comprises an antigen from influenza virus. In some embodiments, the antigen from a virus comprises an antigen from respiratory syncytial virus (RSV).

In some embodiments, the antigen from HIV comprises an antigen from HIV-1. In some embodiments, the antigen from HIV comprises an antigen from HIV-2. In some embodiments, the antigen from HIV comprises HIV-1 Env. In some embodiments, the antigen from influenza virus comprises hemagglutinin (HA). In some embodiments, the antigen from RSV comprises an RSV F protein. In some embodiments, the antigen is selected from the antigens listed in Table 1. The sequences of the antigens herein are known in the art and can be found at a number of sequence databases, for example, the National Center for Biotechnology Information (NCBI).

In some embodiments, the antigen from an animal comprises an antigen from a human. In some embodiments, the antigen from a human comprises a vascular endothelial growth factor (VEGF) protein. In some embodiments, the antigen from a human comprises an oncogene-encoded protein, including, for example, HER-2/neu, RAS, MYC, SRC, telomerase, BCL-2, EGFR, p53, BRCA, Rb, APC, CDKN2A, PTEN, VHL, or WRN.

In some embodiments, the population of B-cells comprise a memory B-cell, a plasma cell, a naïve B cell, an activated B-cell, or a B-cell line.

In some embodiments, the population of B-cells comprise a memory B-cell, a plasma cell, a naïve B cell, an activated B-cell, or a B-cell line. In some embodiments, the population of B-cells comprise a plasma cell. In some embodiments, the population of B-cells comprise a naïve B cell. In some embodiments, the population of B-cells comprise an activated B-cell. In some embodiments, the population of B-cells comprise a B-cell line.

In some embodiments, the B-cell line comprises VRC01, PGT128, PGT145, VRC34, 10E8, 447-52D, Fe53, or CH65. In some embodiments, the B-cell line comprises VRC01. In some embodiments, the B-cell line comprises PGT128. In some embodiments, the B-cell line comprises PGT145. In some embodiments, the B-cell line comprises VRC34. In some embodiments, the B-cell line comprises 10E8. In some embodiments, the B-cell line comprises 447-52D. In some embodiments, the B-cell line comprises Fe53. In some embodiments, the B-cell line comprises CH65.

In some embodiments, the plurality of antigens comprise a panel of epitope knock-outs. In some embodiments, the plurality of antigens comprise a panel of antigen variants or mutations for epitope mapping.

In some aspects, disclosed herein is a system for simultaneous detection of an antigen and an antibody that specifically binds said antigen, comprising: a barcode-labeled antigen; a population of B-cells; and a pool of cell barcode-labeled beads.

It should be understood that the barcode described above is conjugated to the barcode-labeled antigen in a way that is known to one of ordinary skill in the art. Conjugates can be chemically linked to the nucleotide or nucleotide analogs. Such conjugates include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., Ann. N.Y. Acad. Sci., 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937. An oligonucleotide barcode can also be conjugated to an antigen using the Solulink Protein-Oligonucleotide Conjugation Kit (TriLink cat no.S-9011) according to manufacturer's instructions. Briefly, the oligo and protein are desalted, and then the amino-oligo is modified with the 4FB crosslinker, and the biotinylated antigen protein is modified with S-HyNic. Then, the 4FB-oligo and the HyNic-antigen are mixed together. This causes a stable bond to form between the protein and the oligonucleotide.

As used herein, "beads" is not limited to a specific type of bead. Rather, a large number of beads are available and are known to one of ordinary skill in the art. A suitable bead may be selected on the basis of the desired end use and suitability for various protocols. In some embodiments, the bead is or comprises a particle or a bead. Beads can comprise particles that have been described in the art in, for example, U.S. Pat. Nos. 5,084,169, 5,079,155, U.S. Pat. No. 473,231, and U.S. Pat. No. 8,110,351. The particle or bead size can be optimized for binding a cell in a single cell emulsion and optimized for the subsequent PCR reaction.

In another aspect, disclosed herein is a method for simultaneous detection of an antigen and an antigen specific antibody, comprising:

labeling a plurality of antigens with unique antigen barcodes;

providing a plurality of barcode-labeled antigens to a population of B-cells;

allowing the plurality of barcode-labeled antigens to bind to the population of B-cells; washing unbound antigens from the population of B-cells;

separating the B-cells into single cell emulsions;

introducing into each single cell emulsion a unique cell barcode-labeled bead; preparing a single cell cDNA library from the single cell emulsions;

performing PCR amplification reactions to produce a plurality of amplicons, wherein the amplicons comprise: 1) the cell barcode and the antigen barcode, and 2) the cell barcode and i) an immunoglobulin heavy chain (VDJ) sequence, or ii) an immunoglobulin light chain (VJ) sequence; and sequencing the plurality of amplicons.

In another aspect, disclosed herein is a method for simultaneous detection of an antigen and an antigen specific antibody, comprising:

labeling a plurality of antigens with unique antigen barcodes;

providing a plurality of barcode-labeled antigens to a population of B-cells;

allowing the plurality of barcode-labeled antigens to bind to the population of B-cells;

washing unbound antigens from the population of B-cells;

optionally isolating antigen positive cells using fluorescence activated cell sorting;

separating the B-cells into single cell emulsions;

introducing into each single cell emulsion a unique cell barcode-labeled bead;

preparing a single cell cDNA library from the single cell emulsions;

performing PCR amplification reactions to produce a plurality of amplicons, wherein the amplicons comprise: 1) the cell barcode and the antigen barcode, and 2) the cell barcode and i) an immunoglobulin heavy chain (VDJ) sequence, and/or ii) an immunoglobulin light chain (VJ) sequence;

sequencing the plurality of amplicons; and identifying the i) antigen barcodes and ii) immunoglobulin heavy chain (VDJ) sequence and/or immunoglobulin light chain (VJ) sequence, with matching cell barcodes.

Also disclosed herein is a set of PCR primers for performing PCR amplification reactions to produce a plurality of amplicons, wherein the amplicons comprise: 1) the cell barcode and the antigen barcode, and 2) the cell barcode and i) an immunoglobulin heavy chain (VDJ) sequence, or ii) an immunoglobulin light chain (VJ) sequence.

In another aspect, disclosed herein is a method for simultaneous detection of an antigen and an antigen specific antibody, comprising:

- labeling a plurality of antigens with unique antigen barcodes;
- providing a plurality of barcode-labeled antigens to a population of B-cells or peripheral blood mononuclear cells (PBMCs) comprising B-cells;
- allowing the plurality of barcode-labeled antigens to bind to the population of B-cells;
- washing unbound antigens from the population of B-cells;
- separating the population of B-cells into single B-cells;
- combining the single B-cells with a unique cell barcode-labeled bead;
- preparing a single cell cDNA library from the combined single B-cells and cell barcode-labeled beads;
- performing PCR amplification reactions to produce a plurality of amplicons, wherein the amplicons comprise: 1) the cell barcode and the antigen barcode, and 2) the cell barcode and i) an immunoglobulin heavy chain (VDJ) sequence, or ii) an immunoglobulin light chain (VJ) sequence; and
- sequencing the plurality of amplicons.

Also disclosed herein is a set of PCR primers for performing PCR amplification reactions to produce a plurality of amplicons, wherein the amplicons comprise: 1) the cell barcode and the antigen barcode; 2) the cell barcode and an immunoglobulin heavy chain (VDJ) sequence; and/or 3) the cell barcode and an immunoglobulin light chain (VJ) sequence.

In another aspect, disclosed herein is a method for simultaneous detection of an antigen and an antigen specific antibody, comprising:

- labeling a plurality of antigens with unique antigen barcodes;
- providing a plurality of barcode-labeled antigens to a population of B-cells;
- allowing the plurality of barcode-labeled antigens to bind to the population of B-cells;
- washing unbound antigens from the population of B-cells;
- separating the B-cells into single cell emulsions;
- introducing into each single cell emulsion a unique cell barcode-labeled bead;
- preparing a single cell cDNA library from the single cell emulsions;
- performing PCR amplification reactions to produce a plurality of amplicons, wherein the amplicons comprise: 1) the cell barcode and the antigen barcode; 2) the cell barcode and an immunoglobulin heavy chain (VDJ) sequence; and 3) the cell barcode and an immunoglobulin light chain (VJ) sequence; and
- sequencing the plurality of amplicons.

In some embodiments, the plurality of barcode-labeled antigens are provided to a population of B-cells. In some embodiments, the plurality of barcode-labeled antigens are provided to a population of peripheral blood mononuclear cells (PBMCs) comprising B-cells.

In some embodiments, the population of B-cells are separated into single B-cells by cell emulsion (droplet fluidics). In some embodiments, the population of B-cells are separated into single B-cells in microwell or plate-based assays.

In some embodiments, the combining the single B-cells with the unique cell barcode-labeled bead is performed by cell emulsion (droplet fluidics). In some embodiments, the combining the single B-cells with the unique cell barcode-labeled bead is performed by co-encapsulation of the single B-cells with the unique cell barcode-labeled bead.

In another aspect, disclosed herein is a method for simultaneous detection of an antigen and an antibody that specifically binds said antigen, comprising:

- labeling a plurality of antigens with unique antigen barcodes;
- providing a plurality of barcode-labeled antigens to a population of B-cells;
- allowing the plurality of barcode-labeled antigens to bind to the population of B-cells;
- washing unbound antigens from the population of B-cells;
- separating the B-cells into single cell emulsions;
- introducing into each single cell emulsion a unique cell barcode-labeled bead;
- preparing a single cell cDNA library from the single cell emulsions;
- incubating the single cell cDNA library to allow hybridization of the unique cell barcode-labeled bead with the barcode-labeled antigens, immunoglobulin heavy chain (VDJ) cDNAs, and immunoglobulin light chain (VJ) cDNAs;
- performing a PCR amplification reaction to produce a plurality of amplicons, wherein the amplicons comprise: 1) the cell barcode and the antigen barcode, and 2) the cell barcode and i) an immunoglobulin heavy chain (VDJ) sequence, or ii) an immunoglobulin light chain (VJ) sequence; and
- sequencing the plurality of amplicons.

Also disclosed herein is a set of PCR primers for performing a PCR amplification reaction to produce a plurality of amplicons, wherein the amplicons comprise: 1) the cell barcode and the antigen barcode, and 2) the cell barcode and i) an immunoglobulin heavy chain (VDJ) sequence, or ii) an immunoglobulin light chain (VJ) sequence.

In some embodiments, the PCR amplification reactions are performed in one multiplexed reaction. In some embodiments, the PCR amplification reactions are performed in separate PCR reactions. In some embodiments, the B cell receptor (BCR) libraries can be obtained wherein all cellular mRNA is made into a cDNA library, and then primers are used to amplify BCR transcripts. out of the cDNA library. In some embodiments, the B cell receptor (BCR) libraries can be obtained wherein the BCR mRNA transcripts are directly consumed and made into cDNA.

The LIBRA-seq technology can be used in various applications, such as determining antigen specificity and cross reactivity.

The LIBRA-seq technology can also be used for epitope mapping, using the LIBRAE-seq methods described in the examples below. This can use an antigen panel of epitope knock-outs as the screening library. LIBRAE-seq can also use a panel of antigen variants that can be used for epitope mapping by binding fingerprinting. (Georgiev, I. et al. (2013). Delineating Antibody Recognition in Polyclonal Sera from Patterns of HIV-1 Isolate Neutralization. *Science,* 340(6133), 751-756).

The LIBRA-seq technology can also be used for cross-species assays. The LIBRA-seq can use a panel consisting of homologs of a protein from various species (useful for identifying antibodies that target an antigen variant in one species but not in others).

The LIBRA-seq technology can also be applied in a plate-based format, where it can be used for antigen specificity, cross-reactivity, epitope mapping, etc. Oligo-conjugated antigens are incubated with B cell population of interest and washed as in typical LIBRA-seq workflow.

Instead of using the microfluidics device, antigen-positive B cells are single-cell sorted into individual wells of a plate. Primers used to amplify BCR and antigen-oligo sequences contain a plate/well specific index. The resulting amplicons are pooled and sequenced.

A number of antigen library formats can be used. Recombinant antigen proteins can be expressed and purified before labeling with oligos. Whole virus can be tagged with barcode. This can use scRNA-seq to exploit the intrinsic diversity within variants of the same virus (e.g., different strains of HIV-1). Pseudovirus can contain internal barcode. Comprehensive mutant virus libraries can be generated using the methods of (e.g. Dingens et al (2019). An Antigenic Atlas of HIV-1 Escape from Broadly Neutralizing Antibodies Distinguishes Functional and Structural Epitopes. Immunity, 50(2):520-532.e3). Whole cells can be also tagged either by lentiviral transfection with barcode or crispr-based tagging.

Antigens can be arranged in a plate format for microexpression. Each antigen is expressed in microculture in a single well on a plate. A unique barcode is added to each well. Barcoded antigens are mixed together, mixed with B cells, and LIBRA-seq is executed as described.

Antigens can also be formatted into antigen microarrays (for example, VirScan technology, as described in Xu G J, et al. Comprehensive serological profiling of human populations using a synthetic human virome. Science. 2015; 348 (6239):aaa0698). DNA microarrays can be used followed by phage display of antigens. However, here a unique barcode is added to each antigen in the microarray.

LIBRA-seq can also be performed in a microwell format. Custom microwell arrays (as described in Gierahn, T. M., et al. ((2017). Seq-Well: Portable, low-cost rna sequencing of single cells at high throughput. *Nature Methods*. https://doi.org/10.1038/nmeth.4179) or commercially-available (ie, Celsee Genesis system) for gravity-based isolation of single B cells into microwells. The remainder of the LIBRA-seq method is performed as described herein.

LIBRA-seq can also be used on antibody secreting cells/hybridomas. For antibody-secreting cells the assay is modified. Oligo-tagged antigens, primer beads, and anti-IgG antibodies with a magnetic bead are added to the microwell array. B cells are added, and 1 B cell is deposited in each microwell. The array is sealed with a semi-permeable membrane, and the cells sit for a few hours to secrete sufficient antibody. Cell barcodes are appended to cellular BCR transcripts and antigen oligos (as described in the LIBRA-seq method). The magnetic beads are separated: (i) If the secreted IgG antibody binds the antigen, a complex is formed: Anti_IgG-secreted IgG-Antigen-antigen oligo-cell barcode. (ii) If the secreted IgG does not bind the antigen: Anti_IgG-secreted IgG, then no oligos contribute to the sequencing library. Finally, oligos are amplified and made into a sequencing library and sequenced.

The LIBRA-seq method can also be used in a ligand blocking assay for the identification of antibodies that can block/inhibit specific receptor-ligand interactions. In addition to oligo-tagged antigens, primer beads, and anti-IgG antibodies with a magnetic bead, an oligo-tagged ligand is added. After this, the steps are the same as described above for the magnetic bead separation: (i) If secreted IgG antibody binds the antigen but does not block ligand binding: Anti_IgG-secreted IgG-(Antigen-antigen oligo-cell barcode)+(Antigen-ligand-ligand oligo barcode-cell barcode); (ii) If secreted IgG antibody binds antigen AND blocks ligand binding: Anti_IgG-secreted IgG-Antigen-antigen oligo-cell barcode; (iii) If IgG antibody does not bind target: Anti_IgG-secretedIgG, then no oligos contribute to sequencing library.

In some embodiments, the methods herein can comprise the additional optional step of isolating antigen positive cells using fluorescence activated cell sorting.

In some embodiments, disclosed herein is an antibody or antigen binding fragment thereof comprising an amino acid sequence selected from a sequence disclosed in FIG. 4. In some embodiments, disclosed herein is an antibody or antigen binding fragment thereof comprising an amino acid sequence selected from a sequence disclosed in FIG. 5. In some embodiments, disclosed herein is an antibody or antigen binding fragment thereof comprising an amino acid sequence selected from a sequence disclosed in the Sequence section below. In some embodiments, disclosed herein is an antibody or antigen binding fragment thereof comprising an amino acid sequence selected from a CDR sequence disclosed in the Sequence section below or a CDR sequence disclosed in FIG. 4 or FIG. 5.

In some embodiments, disclosed herein is a population of single cells expressing protein or protein fragments containing an antibody variable region, including: primary cells expressing B cell receptors; mammalian cells engineered to express a protein containing an antibody variable region, such as a mammalian display library; or non-mammalian cells, such as yeast, engineered to express a protein containing an antibody variable region, such as a yeast display library.

In some aspects, disclosed herein is a method for simultaneous detection of an antigen and an antibody that specifically binds said antigen, comprising:

labeling a plurality of antigens with unique antigen barcodes;

providing a plurality of barcode-labeled antigens to a population of B-cells;

allowing the plurality of barcode-labeled antigens to bind to the population of B-cells;

optionally washing unbound antigens from the population of B-cells;

separating the B-cells into single cell emulsions or wells;

introducing into each single cell emulsion a unique cell barcode-labeled bead;

tagging cellular transcripts and antigen barcodes with bead-delivered cell barcodes;

pooling all tagged transcripts and antigen barcodes that have been tagged with bead-delivered cell barcodes;

preparing a cDNA library from the pooled mRNA and antigen barcodes that have been tagged with bead-delivered cell barcodes;

performing PCR amplification reactions to produce a plurality of amplicons, wherein the amplicons comprise: 1) the cell barcode and the antigen barcode, and 2) the cell barcode and i) an immunoglobulin heavy chain (VDJ) sequence, and/or ii) an immunoglobulin light chain (VJ) sequence; and/or ii) an immunoglobulin constant region sequence; and sequencing the plurality of amplicons.

In some aspects, disclosed herein is a method for simultaneous detection of an antigen and a secreted antibody that specifically binds said antigen, comprising:

labeling a plurality of antigens with unique antigen barcodes;

introducing a plurality of antigens with unique antigen barcodes to droplets or wells (traditional wells or microwells);

introducing a molecule capable of binding secreted antibody to each droplet or well (traditional well or microwell);

optionally, the molecule is an anti-IgG antibody;

optionally, the molecule is an anti-kappa chain antibody;

optionally, the molecule is an anti-lambda chain antibody;

optionally, the molecule is conjugated to a magnetic bead;

isolating antibody-secreting cells in single droplets or wells (traditional wells or microwells);

allowing antibody secreting cells to secrete soluble antibody;

allowing the secreted antibodies to bind any member of the plurality of antigens;

allowing the molecule capable of binding soluble antibody to bind antibodies secreted from the antibody-secreting cell;

lysing the cells;

allowing cellular transcripts and antigen barcodes to be tagged with bead-delivered cell barcodes;

isolating the complex formed from the molecule capable of binding secreted antibody and the secreted antibody;

pooling all isolated complexes;

preparing a cDNA library from the oligos contained in the pooled complexes;

performing PCR amplification reactions to produce a plurality of amplicons, wherein the amplicons comprise the cell barcode and the antigen barcode;

pooling all tagged cellular transcripts that have been tagged with bead-delivered cell barcodes; preparing a separate cDNA library from the pooled mRNA that has been tagged with bead-delivered cell barcodes;

performing PCR amplification reactions to produce a plurality of amplicons, wherein the amplicons comprise: 1) the cell barcode and i) an immunoglobulin heavy chain (VDJ) sequence, or ii) an immunoglobulin light chain (VJ) sequence; and sequencing the plurality of amplicons.

In some aspects, disclosed herein is a method for simultaneous detection of an antigen and a secreted antibody that specifically binds said antigen, as well as ligand-blocking function, comprising:

labeling a plurality of antigens with unique antigen barcodes;

labeling a ligand or plurality of ligands to any antigen in the plurality of antigens with unique ligand barcodes;

introducing a plurality of antigens with unique antigen barcodes to droplets or wells (traditional wells or microwells);

introducing a molecule capable of binding secreted antibody to each droplet or well (traditional well or microwell);

optionally, the molecule is an anti-IgG antibody;

optionally, the molecule is an anti-kappa chain antibody;

optionally, the molecule is an anti-lambda chain antibody;

optionally, the molecule is conjugated to a magnetic bead;

isolating antibody-secreting cells in single droplets or wells (traditional wells or microwells);

allowing antibody secreting cells to secrete soluble antibody;

allowing the secreted antibodies to bind any member of the plurality of antigens;

allowing the molecule capable of binding soluble antibody to bind antibodies secreted from the antibody-secreting cell;

lysing cells;

allowing cellular transcripts, antigen barcodes, and ligand barcodes to be tagged with bead-delivered cell barcodes;

isolating the complex formed from the molecule capable of binding secreted antibody and the secreted antibody;

pooling all isolated complexes;

preparing a cDNA library from the oligos contained in the pooled complexes;

performing PCR amplification reactions to produce a plurality of amplicons, wherein the amplicons comprise: (1) the cell barcode and the antigen barcode, and (2) the cell barcode and ligand barcode pooling all tagged cellular transcripts that have been tagged with bead-delivered cell barcodes;

preparing a separate cDNA library from the pooled mRNA that has been tagged with bead-delivered cell barcodes;

performing PCR amplification reactions to produce a plurality of amplicons, wherein the amplicons comprise: 1) the cell barcode and i) an immunoglobulin heavy chain (VDJ) sequence, or ii) an immunoglobulin light chain (VJ) sequence; and sequencing the plurality of amplicons.

The current technology provides a number of improvements and benefits over previous technologies. For example, the invention tags the antigen protein of interest with an arbitrary barcode and sequence as an identifier. Thus, the barcodes herein do not encode the antigen and allows use of non-proteins in the LIBRA-seq technology herein. In addition, the simple presence or absence of a cell barcode is generally not sufficient to identify antigen specificity. Thus, in some embodiments, in addition to a cell barcode, there is also a unique molecular identifier (UMI) on each bead-delivered oligo. Thus, the specificity can be determined based on the number of UMIs per cell barcode:antigen barcode pair.

EXAMPLES

The following examples are set forth below to illustrate the systems, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. High-Throughput Mapping of B-Cell Receptor Sequences to Antigen Specificity The antibody repertoire (the collection of antibodies present in an individual) is capable of efficiently responding to invading pathogens due to its exceptional diversity and ability to fine tune antigen specificity via somatic hypermutation. This antibody pool serves as a rich source of potential therapeutics, but its size makes it difficult to examine more than a small cross-section of the total repertoire. Recent advances in next-generation sequencing (NGS) enable high-throughput interrogation of antibody repertoires at the sequence level, including of paired heavy and light chains. However, annotation of observed antibody sequences for their cognate antigen partner(s) generally requires synthesis, production and characterization of individual recombinant monoclonal antibodies.

Figure 1:
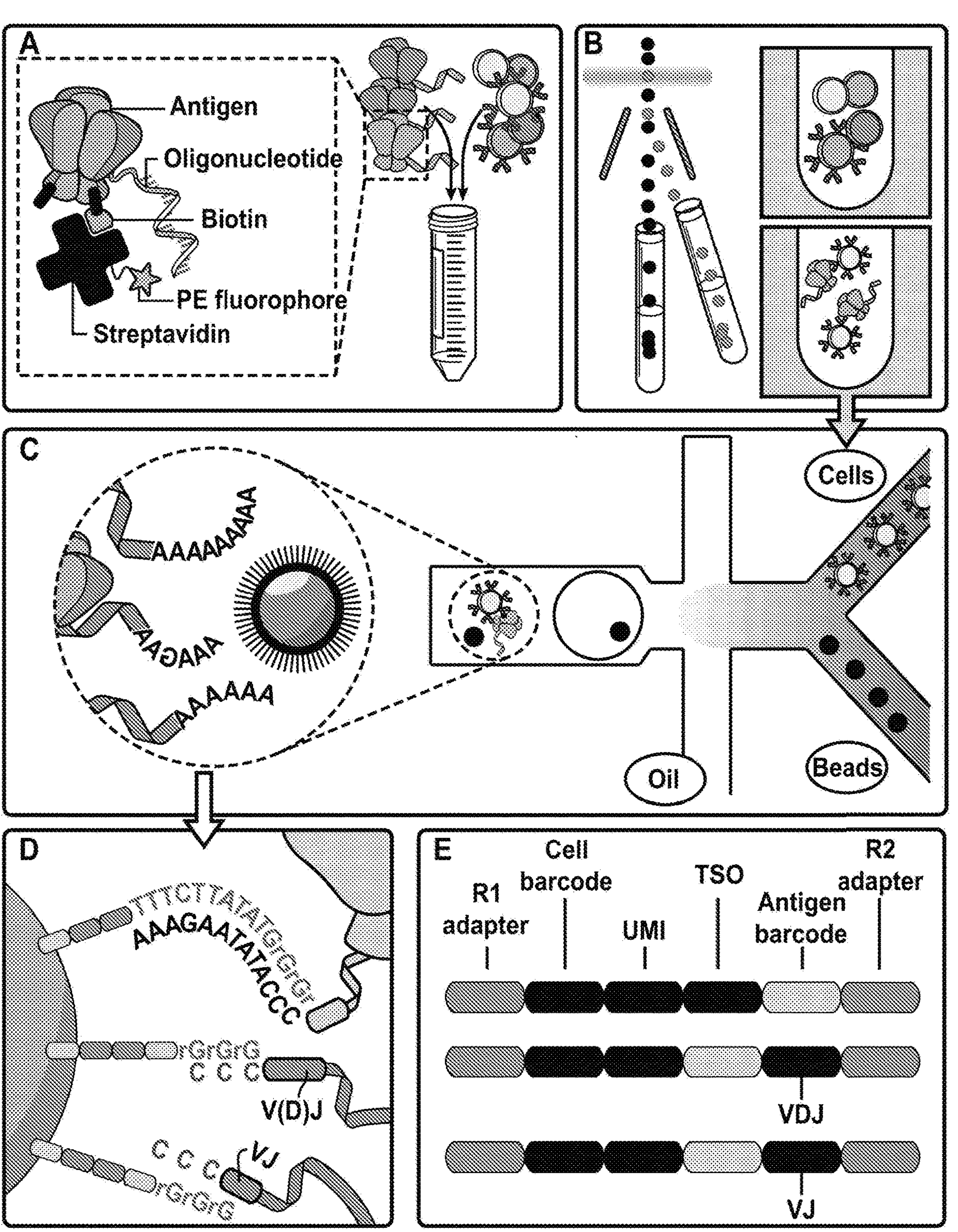
FIG. 1. LIBRA-seq assay schematic and validation. (A-E) Schematic of LIBRA-seq assay. Fluorescently-labelled, DNA-barcoded antigens (A) are used to sort antigen-positive B cells (B) before co-encapsulation of single B cells with bead-delivered oligos using droplet microfluidics (C). Bead-delivered oligos index both cellular BCR transcripts and antigen barcodes during reverse transcription (D), enabling direct mapping of BCR sequence to antigen specificity following sequencing (E). Note (A-E): elements of the depiction are not shown to scale, and the number and placement of oligonucleotides on each antigen can vary. (F-H) The assay was initially validated on Ramos B cell lines expressing BCR sequences of known neutralizing antibodies VRC01 and Fe53. (F.) Numbers of cells recovered after FACS, single cell sequencing, and LIBRA-seq computational pipeline. Cells are classified as either linked (possessing BCR sequence and high-confidence antigen mapping information) or unlinked (possessing only one of BCR sequence or high-confidence antigen mapping information). From 3466 cells, 2250 linked cells were recovered: 1295 VRC01 cells and 955 Fe53 cells. (G.) Separation of cell lines on a single principal component based on LIBRA-seq scores for the antigen screening panel: BG505, CZA97, and HA. (F.) The LIBRA-seq score for BG505 (y-axis) and CZA97 (x-axis) for each VRC01 B cell was plotted. Each axis represents the minimum to maximum LIBRA-seq score for each antigen. Density of total cells is shown, with purple to yellow indicating lowest to highest number of cells, respectively.
Figure 1:
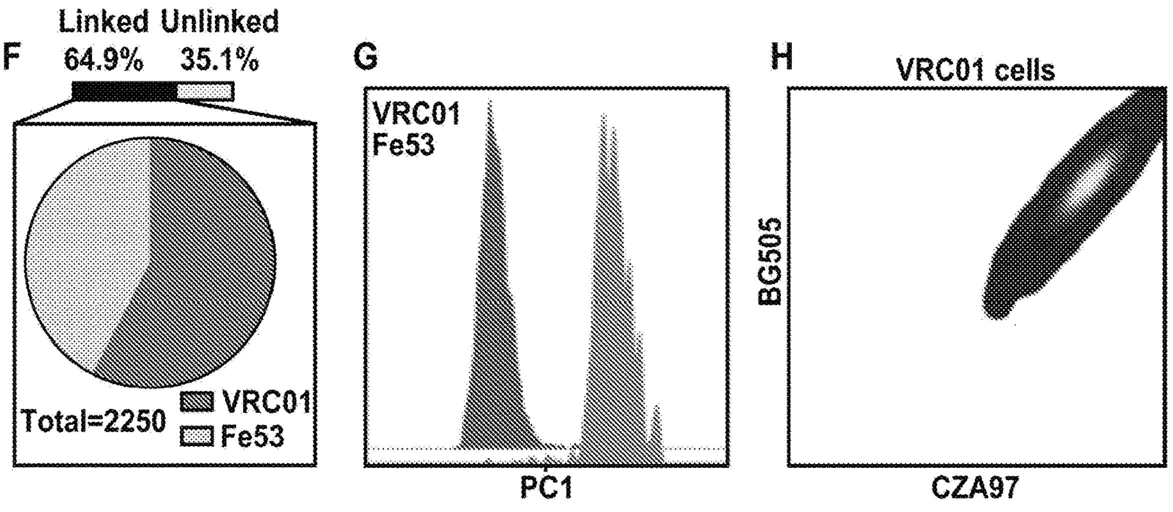

In order to recover both antigen specificity and paired heavy and light chain B cell receptor (BCR) sequence in a single, high-throughput assay, a technology named LIBRA-seq (LInking B cell Receptor to Antigen specificity through sequencing) was developed. A next-generation sequencing-based readout for BCR-antigen binding interactions was developed by conjugating oligonucleotides (oligos) to recombinant, fluorescently-labeled antigens (FIG. 1A, FIG. 3) (Methods). All antigens are labelled with the same fluorophore, which allows for sorting of antigen-positive B cells by fluorescence-activated cell sorting (FIG. 1B) before encapsulation of single B cells by droplet microfluidics (FIG. 1C). Antigen barcodes and BCR transcripts are tagged with a common cell barcode from bead-delivered oligos (FIG. 1D), enabling direct mapping of BCR sequence to antigen specificity (FIG. 1E).

To evaluate the ability of LIBRA-seq to accurately unite BCR sequence and specificity, a proof-of-principle mapping experiment was performed by utilizing two Ramos B-cell lines with differing BCR sequences and specificities. These engineered B-cell lines do not display endogenous antibody and instead express specific, user-defined surface IgM BCR sequences. To that end, two well-characterized antibodies were chosen: VRC01, a CD4-binding site-directed HIV-1 broadly neutralizing antibody (bNAb), and Fe53, a bNAb recognizing the stem of group 1 influenza hemagglutinins (HA). The two populations of B-cell lines were mixed at a 1:1 ratio and incubated with three unique DNA-barcoded antigens: the single-chain variants of the trimeric HIV-1 Env protein from strains BG505 and CZA97, and trimeric hemagglutinin from strain A/New Caledonia/07/1999, which was engineered with the Y98F mutation to prevent binding to cell-surface sialyl-oligosaccharide. 2250 cells with BCR sequence and high-confidence antigen specificity information were recovered, highlighting the high throughput potential of LIBRA-seq (FIG. 1F). For each cell, the LIBRA-seq scores for each antigen in the screening library are computed as a function of the number of unique UMIs for the respective antigen barcode; therefore, scores serve as a proxy for the amount of bound antigen (Methods). A single principle component of LIBRA-seq scores (Methods) clearly separated VRC01 Ramos B cells from Fe53 Ramos B cells, showing an ability to unambiguously delineate antigen specificity using LIBRA-seq (FIG. 1G). Further, BG505 and CZA97 scores for VRC01 Ramos B cells had a virtually perfect Pearson correlation (0.97), indicating an ability to identify cross-reactive B cells using LIBRA-seq (FIG. 1H).

Next, LIBRA-seq was used to analyze the antibody repertoire of donor NIAID 45, who had been living with HIV without antiretroviral therapy for approximately 17 years at the time of sample collection. This sample was selected as an appropriate target for LIBRA-seq analysis because a large lineage of HIV-1 bNAbs had been identified previously from this donor. This lineage consists of the prototypical bNAb VRC01, as well as multiple clades of clonally related bNAbs with diverse neutralization phenotypes, enabling the determination of whether LIBRA-seq can successfully identify antigen-specific B cells that belong to the VRC01 lineage. The same BG505, CZA97, and HA antigen screening library used in the B-cell lines experiments was utilized on cells from donor NIAID 45, leading to the recovery of paired VH:VL antibody sequences with high-confidence antigen mapping for 848 cells (FIG. 4B). These B cells exhibited a diversity of LIBRA-seq scores among the three antigens (FIG. 2A-C), as can be expected from a polyclonal sample possessing a wide variety of B cell specificities and antigen affinities. The cells displayed a few discrete patterns based on their LIBRA-seq scores; generally, cells were either (1) HAhigh Env° or (2) HA$^{10}$ wEnvhigh (FIG. 2A-B). Additionally, cells that were double positive for both HIV Env variants, BG505 and CZA97 were observed, indicating cross-reactivity of these B cells (FIG. 2C).

To further investigate the utility of LIBRA-seq in monoclonal antibody isolation, new members of the VRC01 antibody lineage were identified from the LIBRA-seq-identified antigen-specific B cells (FIG. 2D-G). 30 BCRs that clustered with previously identified antibodies in a phylogenetic tree of the VRC01 lineage were identified (FIG. 2D). All newly identified BCRs had high levels of somatic hypermutation and utilized IGHV1-2*02 along with the characteristic 5-residue CDRL3 paired with IGVK3-20 (FIGS. 2F and 2G). These B cells came from multiple clades of the known VRC01 lineage, with sequences with high identity and phylogenetic relatedness to lineage members VRC01, VRC02, VRC03, VRC07, VRC08, NIH45-46, and others (FIG. 2D). All newly discovered VRC01-lineage B cells exhibited a high LIBRA-seq signal for at least one of the two Env variants in the antigen screening library (FIG. 2E). Though scores varied by clade, VRC01 lineage members had some of the highest LIBRA-seq scores of any identified B cells for both CZA97 and BG505 (FIG. 4C), indicating that ultimately the LIBRA-seq platform can be successfully used to down-select cross-reactive bNAbs in prospective antibody discovery efforts.

Figure 5A:
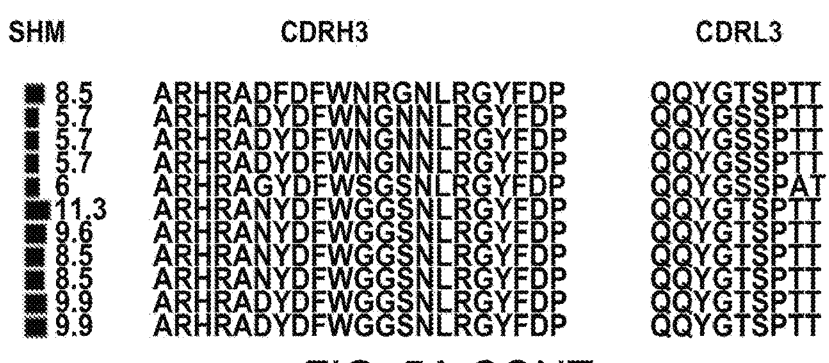
Figure 5:
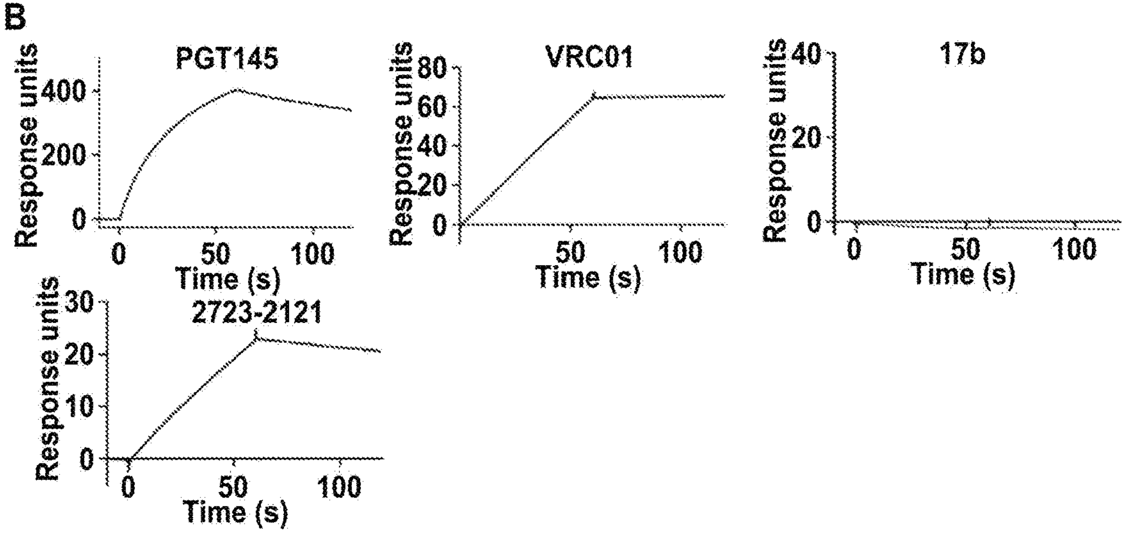

In addition to the VRC01 lineage, a number of other HIV-specific B cells with high LIBRA-seq scores for both BG505 and CZA97, or flu-specific B cells with high LIBRA-seq scores for HA, were also identified (FIG. 2A-C). To further investigate the ability of LIBRA-seq to accurately identify antigen-specific B cells, a number of monoclonal antibodies that did not belong to the VRC01 lineage were identified and characterized. In particular, 11 members of one lineage were identified, named as lineage 2121 (after antibody 2723-2121), with high LIBRA-seq scores to both BG505 and CZA97, and three representative members were recombinantly expressed (FIGS. 2H and 2I, FIG. 5A). All three antibodies bound to both BG505 and CZA97 but not HA by enzyme linked immunosorbent assay (ELISA), in agreement with the LIBRA-seq results (FIG. 2J). Antibody 2723-2121 also bound to a stabilized BG505 trimer by surface plasmon resonance (SPR)(FIG. 5B) and neutralized pseudovirus strains from a diverse global panel (FIG. 5C). To map the epitope of 2723-2121, a competition assay was performed using SPR with Fabs from bNAbs with a variety of known Env epitopes and mapped the specificity to the CD4-binding site (FIG. 5D). The ability of LIBRA-seq to identify B cells with non-HIV specificity was also confirmed by expressing and testing two antibodies with high LIBRA-seq scores for influenza HA (FIGS. 2H and 2I), each of which bound HA but not BG505 or CZA97 by ELISA, confirming the ability of LIBRA-seq to simultaneously map to multiple diverse antigen specificities.

The use of DNA-barcoded antigens allows for parallel screening of all B cells in a sample against a greater repertoire of epitopes than purely FACS-based methods, where spectral overlap limits the use of large antigen panels. LIBRA-seq therefore helps maximize antibody lead discovery per experiment, an important consideration when preserving limited sample volume. Extensions of LIBRA-seq and other applications of molecular genomics technologies to antibody discovery and immune profiling can translate into a rapid accumulation of new data, leading to insights into basic and applied immunology.

Methods and Materials

Antigen expression and purification. For the antigen screening library, HIV-1 gp140 SOSIP variants from two diverse strains: BG505 (clade A) and CZA97 (clade C) and HA from strain A/New Caledonia/20/99 (HIN1) were expressed as recombinant soluble antigens. The single-chain variants of BG505 and CZA97, each containing an Avi tag, were expressed in 293F mammalian cells using polyethylenimine (PEI) transfection reagent and cultured for 5-7 days. Next, cultures were centrifuged at 6000 rpm for 20 minutes. Supernatant was 0.45 μm filtered with Nalgene Rapid Flow Disposable Filter Units with PES membrane, and then run slowly over an affinity column of agarose bound *Galanthus nivalis* lectin (Vector Laboratories cat no. AL-1243-5) at 4° C. The column was washed with PBS, and proteins were eluted with 30 mL of 1 M methyl-α-D-mannopyranoside. The protein elution was buffer exchanged 3× into PBS and concentrated using 30 kDa Amicon Ultra centrifugal filter units. Concentrated protein was run on a Superdex 200 Increase 10/300 GL sizing column on the AKTA FPLC system, and fractions were collected on an F9-R fraction collector. Fractions corresponding to correctly folded antigen were analyzed by SDS-PAGE, and antigenicity by ELISA was characterized with known monoclonal antibodies specific for that antigen.

Recombinant HA containing the HA ectodomain with a point mutation at the sialic acid-binding site (Y98F), T4 fibritin foldon trimerization domain, Avi tag, and hexahistidine tag was expressed in Expi 293F mammalian cells using Expifectamine 293 transfection reagent (Thermo Fisher Scientific) cultured for 5 days. Culture supernatant was harvested and cleared as above, and then adjusted Ph and NaCl concentration by adding 1M Tris-HCl (pH 7.5) and 5M NaCl to 50 mM and 500 mM, respectively. Ni Sepharose excel resin (GE Healthcare) was added to the supernatant to capture hexahistidine tag. Resin was separated on a column by gravity and captured HA protein was eluted by a Tris-NaCl (pH 7.5) buffer containing 300 mM imidazole. The eluate was further purified by a size exclusion chromatography with a HiLoad 16/60 Superdex 200 column (GE Healthcare). Fractions containing HA were concentrated, analyzed by SDS-PAGE and tested for antigenicity by ELISA with known antibodies. Proteins were frozen in $LN_2$ and stored at −80° C. until use.

All antigens included an AviTag modification at the C-terminus of their sequence, and after purification, each AviTag labeled antigen was biotinylated using the BirA-500: BirA biotin-protein ligase standard reaction kit (Avidity LLC, cat no. BirA500).

Oligonucleotide barcode design Oligos were used that possess a 13 bp antigen barcode, a sequence capable of annealing to the template switch oligo that is part of the 10× bead-delivered oligos, and contain truncated TruSeq small RNA read 1 sequences in the following structure: 5'-CCTTGGCACCCGAGAATTCCANNNNNNNNNNNN NCCCATATAAGA*A*A-3' (SEQ ID NO:48), where Ns represent the antigen barcode. For both experiments, the following antigen barcodes were used: CATGATTGGCTCA (BG505) (SEQ ID NO:49), TGTCCGGCAATAA (CZA97) (SEQ ID NO:50), GATCGTAATACCA (HA) (SEQ ID NO:78). Oligos were ordered from Sigma-Aldrich with a 5' amino modification and HPLC purified.

Conjugation of oligonucleotide barcodes to antigens For each antigen, a unique DNA "barcode" was directly conjugated to the antigen itself. In particular, 5'amino-oligonucleotides were conjugated directly to each antigen using the Solulink Protein-Oligonucleotide Conjugation Kit (TriLink cat no.S-9011) according to manufacturer's instructions. Briefly, the oligo and protein were desalted, and then the amino-oligo was modified with the 4FB crosslinker, and the biotinylated antigen protein was modified with S-HyNic. Then, the 4FB-oligo and the HyNic-antigen were mixed together. This causes a stable bond to form between the protein and the oligonucleotide. The concentration of the antigen-oligo conjugates was determined by a BCA assay, and the HyNic molar substitution ratio of the antigen-oligo conjugates was analyzed using the NanoDrop according to the Solulink protocol guidelines. AKTA FPLC was used to remove excess oligonucleotide from the protein-oligo conjugates. Additionally, the antigen-oligo conjugates were analyzed via SDS-PAGE with a silver stain.

Fluorescent labeling of antigens After attaching DNA barcodes directly to a biotinylated antigen, the barcoded antigens were mixed with streptavidin labeled with fluorophore phycoerythrin (PE). The streptavidin-PE was mixed with biotinylated antigen at a 5× molar excess of antigen to streptavidin. ⅕ of the streptavidin-oligo conjugate was added to the antigen every 20 minutes with constant rotation at 4° C.

B cell lines production and identification by sequencing B cell lines were engineered from a clone of Ramos Burkitt's lymphoma that do not display endogenous antibody, and they ectopically express specific surface IgM B cell receptor sequences. The B cell lines used expressed B cell receptor sequences for HIV-1 specific antibody VRC01 and influenza specific antibody Fe53. The cells are cultured at 37° C. with 5% $CO_2$ saturation in complete RPMI, made up of RPMI supplemented with 15% fetal bovine serum, 1% L-Glutamine, and 1% Penicillin/Streptomycin. Though endogenous heavy chains are scrambled, endogenous light chain transcripts remain and are detectable by sequencing. Single Ramos Burkitt's B cells were thus identified and classified as either VRC01 or FE53 based on their heavy chain sequences. These Ramos B cell lines were validated for binding to our antigen probes by FACS (FIG. 3).

Donor PBMCs Peripheral blood mononuclear cells were collected from donor NIH45 on Jul. 12, 2007. Donor NIH45, from whom antibodies VRC01, VRC02, VRC03, VRC06, VRC07, VRC08, and NIH45-46 had been previously isolated, was enrolled in investigational review board approvedclinical protocols at the National Institute of Allergy and Infectious Diseases and had been living with HIV without antiretroviral treatment for approximately 17 years at the time of sample collection.

Enrichment of antigen-specific IgG+B cells For the given sample, cells were stained and mixed with fluorescently labeled DNA-barcoded antigens and other antibodies, and then sorted using fluorescence activated cell sorting (FACS). First, cells were counted and viability was assessed using Trypan Blue. Then, cells were washed with DPBS supplemented with 1% Bovine serum albumin (BSA) through centrifugation at 300 g for 7 minutes. Cells were resuspended in PBS-BSA and stained with a variety of cell markers including CD3-APCCy7, IgG-FITC, CD19-BV711, CD14-V500, and LiveDead-V500. Additionally, fluorescently labeled antigen-oligo conjugates (described previously) were added to the stain, so antigen-specific sorting could occur. After staining in the dark for 30 minutes at room temperature, cells were washed 3 times with PBS-BSA at 300 g for 7 minutes. Then, cells were resuspended in PBS-BSA and sorted on the cell sorter. Antigen positive cells were bulk sorted and then they were delivered to the Vanderbilt VANTAGE sequencing core at an appropriate target concentration for 10× Genomics library preparation and NGS analysis. FACS data were analyzed using Cytobank. 10× single cell processing and next generation sequencing Single-cell suspensions were loaded onto the Chromium microfluidics device (10× Genomics) and processed using the B-cell VDJ solution according to manufacturer's suggestions for a target capture of 10,000 B cells per ⅛ 10× cassette for B cell lines and 9,000 cells for B cells from donor NIH45, with minor modifications in order to intercept, amplify and purify the antigen barcode libraries. The library preparation follows the CITE-seq protocol (available at https://cite-seg.com), with the exception of an increase in the number of PCR cycles of the antigen barcodes. Briefly, following cDNA amplification using an additive primer (5'-CCTTGGCACCCGAGAATT*C*C-3') (SEQ ID NO: 79) to increase the yield of antigen barcode libraries, SPRI separation was used to size separate antigen barcode libraries from cellular mRNA libraries, PCR amplified for 10-12 cycles, and purified using 1.6× purification. Sample preparation for the cellular mRNA library continued according to 10× Genomics-suggested protocols, resulting in Illumina-ready libraries. Following library construction, both BCR and antigen barcode libraries were sequences on a NovaSeq 6000 at the VANTAGE sequencing core, dedicating 2.5% of a flow cell to each experiment, with a target 10% of this fraction dedicated to antigen barcode libraries. This resulted in ~334.5 million reads for the cell line V(D)J libraries (~96,500 reads/cell) and ~376.3 million reads for donor NIH45 V(D)J libraries (~79,300 reads/cell). Additionally, this sequencing depth resulted in ~23.3 million reads for barcode library of the cell lines, and ~19.8 million reads for the barcode library of donor NIH45.

Processing of antigen barcode reads and BCR sequence contigs. A pipeline was developed that takes paired-end fastq files of oligo libraries as input, processes and annotates reads for cell barcode, UMI, and antigen barcode, and generates a cell barcode—antigen barcode UMI count matrix. BCR contigs are processed using cellranger (10× Genomics)using GRCh38 as reference. For the antigen barcode libraries, initial quality and length filtering is carried out by fastp using default parameters for filtering. This results in only high-quality reads being retained in the antigen barcode library (~97-99% Q20 and ~93-95% Q30, FIG. 6). In a histogram of insert lengths, this results in a sharp peak of the expected insert size of 52 (FIG. 5B-C). Fastx_collapser is then used to group identical sequences and convert the output to deduplicated fasta files. Then, having removed low-quality reads, just the R2 sequences were processed, as the entire insert is present in both R1 and R2. Each unique R2 sequence was processed one by one using the following steps: (1) The reverse complement of the R2 sequence was determined. (2) The sequence was screened for possessing an exact match to any of the valid 10× cell barcodes present in the filtered_contig.fasta file output by cell ranger during processing of BCR V(D)J fastq files. Sequences without a BCR-associated cell barcode were discarded. (3) The 10 bases immediate 3' to the cell barcode were annotated as the read's UMI. (4) The remainder of the sequence 3' to the UMI is screened for a 13 bp sequence with a hamming distance of 0, 1, or 2 to any of the antigen barcodes used in the screening library. Following this processing, only sequences with lengths of 51 to 58 were retained, thus allowing for a deletion, an insertion outside the cell barcode, or bases flanking the cell barcode. This general process requires that sequences possess all elements needed for analysis (cell barcode, UMI, and antigen barcode), but is permissive to insertions or deletions in the TSO region between the UMI and antigen barcode. After processing each sequence one-by-one, cell barcode-UMI-antigen barcode collisions were screened for. Any cell barcode-UMI combination (indicative of a unique oligo molecule) that had multiple antigen barcodes associated with it was removed. A cell barcode-antigen barcode UMI count matrix was then constructed, which served as the bases of subsequent analysis. Additionally, the BCR contigs were aligned (filtered_contigs.fasta file output by Cellranger, 10× Genomics) to IMGT reference genes using IgBLAST. The output of IgBLAST is parsed using ChangeO, and merged with the UMI count matrix.

Determination of LIBRA-seq Score Starting with the UMI count matrix, the matrix was subset to contain only cells possessing at least 5 total UMI counts across all three antigens so as to increase confidence in our measurements of binding signal. These were referred as cells with "high-confidence" antigen mapping. Then log(1+×) was calculated using the log 1p function in numpy for each UMI count, where x is the number of UMIs for a given antigen barcode for a given cell. Because UMI counts were on different scales for each antigen, possibly due to differential oligo loading during oligo-antigen conjugation as revealed by the different MSRs (supplement), the logarithmic UMI counts were rescaled from 0 to 1 using the MinMaxScaler method in scikit learn to arrive at the final LIBRA-seq scores. LIBRA-seq scores were visualized using Cytobank.

Phylogenetic trees Phylogenetic trees of antibody heavy chain sequences were constructed in order to assess the relative relatedness of antibodies within a given lineage. For the VRC01 lineage, the 30 sequences identified by LIBRA-seq and 52 sequences identified from the literature were aligned using clustal within Geneious. The PhyML maximum likelihood plugin in Geneious were used (available at https://www.geneious.com/plugins/phyml-plugin/) to infer a phylogenetic tree. The resulting tree was then rooted to the inferred unmutated common ancestor (accession MK032222). A similarprocess was used to build a phylogenetic tree for lineage 2121, with one exception. Rather than using an inferred germline precursor, the $V_H$ and $J_H$ genes were germline reverted and the CDRH3 nucleotide sequence of the lineage member with the least $V_H$ somatic mutation was used.

Antibody expression and purification For each antibody, variable genes were inserted into plasmids encoding the constant region for the heavy chain (pFUSE-CHIg, Invivogen) and light chain (pFUSE2-CLIg, Invivogen) and synthesized from GenScript. In cases where the IgBLAST-aligned sequence was missing any residues at the beginning of framework 1 or end of framework 4, sequences were completed with germline residues. mAbs were expressed in Expi 293F mammalian cells by co-transfecting heavy chain and light chain expressing plasmids using polyethylenimine (PEI) transfection reagent and cultured for 5-7 days. Next, cultures were centrifuged at 6000 rpm for 20 minutes. Supernatant was 0.45 μm filtered with Nalgene Rapid Flow Disposable Filter Units with PES membrane. Filtered supernatant was run over a column containing Protein A agarose resin that had been equilibrated with PBS. The column was washed with PBS, and then antibodies were eluted with 100 mM Glycine HCl at pH 2.7 directly into a 1:10 volume of 1 M Tris-HCL pH 8. Eluted antibodies were buffer exchanged into PBS 3 times using 10 kDa Amicon Ultra centrifugal filter units.

Enzyme linked immunosorbent assay (ELISA) For direct ELISAs, soluble hemagglutinin protein was plated at 2 g/ml overnight at 4C. The next day, plates were washed three times with PBS supplemented with 0.05% Tween20 (PBS-T) and coated with 5% milk powder in PBS-T. Plates were incubated for one hour at room temperature and then washed three times with PBS-T. Primary antibodies were diluted in 1% milk in PBS-T, starting at 10 g/ml with a serial 1:5 dilution and then added to the plate. The plates were incubated at room temperature for one hour and then washed three times in PBS-T. The secondary antibody, goat anti-human IgG conjugated to peroxidase, was added at 1:20,000 dilution in 1% milk in PBS-T to the plates, which were incubated for one hour at room temperature. Plates were washed three times with PBS-T and then developed by adding TMB substrate to each well. The plates were incubated at room temperature for ten minutes, and then 1 N sulfuric acid was added to stop the reaction. Plates were read at 450 nm. Recombinant trimer capture for BG505 or CZA97 single chain SOSIP, 2 g/ml of a mouse anti-AviTag antibody (GenScript) was coated overnight at 4C in phosphate-buffered saline (PBS) (pH7.5). The next day plates were washed three times with PBS-T, and blocked with 5% milk in PBS-T. After an hour incubation at room temperature and three washes with PBS-T, 2 g/ml of recombinant trimer proteins diluted in 1% milk PBS-T were added to the plate and incubated for one hour at room temperature. Primary and secondary antibodies, along with substrate and sulfuric acid, were added as described above. ELISAs were performed in at least two experimental replicates and data were graphed using GraphPad Prism 8.0.0. Data shown is representative of one replicate, with error bars representing standard error of the mean for technical duplicates within that experiment.

TZM-bl Neutralization Assays Antibody neutralization was assessed using the TZM-bl assay as described. This standardized assay measures antibody-mediated inhibition of infection of JC53BL-13 cells (also known as TZM-bl cells) by molecularly cloned Env-pseudoviruses. Viruses that are highly sensitive to neutralization (Tier 1) and those representing circulating strain that are moderately sensitive (Tier 2) were included. Antibodies were tested against 3 Tier 1 viruses and the Tier 2 Global panel plus BG505 and ZA097 (antigens used in B cell sorting). Murine leukemia virus (MLV)was included as an HIV-specificity control and VRC01 was used as a positive control. Results are presented as the concentration of monoclonal antibody (in μg/ml) required to inhibit 50% of virus infection (IC50).

Surface Plasmon Resonance and Fab competition The binding of antibody 2723-2121 to BG505 DS-SOSIP was assessed by surface plasmon resonance on Biacore T-200 (GE-Healthcare) at 25° C. with HBS-EP+ (10 mM HEPES, pH 7.4, 150 mM NaCl, 3 mM EDTA, and 0.05% surfactant P-20) as the running buffer. Antibodies VRC01 and PGT145 were tested as positive control, and antibody 17b was tested as negative control to confirm that the trimer was in the closed conformation. Antibody 2723-2121 was captured on a flow cell of CM5 chip immobilized with ~7500 RU of anti-human Fc antibody, and binding was measured by flowing over a 200 nM solution BG505-DS SOSIP in running buffer. Similar runs were performed with VRC01, PGT145 and 17b IgGs. To determine the epitope of antibody 2723-2121, 2723-2121 IgG was captured on a single flow cell of CM5 chip immobilized with ~7500 RU of anti-human Fc antibody. Next 200 nM BG505 DS-SOSIP, either alone or with different concentrations of antigen binding fragments (Fab) of VRC01 or PGT145 or VRC34 was flowed over the captured 2723-2121 flow cell for 60 s at a rate of 10 μl/min. The surface was regenerated between injections by flowing over 3M $MgCl_2$ solution for 10 s with flow rate of 100 μl/min. Blank sensorgrams were obtained by injection of same volume of HBS-EP+ buffer in place of trimer with Fabs solutions. Sensorgrams of the concentration series were corrected with corresponding blank curves.

Statistics ELISA error bars (standard error) were calculated using GraphPad Prism version 8.0.0. The Pearson's r value comparing BG505 and CZA97 LIBRA-seq scores for Ramos B-cell lines was calculated using the SciPy pearsonr function in python.

Example 2. Mapping of the Target Epitope of a Given HIV-Specific B Cell

In some cases, antibody discovery efforts may target the identification of particular epitope specificities (e.g., CD4-binding site, V1V2, V3-glycan, fusion peptide etc.). Further, substantial effort in the field have focused on developing technologies for characterizing the different types of antibody specificities that are present in polyclonal antibody responses to infection or vaccination. None of these technologies, however, can provide simultaneous information about both antibody sequence and target epitope for B cells in a polyclonal sample. In contrast, LIBRA-seq technology herein enables B-cell epitope mapping simultaneously with BCR sequence determination. This technology is referred as LIBRAE-seq (LIBRA with Epitope mapping through sequencing). There are numerous important applications of LIBRAE-seq, such as for understanding the immunodominant regions of a vaccine candidate by determining the epitopes targeted by B cells in polyclonal responses to immunization with that vaccine candidate. Technology benchmarking was first performed by using B-cell lines with known BCR sequence and antigen/epitope specificity, followed by validation on real HIV-1 vaccine samples.

Benchmarking LIBRAE-Seq Epitope Mapping Performance Using B-Cell Lines.

Combinations of experimental variables: The sequencing experiments explore the effect of several variables on the ability of LIBRAE-seq to recover matched B-cell receptor (BCR) sequence and epitope specificity information.

B-cell lines: B cells expressing on their surface the BCRs for the following well characterized human antibodies are used (each cell line is associated with its own unique BCR sequence): a set of antibodies targeting several different epitopes on HIV-1 Env (VRC01, PGT128, PGT145, VRC34, 10E8, 447-52D), a set of antibodies targeting different epitopes on influenza HA (Fe53, CH65), an antibody against the RSV F protein (D25), and an antibody against the human vascular endothelial growth factor (VEGF) protein (Bevacizumab). The BCRs corresponding to these antibodies result in a total of 10 B-cell lines to be used for method benchmarking.

Antigen barcoding strategy: Each of the three strategies is evaluated as described in Example 1.

Fluorescent labeling, antigen amounts, B-cell ratios, and reagent and barcode variation: These variables are evaluated as previously described in Example 1.

Antigen screening library: The same antigens previously described are included in this experiment as well. In order to be able to perform antibody epitope mapping at the residue level, the antigen screening incorporates antigen variants with epitope-specific knockout mutations. To that end, epitope-specific knockout mutations are introduced into the background of the different HIV antigens from the library. These extended antigen screening libraries enable detection of the epitopes for the six HIV B-cell lines. In particular, a B cell can recognize all variants of the same antigen, except for the variants that incorporate mutations within the epitope for that B cell. For example, the VRC01 B cells should recognize all BG505 SOSIP variants, except for variants with mutations within the VRC01 epitope, such as D368R.

In essence, while the experiments mentioned above (Benchmarking LIBRA-seq performance using B-cell lines) detect presence of B cell-antigen recognition, these experiments detect lack of recognition. Hence, there are several considerations that are taken into account when designing the sets of epitope-specific antigen variants: (i) Number of antigen backgrounds for epitope-knockout mutations: Initial studies are performed in the BG505 SOSIP background, followed by other HIV antigens as background. (ii) Number of antigen variants in screening library: Three set sizes are tested: small (~10 epitope-knockout mutations), medium (~30), and large (~100) per antigen background. The small set includes standard knockout mutations, such as N160K, N332A, D368R, etc., that are known to affect the HIV B cells used in these experiments. For the medium and large sets, computational protein design is used to select mutations that are exposed on the antigen surface and that together optimize the coverage of antigen surface; this can be achieved by applying the OSPREY protein design software suite. (iii) Choice of mutation types: Two different approaches are applied. Initially, an Ala scanning approach is used. The naturally occurring antigen sequence variation at the set of target residue positions is used in the screening library, in combination with OSPREY, in order to pick optimal mutations for each residue position. Mutations from the different approaches can also be combined to allow for multiple mutation types per residue position.

Validation of LIBRAE-Seq Epitope Mapping Using HIV Vaccine Samples

The B-cell line experiments are used for technology benchmarking of the LIBRAE-seq technology. Primary human B-cell samples from the HVTN 097 study are screened. Monoclonal antibodies corresponding to the BCRs from antigen-specific B cells are synthesized, produced, and characterized for binding to the target antigens. Application of LIBRAE-seq to HIV-1 vaccine confirms that the technology can work with real human B cells. To identify antibodies with properties of interest beyond validation of the LIBRAE-seq, additional antibody characterization is performed. The following experimental setup is used:

LIBRAE-seq configuration: The preferred LIBRAE-seq experimental variables (antigen barcoding strategy, fluorescent strategy, etc.) determined from the B-cell line experiments are used in human B-cell experiments.

B-cell samples: Eight donors from the HVTN 097 cohort are analyzed (both women and men), at one year post vaccination, with 30 million PBMC per sample.

Antigen screening library: Epitope-knockout mutations are screened in the background of monomeric gp120 from strains A244 (clade E) and MN (clade B), the protein immunogens used in the HVTN 097 study. These experiments map the antibody sequences and epitope specificities elicited by the donors studied here in response to these immunogens. The 10 antigens used for the B-cell line experiments are also included as controls and for consistency.

Monoclonal antibody selection and validation: Up to 5 monoclonal antibodies per donor, for a total of up to 40 antibodies are selected. Antibodies are selected, so that the representation of diverse Env epitopes is increased. This confirms that LIBRAE-seq can successfully identify antibodies against different vaccine epitopes. Antibodies are tested in functional assays with the addition of epitope mapping experiments, in order to be able to validate the epitope specificities predicted by LIBRAE-seq. For antibody epitope mapping, standard mapping techniques are applied, such as binding competition with monoclonal antibodies, neutralization or binding of Env variants containing epitope-specific knockout mutations, and neutralization blocking by epitope-specific antigens. In addition, the neutralization fingerprint (NFP) epitope mapping approach is applied.

Example 3. Application of LIBRA-Seq to the Characterization of Antigen-Specific Human B-Cell Repertoires The applications of the LIBRA-seq technology are far-reaching, with significant implications for the fields of therapeutic antibodies and antibody-based vaccine development. Within an individual, LIBRA-seq can lead to a detailed understanding of the antigen-specific B-cell repertoire, with the capacity to trace repertoire development over time, in response to a person's history of infection and vaccination, and as a result of biological and environmental factors, such as aging and geographical location. More generally, LIBRA-seq enables the high-throughput mapping of antibody sequence to antigen specificity, thus providing the basis for building a human antibody-antigen atlas at an unparalleled scale. Here, LIBRA-seq is applied to characterize the B-cell repertoires of 30 individuals against a large set of common and biomedically important antigens, to begin building an antibody-antigen atlas. These results also provide invaluable information about the repertoire composition of a large number of individuals.

Application of LIBRA-Seq to Characterize the Antigen-Specific Antibody Repertoires of a Large Number of Individuals Against a Large Set of Common and Biomedically Important Antigens LIBRA-seq configuration: The human B-cell sequencing experiments are performed. The optimal LIBRA-seq experimental variables (antigen barcoding strategy, fluorescent strategy, etc.) determined from the B-cell line experiments are used.

B-cell samples: The repertoires for a total of 30 individuals are examined. Leukapheresis samples are purchased from Stemcell Technologies. The use of leukapheresis samples are important for the identification of large sets of antigen-specific B cells from each sample, given the relatively low frequency of such cells. All samples are from healthy donors, generally with available infection and vaccination histories.

Antigen screening library: The library includes antigens associated with common infections and vaccinations, as well as a selection of other antigens of biomedical significance, with a summary shown in Table 1. A total of 90 antigens, representing multiple antigenic proteins as well as multiple strains from 19 pathogens are included. This antigen library incorporates some of the major antigenic targets for the selected pathogens. All of these antigens have been successfully produced in a recombinant soluble form, making them an appropriate target for the LIBRA-seq screening library.

TABLE 1

Antigen screening library for human B-cell sample analysis. For a set of pathogens, shown are selected protein targets, number of strains, and resulting total number of antigens in the screening library.

| Pathogen | Protein targets | # Strains | # Antigens in library |
|---|---|---|---|
| CMV | gB | 2 | 2 |
| Dengue | E, prM | 5 | 10 |
| Hepatitis B | HBsAg | 2 | 2 |
| Hepatitis C | E2, E1E2 | 2 | 4 |

TABLE 1-continued

Antigen screening library for human B-cell sample analysis. For a set of pathogens, shown are selected protein targets, number of strains, and resulting total number of antigens in the screening library.

| Pathogen | Protein targets | # Strains | # Antigens in library |
|---|---|---|---|
| HIV-1 | gp140, gp120, MPER | 3 | 9 |
| HPV | L1 | 3 | 3 |
| HSV-1 | gB | 1 | 1 |
| Influenza | HA, NA | * | 12 |
| Malaria | PfCSP | 1 | 1 |
| Measles | H, F | 1 | 2 |
| Mumps | HN, NP | 1 | 2 |
| Norovirus | P | 10 | 10 |
| Rhinovirus | VP1 | 5 | 5 |
| Rotavirus | VP7, VP4 | ^ | 8 |
| RSV | F, G | 4 | 8 |
| Rubella | E1 | 1 | 1 |
| *Staphylococcus aureus* | HtsA, SirA, IsdB, SstD | 1 | 4 |
| UPEC | Hma, IutA, FyuA, IreA | 1 | 4 |
| Zika | E, prM | 1 | 2 |

*influenza: A (6 HA, 4 NA) and B (2 HA); ^rotavirus: 6 G, 2 P variants)

Monoclonal antibody selection and validation: Select monoclonal antibodies corresponding to the BCRs from antigen-specific B cells are synthesized, produced, and characterized for binding to the target antigens, to confirm accurate antigen specificity identification by LIBRA-seq. Antibodies are selected to increase the diversity of antigen specificities that are validated, and are picked from several different categories: (a) strong recognition of a target antigen (as evidenced by LIBRA-seq scores); (b) cross-reactive recognition of multiple variants (strains) of a target antigen; (c) cross-reactive recognition of multiple different antigens (from different pathogens). The panels of antigens for which the selected antibodies are tested for binding are based on the LIBRA-seq scores, and include the predicted antigen binders for a given antibody, as well as a set of negative control antigens that were predicted by LIBRA-seq not to be recognized by these antibodies. These experiments help confirm the LIBRA-seq accuracy of correctly identifying antibody-antigen specificities.

Antibody production: Selected antibody sequences are cloned into the expression vectors pFUSEss-CHIg-hG1 (heavy), pFUSE2ss-CLIg-hK (kappa light), and pFUSE2ss-CLIg-hL2 (lambda light). 293F cells are co-transfected with plasmids expressing matched pairs of heavy and light chain genes. Recombinant antibodies are purified on a protein A affinity column.

Binding assays: Standard ELISA techniques are used to measure binding of each isolated monoclonal antibody to the respective antigen panel. 2 μg/mL of each protein construct is plated overnight on Nunc Immuno plates followed by blocking, and incubation with threefold serial dilutions of primary antibody starting at 20 μg/mL. Binding is detected by HRP-conjugated anti-human IgG secondary. Data are reported as absorbance at 450 nm. To determine antibody-antigen affinities, biolayer interferometry on an Octet Red 96 instrument is used.

Example 4. Delineation of Residue-Level Epitope of BCRs Through an NGS-Based Readout The ability to map single B cells to their antigen specificity in a highly parallel manner was demonstrated though a sequencing-based readout. To do this, each member of a panel of recombinant antigens is labeled with a unique DNA barcode, followed with incubation with a B cell population of interest, preparation of single-cell sequencing libraries using droplet microfluidics, and utilization of custom bioinformatics to map antigen DNA barcodes to VDJ sequences. While this allows identification of antigen specificity of each BCR sequence, this provides no information about where on the antigen a BCR binds. Knowledge of precise epitope of each antibody can enable prioritization of antibody leads and greatly accelerate discovery of antibodies with target properties.

A panel of residue knock-outs (mutations at specific target residue positions that aim at disrupting binding to B cells that recognize an epitope that includes these residue positions) of an antigen(s) of interest are produced and each is tagged with a unique DNA barcode. The LIBRA-seq assay and sequencing are performed as previously described. During data analysis, a reduction in LIBRA-seq scores (which are a function of the number of unique molecular identifiers for a given antigen variant, see below) for a particular residue/epitope knock-out compared to other variants indicates that binding of the corresponding antibody was affected by that residue.

The number of unique UMIs (unique molecular identifiers) for each combination of cell barcode/antigen barcode was determined using a custom bioinformatics pipeline. A cell-wise normalization was performed by taking the centered log ratio and the normalized values were transformed antigen-wise such that the lowest value of each antigen is 0 and the highest value is 1. This final value is referred to as the LIBRA-seq score. Epitope mapping accuracy was determined as the ratio of the number of VRC01 cells for which the D368 LIBRA-seq score was lower than all other BG505 variants.

A panel of single-residue knock-outs of the HIV antigen BG505.SOSIPsc.T332N, including BG505.SOSIPsc.T332N.N160K, BG505.SOSIPsc.T332N.K169E, BG505.SOSIPsc.T332N.D368R, as well as an unrelated antigen—the hemagglutinin of influenza strain New Caledonia 1999—was used as the screening library. Each member was tagged with a unique DNA barcode and mixed with an 80/20 mixture of VRC01 and Fe53 Ramos B cell lines, respectively. The feasibility of mapping VRC01 cells to the CD4 binding site (the known epitope of VRC01) was determined. 7046 total cells with mapped antigen specificity and a functional VDJ sequence were recovered. These clearly separated into VRC01 and Fe53 clusters based on their LIBRA-seq scores. VRC01 cells had a reduction in LIBRA-seq score for D368R compared to the other BG505 antigen variants for 5318 out of 5593 VRC01 cells (95% accuracy) (FIG. 10).

Residue-level epitope information for thousands of single B cells can be determined in a highly parallelized manner with high accuracy via LIBRA-seq by using custom antigen screening libraries.

Example 5. Screening Single B Cells from Immunized Mice for Therapeutic Antibody Discovery In some cases, antibody discovery efforts can target the identification of antibodies cross-reactive to multiple distinct protein sequences, and/or non-reactive to other distinct protein sequences. For example, antibody discovery efforts can seek molecules (1) cross-reactive to protein homologs in multiple species, to allow for pre-clinical and clinical studies with the same molecule, (2) cross-reactive to multiple allelic variants of a particular protein, (3) non-reactive to certain proteins that could cause deleterious off-target effects, or (4) any combination of (1), (2), and (3). This necessitates the ability to screen against many proteins simultaneously. LIBRA-seq is able to incorporate all these desired properties into the initial screening step.

A wild type mouse or transgenic mouse engineered to possess human antibody genes is immunized with a protein against which a therapeutic antibody is desired. For example, a mouse may be immunized with 2 allelic variants of a human protein, and the corresponding mouse and cynomolgus macaque protein homologs. In some cases, the immunogen may need to be engineered in order to elicit an antibody response against a protein from the same species, such as by including an immunogenic T-cell epitope to enable breaking of B cell tolerance (such as in MAbs. 2015; 7(1):129-37. doi: 10.4161/19420862.2014.985489). While each individual protein in the immunization scheme is likely to elicit a protein-specific antibody response, few are likely to be cross-reactive against all protein variants. Further, it is not possible with current methods to screen against all variants simultaneously.

Using LIBRA-seq, each of the 2 human allelic variants, the mouse homolog, and the cynomolgus macaque homolog can be labeled with unique barcodes. Following the mouse immunization scheme, the mouse spleen can be harvested and serve as the source of B cells for a LIBRA-seq experiment. Following sequencing, the monoclonal antibodies positive for all desired protein variants can be identified, produced as recombinant antibodies, and used in pre-clinical animal models.

Example 6. Antibody Engineering Through Screening Variants of a CDRH3 Deep Mutational Scanning Library Displayed in a Mammalian Display System After initial discovery of a candidate therapeutic antibody, the candidate molecule often requires subsequent optimization in order to improve one or more parameters, such as affinity, immunogenicity, solubility, or others. While scanning potential mutations to a candidate molecule, it is important to maintain the characteristics of the initial discovery campaign goals, such as those noted in Example 5.

After discovering a candidate therapeutic antibody, by screening B cells using LIBRA-seq or otherwise, a mammalian display library containing a large repertoire of mutations to the $3^{rd}$ complementary determining region of the heavy chain (CDRH3), or any other complementary determining region, can be constructed (such as in Mason et al, *Nucleic Acids Research*, Volume 46, Issue 14, 21 Aug. 2018, pages 7436-7449, https://doi.org/10.1093/nar/gky550). LIBRA-seq can then be performed on the resulting library, and a comprehensive list of mutations that still meet the original antibody discovery goals (ie, species cross-reactivity, etc) can be compiled. Some or all of these candidates can be expressed as recombinant antibodies and further developed, such as in immunogenicity studies, biophysical studies, or animal models. Additionally, using the data acquired from the LIBRA-seq experiment, data science/machine learning approaches can be used to identify the precise sequence determinants of optimizing the original antibody discovery goals (ie, species cross-reactivity, etc). Using the identified determinants, an in silico sequence library can be screened to identify additional candidate sequences that were not in the mammalian display library. These sequences can be expressed as recombinant antibodies and functionally validated.

SEQUENCES

>422.hc (SEQ ID NO: 1)

QFQLQESGPGLVKPSQTLSLTCVVSGGSIGTTDHYWGWIRQSPGKGLEWIGTTYYSGKT
YYNPSLNSRVTIAIDTSKNQFSLRLISVTAADTAVYHCARHRANYDFWGGSNLRGYFDP
WGRGTLVTVSS

>422.lc (SEQ ID NO: 2)

EIVLTQSPGILSLSPGDSASFSCRASQRISSYNLAWYQLKPDQAPRLLVHGTSNRATGIPD
RFSGSGSGTDFTLTISRLEPEDFAVYFCQQYGTSPTTFGPGTKVDFR

>2304.hc (SEQ ID NO: 3)

QFQLQESGPGLVKPSETLSLTCIVSGGSIDTTDHYWGWIRQSPGKGLEWIGTSYYSGKTY
YNPSLSGRVTISIDTSKNHFSLRLISVTAADTAVYHCARHRADYDFWGGSNLRGYFDPW
GRGTLVTVSS

>2304.lc (SEQ ID NO: 4)

EIVLTQSPGIMSLSPGDSASFSCRASQRISSYNLAWYQHKPDQAPRLLIYGTSNRATGIPD
RFSGSGSGTDFTLTISRLEPEDFAVYFCQQYGTSPTTFGPGTKVDFR

>1952.hc (SEQ ID NO: 5)

QVQLQESGPGLVKPSETLSLTCSISSRYLTVRSGTYWAWVRQSPGKGLEWIGSISQSGTT
YHSPSLKNEITISLDTSNNQIFLKLTPVTAADTAFYYCATRGIAASGFYFQHWGRGTLVSI
SS

>1952.1c (SEQ ID NO: 6)

DIQMTQSPSTLSASVGDKVTITCRASQSVGSSLAWYQQKPGRGPQLLISKASIIQSGVPS
RFSGGGSGTDFTLTINNLQPDDLATYYCHHYNSFSHTFGQGTKVEFK

-continued

>3196.hc (SEQ ID NO: 7)

QVQMVQSGAEMKKPGSSVKVSCKASGASWSHYAVNWVRQAPGQGLEWMGGVIPAF
NVINYAQKFQGRVTISTDESTTTVFLEVKSLKSDDTANYYCVGRQKYISGNVGDFDFWG
QGTMIIVSS

>3196.lc (SEQ ID NO: 8)

DIQMTQSPSSLSLSIGERVTITCQASQGISNYLNWYQQKPGKAPKLLIYDASNLETGVSSR
FSGSGSGTHFTFTISNLQAEDAGTYYCQQYTNLPPALNFGGGTKVEIR

>432.hc (SEQ ID NO: 9)

EAQLLESGGGLVQPGGSLRLSCEASGFSFNMYGMSWVRQGPGKGLEWVAFVSGNSDK
RDYEDSVKGRFTISRDNSNKRLYLQMNGLRGEDTATYFCARDEVLRGSASWFLGPNEV
RHYGMDVWGRGTTVVVSS

>432.lc (SEQ ID NO: 10)

DIVLTQTPPSLSVIPGQSASISCRSSQSLLNSDQQRTYLSWFLQKPGQSPQL-
LIFDVSSRFS
GVPDRFSGSGAGRDFTLKISRVEAGDAGIYYCMQSLQLRSFGQGTKLEIR

>3415.hc (SEQ ID NO: 11)

QVLLVQSGAEVKKPGASVKVSCKTSGYTFNSYGISWVRQAPGQGLEWMGWISAYRGE
TKYAQNFQGRLTMTTDTSTNTAYMELRTLTSDDTAVFYCARGRVYSDYWGQGTPVTV
SS

>3415.lc (SEQ ID NO: 12)

EIVLTQSPGTLSLSPGERATLSCRAGQSINIGYLAWYQQKPGQPPRLLIYATSNRATDIPD
RFSGSGSGTDFTLTISRLEPEDFAVYYCQQSGTSPPWTFGQGTKVEIK

>2120.hc (SEQ ID NO: 13)

QVQLLESGPGLVKPSQTLSLTCTVSGGSINSGSYYWTWIRQSAGKGLEWIGNIFPTGRTN
YSPSFKSRVFISRDTSKNQFSLTLTSMTVADTAVYHCAREHTMIFGVAEGFWFDPWGQG
TLVTVSS

>2120.lc (SEQ ID NO: 14)

PSKLTQDPVMSVALGQTVKITCRGDSLRTYYASWYQQKPGQAPLLLIYGKNSRPSGISG
RFSGSTSGNPASLTITGAQAEDEADYYCSSRDTDDISVIFGGGTKLTVL

>2859.hc (SEQ ID NO: 15)

QVQVVQSGAEVKKPGSSVRVSCKASGGLFRSHAVSWVRQAPGQGLEWMGGIVALFGT
TNYAQKFQDRVTITADESTNTVYLELNSLRSDDTAMYYCVTMSGYHVSNTYLDAWGQ
GTLVTVSS

>2859.lc (SEQ ID NO: 16)

EIVLTQSPGTLSLSPGERATLSCRASQSISSNYLAWYQQKPGQAPRLLIYGASARATGIPD
RFSGSGSGTDFTLTISRLEPEDFAVYFCQQYANSPLTFGGGTKVDIK

>2121.hc (SEQ ID NO: 17)

QVQLQESGPGLLKTSETLSLSCVVSGVSVSSSNHYWGWVRQTPGRGLEWIATVYSSGK
TYFNPSLKSRVIISVDTSNNQFSLKMTSLTVADTAVYYCARHRADYDFWNGNNLRGYF
DPWGQGALVTVSS

>2121.lc (SEQ ID NO: 18)

EIVLTQSPGTLSVSPGERATLSCRPSQTFTNTNLAWYQQKPGQAPRLLIYGASSRATGVP
DRFSGSRSGTDFTLTISRLEPEDFAIYYCQQYGSSPTTFGPGTKVDMK

>2723-3131.hc (SEQ ID NO: 19)

SQALVQSGSQMKKPGDSVRLSCQTSDSAITKYFIHWIRQAPGKGLEWIAWISPYGGGVN
YGWQVRDRATLTRNIHMETIYFDLRGLRPDDTATYYCAMRDYCRDDSCNIWDLRHWG
QGSLIVVSA

>2723-3131.lc (SEQ ID NO: 20)

AVMLTQSPGTLSLSPGDRSTLLCRASQGIGNELAWYQQKRGQTPRLIVYGASQRAPGVP
DRFGGSVSGSDFTLIINRLETEDFAFYFCQHRETFGPGTKLDLK

The sequences in this section above are from donor NIH45. A single LIBRA-seq was run on a PBMC sample from NIH45, and 848 antibodies were recovered for which there were functional heavy and light chains with a high confidence in the antigen specificity. A number of these antibodies were made recombinantly and were further characterized. A shared number in the sequences above means that the sequences are a native pairing, and hc/lc indicates heavy chain or light chain.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method for simultaneous detection of an antigen and an antibody that specifically binds said antigen, comprising:

labeling a plurality of antigens with unique antigen barcodes, wherein the plurality of antigens comprises multiple different antigenic proteins;

providing a plurality of barcode-labeled antigens to a population of B-cells;

allowing the plurality of barcode-labeled antigens to bind to the population of B-cells;

washing unbound barcode-labeled antigens from the population of B-cells;

separating the population of B-cells into single cell emulsions;

introducing into each single cell emulsion a unique cell barcode-labeled bead;

tagging cellular transcripts and the unique antigen barcodes with a bead-delivered cell barcodes;

pooling all tagged transcripts and the unique antigen barcodes that have been tagged with the bead-delivered cell barcodes;

preparing a cDNA library from the pooled tagged transcripts and the unique antigen barcodes that have been tagged with the bead-delivered cell barcodes;

performing PCR amplification reactions to produce a plurality of amplicons, wherein the amplicons comprise: 1) the bead-delivered cell barcode and the unique antigen barcode, and 2) the bead-delivered cell barcode and i) an immunoglobulin heavy chain (VDJ) sequence, or ii) an immunoglobulin light chain (VJ) sequence; and sequencing the plurality of amplicons;

to identify the unique antigen barcodes and the immunoglobulin heavy chain or light chain sequences with the bead-delivered cell barcode.

2. The method of claim 1, wherein the barcode-labeled antigens are labeled with a first barcode comprising a DNA sequence or an RNA sequence.

3. The method of claim 1, wherein the cell barcode-labeled beads are labeled with a second barcode comprising a DNA sequence or an RNA sequence.

4. The method of claim 1, wherein the barcode-labeled antigens comprise an antigen from a pathogen or an animal.

5. The method of claim 4, wherein the antigen from a pathogen comprises an antigen from a virus.

6. The method of claim 5, wherein the antigen from a virus comprises an antigen from human immunodeficiency virus (HIV), an antigen from influenza virus, or an antigen from respiratory syncytial virus (RSV).

7. The method of claim 6, wherein the antigen from HIV comprises HIV-1 Env.

8. The method of claim 6, wherein the antigen from influenza virus comprises hemagglutinin (HA).

9. The method of claim 6, wherein the antigen from RSV comprises an RSV F protein.

10. The method of claim 4, wherein the antigen from an animal comprises an antigen from a human.

11. The method of claim 10, wherein the antigen from a human comprises a vascular endothelial growth factor (VEGF) protein.

12. The method of claim 1, wherein the population of B-cells comprise a memory B-cell, a plasma cell, a naïve B cell, an activated B-cell, or a B-cell line.

13. The method of claim 12, wherein the B-cell line comprises VRC01, PGT128, PGT145, VRC34, 10E8, 447-52D, Fe53, or CH65.

14. The method of claim 1, wherein the plurality of antigens comprise a panel of epitope knock-outs.

15. The method of claim 1, wherein the plurality of antigens comprise a panel of antigen variants or mutations for epitope mapping.

* * * * *

SEQUENCE LISTING

<160> NUMBER OF SEQ ID NOS: 79

<210> SEQ ID NO 1
<211> LENGTH: 129
<212> TYPE: PRT
<213> ORGANISM: Artificial Sequence
<220> FEATURE:
<223> OTHER INFORMATION: Synthetic construct

<400> SEQUENCE: 1

```
Gln Phe Gln Leu Gln Glu Ser Gly Pro Gly Leu Val Lys Pro Ser Gln
1               5                   10                  15

Thr Leu Ser Leu Thr Cys Val Val Ser Gly Gly Ser Ile Gly Thr Thr
            20                  25                  30

Asp His Tyr Trp Gly Trp Ile Arg Gln Ser Pro Gly Lys Gly Leu Glu
        35                  40                  45

Trp Ile Gly Thr Thr Tyr Tyr Ser Gly Lys Thr Tyr Tyr Asn Pro Ser
    50                  55                  60

Leu Asn Ser Arg Val Thr Ile Ala Ile Asp Thr Ser Lys Asn Gln Phe
65                  70                  75                  80

Ser Leu Arg Leu Ile Ser Val Thr Ala Ala Asp Thr Ala Val Tyr His
                85                  90                  95

Cys Ala Arg His Arg Ala Asn Tyr Asp Phe Trp Gly Gly Ser Asn Leu
            100                 105                 110

Arg Gly Tyr Phe Asp Pro Trp Gly Arg Gly Thr Leu Val Thr Val Ser
        115                 120                 125

Ser
```

<210> SEQ ID NO 2
<211> LENGTH: 108
<212> TYPE: PRT
<213> ORGANISM: Artificial Sequence
<220> FEATURE:
<223> OTHER INFORMATION: Synthetic construct

<400> SEQUENCE: 2

```
Glu Ile Val Leu Thr Gln Ser Pro Gly Ile Leu Ser Leu Ser Pro Gly
1               5                   10                  15

Asp Ser Ala Ser Phe Ser Cys Arg Ala Ser Gln Arg Ile Ser Ser Tyr
            20                  25                  30

Asn Leu Ala Trp Tyr Gln Leu Lys Pro Asp Gln Ala Pro Arg Leu Leu
        35                  40                  45
```

```
Val His Gly Thr Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Gly Thr Ser Pro
                85                  90                  95

Thr Thr Phe Gly Pro Gly Thr Lys Val Asp Phe Arg
            100                 105


<210> SEQ ID NO 3
<211> LENGTH: 129
<212> TYPE: PRT
<213> ORGANISM: Artificial Sequence
<220> FEATURE:
<223> OTHER INFORMATION: Synthetic construct

<400> SEQUENCE: 3

Gln Phe Gln Leu Gln Glu Ser Gly Pro Gly Leu Val Lys Pro Ser Glu
1               5                   10                  15

Thr Leu Ser Leu Thr Cys Ile Val Ser Gly Gly Ser Ile Asp Thr Thr
            20                  25                  30

Asp His Tyr Trp Gly Trp Ile Arg Gln Ser Pro Gly Lys Gly Leu Glu
        35                  40                  45

Trp Ile Gly Thr Ser Tyr Tyr Ser Gly Lys Thr Tyr Tyr Asn Pro Ser
    50                  55                  60

Leu Ser Gly Arg Val Thr Ile Ser Ile Asp Thr Ser Lys Asn His Phe
65                  70                  75                  80

Ser Leu Arg Leu Ile Ser Val Thr Ala Ala Asp Thr Ala Val Tyr His
                85                  90                  95

Cys Ala Arg His Arg Ala Asp Tyr Asp Phe Trp Gly Gly Ser Asn Leu
            100                 105                 110

Arg Gly Tyr Phe Asp Pro Trp Gly Arg Gly Thr Leu Val Thr Val Ser
        115                 120                 125

Ser


<210> SEQ ID NO 4
<211> LENGTH: 108
<212> TYPE: PRT
<213> ORGANISM: Artificial Sequence
<220> FEATURE:
<223> OTHER INFORMATION: Synthetic construct

<400> SEQUENCE: 4

Glu Ile Val Leu Thr Gln Ser Pro Gly Ile Met Ser Leu Ser Pro Gly
1               5                   10                  15

Asp Ser Ala Ser Phe Ser Cys Arg Ala Ser Gln Arg Ile Ser Ser Tyr
            20                  25                  30

Asn Leu Ala Trp Tyr Gln His Lys Pro Asp Gln Ala Pro Arg Leu Leu
        35                  40                  45

Ile Tyr Gly Thr Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Gly Thr Ser Pro
                85                  90                  95

Thr Thr Phe Gly Pro Gly Thr Lys Val Asp Phe Arg
            100                 105
```

<210> SEQ ID NO 5
<211> LENGTH: 123
<212> TYPE: PRT
<213> ORGANISM: Artificial Sequence
<220> FEATURE:
<223> OTHER INFORMATION: Synthetic construct

<400> SEQUENCE: 5

```
Gln Val Gln Leu Gln Glu Ser Gly Pro Gly Leu Val Lys Pro Ser Glu
1               5                   10                  15

Thr Leu Ser Leu Thr Cys Ser Ile Ser Ser Arg Tyr Leu Thr Val Arg
            20                  25                  30

Ser Gly Thr Tyr Trp Ala Trp Val Arg Gln Ser Pro Gly Lys Gly Leu
        35                  40                  45

Glu Trp Ile Gly Ser Ile Ser Gln Ser Gly Thr Thr Tyr His Ser Pro
    50                  55                  60

Ser Leu Lys Asn Glu Ile Thr Ile Ser Leu Asp Thr Ser Asn Asn Gln
65                  70                  75                  80

Ile Phe Leu Lys Leu Thr Pro Val Thr Ala Ala Asp Thr Ala Phe Tyr
                85                  90                  95

Tyr Cys Ala Thr Arg Gly Ile Ala Ala Ser Gly Phe Tyr Phe Gln His
            100                 105                 110

Trp Gly Arg Gly Thr Leu Val Ser Ile Ser Ser
        115                 120
```

<210> SEQ ID NO 6
<211> LENGTH: 107
<212> TYPE: PRT
<213> ORGANISM: Artificial Sequence
<220> FEATURE:
<223> OTHER INFORMATION: Synthetic construct

<400> SEQUENCE: 6

```
Asp Ile Gln Met Thr Gln Ser Pro Ser Thr Leu Ser Ala Ser Val Gly
1               5                   10                  15

Asp Lys Val Thr Ile Thr Cys Arg Ala Ser Gln Ser Val Gly Ser Ser
            20                  25                  30

Leu Ala Trp Tyr Gln Gln Lys Pro Gly Arg Gly Pro Gln Leu Leu Ile
        35                  40                  45

Ser Lys Ala Ser Ile Ile Gln Ser Gly Val Pro Ser Arg Phe Ser Gly
    50                  55                  60

Gly Gly Ser Gly Thr Asp Phe Thr Leu Thr Ile Asn Asn Leu Gln Pro
65                  70                  75                  80

Asp Asp Leu Ala Thr Tyr Tyr Cys His His Tyr Asn Ser Phe Ser His
                85                  90                  95

Thr Phe Gly Gln Gly Thr Lys Val Glu Phe Lys
            100                 105
```

<210> SEQ ID NO 7
<211> LENGTH: 123
<212> TYPE: PRT
<213> ORGANISM: Artificial Sequence
<220> FEATURE:
<223> OTHER INFORMATION: Synthetic construct

<400> SEQUENCE: 7

```
Gln Val Gln Met Val Gln Ser Gly Ala Glu Met Lys Lys Pro Gly Ser
1               5                   10                  15
```

```
Ser Val Lys Val Ser Cys Lys Ala Ser Gly Ala Ser Trp Ser His Tyr
            20                  25                  30

Ala Val Asn Trp Val Arg Gln Ala Pro Gly Gln Gly Leu Glu Trp Met
        35                  40                  45

Gly Gly Val Ile Pro Ala Phe Asn Val Ile Asn Tyr Ala Gln Lys Phe
    50                  55                  60

Gln Gly Arg Val Thr Ile Ser Thr Asp Glu Ser Thr Thr Thr Val Phe
65                  70                  75                  80

Leu Glu Val Lys Ser Leu Lys Ser Asp Asp Thr Ala Asn Tyr Tyr Cys
                85                  90                  95

Val Gly Arg Gln Lys Tyr Ile Ser Gly Asn Val Gly Asp Phe Asp Phe
            100                 105                 110

Trp Gly Gln Gly Thr Met Ile Ile Val Ser Ser
        115                 120


<210> SEQ ID NO 8
<211> LENGTH: 109
<212> TYPE: PRT
<213> ORGANISM: Artificial Sequence
<220> FEATURE:
<223> OTHER INFORMATION: Synthetic construct

<400> SEQUENCE: 8

Asp Ile Gln Met Thr Gln Ser Pro Ser Ser Leu Ser Leu Ser Ile Gly
1               5                   10                  15

Glu Arg Val Thr Ile Thr Cys Gln Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Ser Ser Arg Phe Ser Gly
    50                  55                  60

Ser Gly Ser Gly Thr His Phe Thr Phe Thr Ile Ser Asn Leu Gln Ala
65                  70                  75                  80

Glu Asp Ala Gly Thr Tyr Tyr Cys Gln Gln Tyr Thr Asn Leu Pro Pro
                85                  90                  95

Ala Leu Asn Phe Gly Gly Gly Thr Lys Val Glu Ile Arg
            100                 105


<210> SEQ ID NO 9
<211> LENGTH: 133
<212> TYPE: PRT
<213> ORGANISM: Artificial Sequence
<220> FEATURE:
<223> OTHER INFORMATION: Synthetic construct

<400> SEQUENCE: 9

Glu Ala Gln Leu Leu Glu Ser Gly Gly Gly Leu Val Gln Pro Gly Gly
1               5                   10                  15

Ser Leu Arg Leu Ser Cys Glu Ala Ser Gly Phe Ser Phe Asn Met Tyr
            20                  25                  30

Gly Met Ser Trp Val Arg Gln Gly Pro Gly Lys Gly Leu Glu Trp Val
        35                  40                  45

Ala Phe Val Ser Gly Asn Ser Asp Lys Arg Asp Tyr Glu Asp Ser Val
    50                  55                  60

Lys Gly Arg Phe Thr Ile Ser Arg Asp Asn Ser Asn Lys Arg Leu Tyr
65                  70                  75                  80

Leu Gln Met Asn Gly Leu Arg Gly Glu Asp Thr Ala Thr Tyr Phe Cys
                85                  90                  95
```

```
Ala Arg Asp Glu Val Leu Arg Gly Ser Ala Ser Trp Phe Leu Gly Pro
            100                 105                 110

Asn Glu Val Arg His Tyr Gly Met Asp Val Trp Gly Arg Gly Thr Thr
        115                 120                 125

Val Val Val Ser Ser
    130


<210> SEQ ID NO 10
<211> LENGTH: 112
<212> TYPE: PRT
<213> ORGANISM: Artificial Sequence
<220> FEATURE:
<223> OTHER INFORMATION: Synthetic construct

<400> SEQUENCE: 10

Asp Ile Val Leu Thr Gln Thr Pro Pro Ser Leu Ser Val Ile Pro Gly
1               5                   10                  15

Gln Ser Ala Ser Ile Ser Cys Arg Ser Ser Gln Ser Leu Leu Asn Ser
            20                  25                  30

Asp Gln Gln Arg Thr Tyr Leu Ser Trp Phe Leu Gln Lys Pro Gly Gln
        35                  40                  45

Ser Pro Gln Leu Leu Ile Phe Asp Val Ser Ser Arg Phe Ser Gly Val
    50                  55                  60

Pro Asp Arg Phe Ser Gly Ser Gly Ala Gly Arg Asp Phe Thr Leu Lys
65                  70                  75                  80

Ile Ser Arg Val Glu Ala Gly Asp Ala Gly Ile Tyr Tyr Cys Met Gln
                85                  90                  95

Ser Leu Gln Leu Arg Ser Phe Gly Gln Gly Thr Lys Leu Glu Ile Arg
            100                 105                 110


<210> SEQ ID NO 11
<211> LENGTH: 116
<212> TYPE: PRT
<213> ORGANISM: Artificial Sequence
<220> FEATURE:
<223> OTHER INFORMATION: Synthetic construct

<400> SEQUENCE: 11

Gln Val Leu Leu Val Gln Ser Gly Ala Glu Val Lys Lys Pro Gly Ala
1               5                   10                  15

Ser Val Lys Val Ser Cys Lys Thr Ser Gly Tyr Thr Phe Asn Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Arg Gly Glu Thr Lys Tyr Ala Gln Asn Phe
    50                  55                  60

Gln Gly Arg Leu Thr Met Thr Thr Asp Thr Ser Thr Asn Thr Ala Tyr
65                  70                  75                  80

Met Glu Leu Arg Thr Leu Thr Ser Asp Asp Thr Ala Val Phe Tyr Cys
                85                  90                  95

Ala Arg Gly Arg Val Tyr Ser Asp Tyr Trp Gly Gln Gly Thr Pro Val
            100                 105                 110

Thr Val Ser Ser
        115


<210> SEQ ID NO 12
<211> LENGTH: 109
<212> TYPE: PRT
```

<213> ORGANISM: Artificial Sequence
<220> FEATURE:
<223> OTHER INFORMATION: Synthetic construct

<400> SEQUENCE: 12

```
Glu Ile Val Leu Thr Gln Ser Pro Gly Thr Leu Ser Leu Ser Pro Gly
1               5                   10                  15

Glu Arg Ala Thr Leu Ser Cys Arg Ala Gly Gln Ser Ile Asn Ile Gly
            20                  25                  30

Tyr Leu Ala Trp Tyr Gln Gln Lys Pro Gly Gln Pro Pro Arg Leu Leu
        35                  40                  45

Ile Tyr Ala Thr Ser Asn Arg Ala Thr Asp Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Gly Thr Ser Pro
                85                  90                  95

Pro Trp Thr Phe Gly Gln Gly Thr Lys Val Glu Ile Lys
            100                 105
```

<210> SEQ ID NO 13
<211> LENGTH: 126
<212> TYPE: PRT
<213> ORGANISM: Artificial Sequence
<220> FEATURE:
<223> OTHER INFORMATION: Synthetic construct

<400> SEQUENCE: 13

```
Gln Val Gln Leu Leu Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Ser Tyr Tyr Trp Thr Trp Ile Arg Gln Ser Ala Gly Lys Gly Leu Glu
        35                  40                  45

Trp Ile Gly Asn Ile Phe Pro Thr Gly Arg Thr Asn Tyr Ser Pro Ser
    50                  55                  60

Phe Lys Ser Arg Val Phe Ile Ser Arg Asp Thr Ser Lys Asn Gln Phe
65                  70                  75                  80

Ser Leu Thr Leu Thr Ser Met Thr Val Ala Asp Thr Ala Val Tyr His
                85                  90                  95

Cys Ala Arg Glu His Thr Met Ile Phe Gly Val Ala Glu Gly Phe Trp
            100                 105                 110

Phe Asp Pro Trp Gly Gln Gly Thr Leu Val Thr Val Ser Ser
        115                 120                 125
```

<210> SEQ ID NO 14
<211> LENGTH: 108
<212> TYPE: PRT
<213> ORGANISM: Artificial Sequence
<220> FEATURE:
<223> OTHER INFORMATION: Synthetic construct

<400> SEQUENCE: 14

```
Pro Ser Lys Leu Thr Gln Asp Pro Val Met Ser Val Ala Leu Gly Gln
1               5                   10                  15

Thr Val Lys Ile Thr Cys Arg Gly Asp Ser Leu Arg Thr Tyr Tyr Ala
            20                  25                  30

Ser Trp Tyr Gln Gln Lys Pro Gly Gln Ala Pro Leu Leu Leu Ile Tyr
        35                  40                  45
```

```
Gly Lys Asn Ser Arg Pro Ser Gly Ile Ser Gly Arg Phe Ser Gly Ser
    50                  55                  60

Thr Ser Gly Asn Pro Ala Ser Leu Thr Ile Thr Gly Ala Gln Ala Glu
65                  70                  75                  80

Asp Glu Ala Asp Tyr Tyr Cys Ser Ser Arg Asp Thr Asp Asp Ile Ser
                85                  90                  95

Val Ile Phe Gly Gly Gly Thr Lys Leu Thr Val Leu
            100                 105


<210> SEQ ID NO 15
<211> LENGTH: 122
<212> TYPE: PRT
<213> ORGANISM: Artificial Sequence
<220> FEATURE:
<223> OTHER INFORMATION: Synthetic construct

<400> SEQUENCE: 15

Gln Val Gln Val Val Gln Ser Gly Ala Glu Val Lys Lys Pro Gly Ser
1               5                   10                  15

Ser Val Arg Val Ser Cys Lys Ala Ser Gly Gly Leu Phe Arg Ser His
            20                  25                  30

Ala Val Ser Trp Val Arg Gln Ala Pro Gly Gln Gly Leu Glu Trp Met
        35                  40                  45

Gly Gly Ile Val Ala Leu Phe Gly Thr Thr Asn Tyr Ala Gln Lys Phe
    50                  55                  60

Gln Asp Arg Val Thr Ile Thr Ala Asp Glu Ser Thr Asn Thr Val Tyr
65                  70                  75                  80

Leu Glu Leu Asn Ser Leu Arg Ser Asp Asp Thr Ala Met Tyr Tyr Cys
                85                  90                  95

Val Thr Met Ser Gly Tyr His Val Ser Asn Thr Tyr Leu Asp Ala Trp
            100                 105                 110

Gly Gln Gly Thr Leu Val Thr Val Ser Ser
        115                 120


<210> SEQ ID NO 16
<211> LENGTH: 108
<212> TYPE: PRT
<213> ORGANISM: Artificial Sequence
<220> FEATURE:
<223> OTHER INFORMATION: Synthetic construct

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ala Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Ala Asn Ser Pro
                85                  90                  95

Leu Thr Phe Gly Gly Gly Thr Lys Val Asp Ile Lys
            100                 105
```

```
<210> SEQ ID NO 17
<211> LENGTH: 129
<212> TYPE: PRT
<213> ORGANISM: Artificial Sequence
<220> FEATURE:
<223> OTHER INFORMATION: Synthetic construct

<400> SEQUENCE: 17

Gln Val Gln Leu Gln Glu Ser Gly Pro Gly Leu Leu Lys Thr Ser Glu
1               5                   10                  15

Thr Leu Ser Leu Ser Cys Val Val Ser Gly Val Ser Val Ser Ser Ser
            20                  25                  30

Asn His Tyr Trp Gly Trp Val Arg Gln Thr Pro Gly Arg Gly Leu Glu
        35                  40                  45

Trp Ile Ala Thr Val Tyr Ser Ser Gly Lys Thr Tyr Phe Asn Pro Ser
    50                  55                  60

Leu Lys Ser Arg Val Ile Ile Ser Val Asp Thr Ser Asn Asn Gln Phe
65                  70                  75                  80

Ser Leu Lys Met Thr Ser Leu Thr Val Ala Asp Thr Ala Val Tyr Tyr
                85                  90                  95

Cys Ala Arg His Arg Ala Asp Tyr Asp Phe Trp Asn Gly Asn Asn Leu
            100                 105                 110

Arg Gly Tyr Phe Asp Pro Trp Gly Gln Gly Ala Leu Val Thr Val Ser
        115                 120                 125

Ser


<210> SEQ ID NO 18
<211> LENGTH: 108
<212> TYPE: PRT
<213> ORGANISM: Artificial Sequence
<220> FEATURE:
<223> OTHER INFORMATION: Synthetic construct

<400> SEQUENCE: 18

Glu Ile Val Leu Thr Gln Ser Pro Gly Thr Leu Ser Val Ser Pro Gly
1               5                   10                  15

Glu Arg Ala Thr Leu Ser Cys Arg Pro Ser Gln Thr Phe Thr Asn Thr
            20                  25                  30

Asn Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60

Gly Ser Arg Ser Gly Thr Asp Phe Thr Leu Thr Ile Ser Arg Leu Glu
65                  70                  75                  80

Pro Glu Asp Phe Ala Ile Tyr Tyr Cys Gln Gln Tyr Gly Ser Ser Pro
                85                  90                  95

Thr Thr Phe Gly Pro Gly Thr Lys Val Asp Met Lys
            100                 105


<210> SEQ ID NO 19
<211> LENGTH: 125
<212> TYPE: PRT
<213> ORGANISM: Artificial Sequence
<220> FEATURE:
<223> OTHER INFORMATION: Synthetic construct

<400> SEQUENCE: 19

Ser Gln Ala Leu Val Gln Ser Gly Ser Gln Met Lys Lys Pro Gly Asp
1               5                   10                  15
```

```
Ser Val Arg Leu Ser Cys Gln Thr Ser Asp Ser Ala Ile Thr Lys Tyr
            20                  25                  30

Phe Ile His Trp Ile Arg Gln Ala Pro Gly Lys Gly Leu Glu Trp Ile
        35                  40                  45

Ala Trp Ile Ser Pro Tyr Gly Gly Gly Val Asn Tyr Gly Trp Gln Val
    50                  55                  60

Arg Asp Arg Ala Thr Leu Thr Arg Asn Ile His Met Glu Thr Ile Tyr
65                  70                  75                  80

Phe Asp Leu Arg Gly Leu Arg Pro Asp Asp Thr Ala Thr Tyr Tyr Cys
                85                  90                  95

Ala Met Arg Asp Tyr Cys Arg Asp Asp Ser Cys Asn Ile Trp Asp Leu
            100                 105                 110

Arg His Trp Gly Gln Gly Ser Leu Ile Val Val Ser Ala
        115                 120                 125


<210> SEQ ID NO 20
<211> LENGTH: 103
<212> TYPE: PRT
<213> ORGANISM: Artificial Sequence
<220> FEATURE:
<223> OTHER INFORMATION: Synthetic construct

<400> SEQUENCE: 20

Ala Val Met Leu Thr Gln Ser Pro Gly Thr Leu Ser Leu Ser Pro Gly
1               5                   10                  15

Asp Arg Ser Thr Leu Leu Cys Arg Ala Ser Gln Gly Ile Gly Asn Glu
            20                  25                  30

Leu Ala Trp Tyr Gln Gln Lys Arg Gly Gln Thr Pro Arg Leu Ile Val
        35                  40                  45

Tyr Gly Ala Ser Gln Arg Ala Pro Gly Val Pro Asp Arg Phe Gly Gly
    50                  55                  60

Ser Val Ser Gly Ser Asp Phe Thr Leu Ile Ile Asn Arg Leu Glu Thr
65                  70                  75                  80

Glu Asp Phe Ala Phe Tyr Phe Cys Gln His Arg Glu Thr Phe Gly Pro
                85                  90                  95

Gly Thr Lys Leu Asp Leu Lys
            100


<210> SEQ ID NO 21
<211> LENGTH: 18
<212> TYPE: PRT
<213> ORGANISM: Artificial Sequence
<220> FEATURE:
<223> OTHER INFORMATION: Synthetic construct

<400> SEQUENCE: 21

Ala Met Arg Asp Tyr Cys Arg Asp Asp Asn Cys Asn Lys Trp Asp Leu
1               5                   10                  15

Arg His


<210> SEQ ID NO 22
<211> LENGTH: 18
<212> TYPE: PRT
<213> ORGANISM: Artificial Sequence
<220> FEATURE:
<223> OTHER INFORMATION: Synthetic construct

<400> SEQUENCE: 22

Ala Met Arg Asp Tyr Cys Arg Asp Asp Asn Cys Asn Arg Trp Asp Leu
1               5                   10                  15
```

Arg His

<210> SEQ ID NO 23
<211> LENGTH: 18
<212> TYPE: PRT
<213> ORGANISM: Artificial Sequence
<220> FEATURE:
<223> OTHER INFORMATION: Synthetic construct

<400> SEQUENCE: 23

Ala Met Arg Asp Tyr Cys Arg Asp Asp Ser Cys Asn Ile Trp Asp Leu
1 5 10 15

Arg His

<210> SEQ ID NO 24
<211> LENGTH: 18
<212> TYPE: PRT
<213> ORGANISM: Artificial Sequence
<220> FEATURE:
<223> OTHER INFORMATION: Synthetic construct

<400> SEQUENCE: 24

Ala Met Arg Asp Tyr Cys Arg Asp Asp Asn Cys Asn Ile Trp Asp Leu
1 5 10 15

Arg His

<210> SEQ ID NO 25
<211> LENGTH: 18
<212> TYPE: PRT
<213> ORGANISM: Artificial Sequence
<220> FEATURE:
<223> OTHER INFORMATION: Synthetic construct

<400> SEQUENCE: 25

Val Arg Thr Ala Tyr Cys Glu Arg Asp Pro Cys Lys Gly Trp Val Phe
1 5 10 15

Pro His

<210> SEQ ID NO 26
<211> LENGTH: 16
<212> TYPE: PRT
<213> ORGANISM: Artificial Sequence
<220> FEATURE:
<223> OTHER INFORMATION: Synthetic construct

<400> SEQUENCE: 26

Val Arg Arg Gly His Cys Asp His Cys Tyr Glu Trp Thr Leu Gln His
1 5 10 15

<210> SEQ ID NO 27
<211> LENGTH: 16
<212> TYPE: PRT
<213> ORGANISM: Artificial Sequence
<220> FEATURE:
<223> OTHER INFORMATION: Synthetic construct

<400> SEQUENCE: 27

Val Arg Arg Gly Ser Cys Asp Tyr Cys Gly Asp Phe Pro Trp Gln Tyr
1 5 10 15

<210> SEQ ID NO 28
<211> LENGTH: 16
<212> TYPE: PRT
<213> ORGANISM: Artificial Sequence
<220> FEATURE:
<223> OTHER INFORMATION: Synthetic construct

<400> SEQUENCE: 28

Val Arg Arg Gly Ser Cys Gly Tyr Cys Gly Asp Phe Pro Trp Gln Tyr
1 5 10 15

<210> SEQ ID NO 29
<211> LENGTH: 25
<212> TYPE: PRT
<213> ORGANISM: Artificial Sequence
<220> FEATURE:
<223> OTHER INFORMATION: Synthetic construct

<400> SEQUENCE: 29

Val Arg Gly Ser Ser Cys Cys Gly Gly Arg Arg His Cys Asn Gly Ala
1 5 10 15

Asp Cys Phe Asn Trp Asp Phe Gln Tyr
20 25

<210> SEQ ID NO 30
<211> LENGTH: 25
<212> TYPE: PRT
<213> ORGANISM: Artificial Sequence
<220> FEATURE:
<223> OTHER INFORMATION: Synthetic construct

<400> SEQUENCE: 30

Val Arg Gly Arg Ser Cys Cys Gly Gly Arg Arg His Cys Asn Gly Ala
1 5 10 15

Asp Cys Phe Asn Trp Asp Phe Gln Tyr
20 25

<210> SEQ ID NO 31
<211> LENGTH: 25
<212> TYPE: PRT
<213> ORGANISM: Artificial Sequence
<220> FEATURE:
<223> OTHER INFORMATION: Synthetic construct

<400> SEQUENCE: 31

Val Arg Gly Lys Ser Cys Cys Gly Gly Arg Arg Tyr Cys Asn Gly Ala
1 5 10 15

Asp Cys Phe Asn Trp Asp Phe Glu His
20 25

<210> SEQ ID NO 32
<211> LENGTH: 25
<212> TYPE: PRT
<213> ORGANISM: Artificial Sequence
<220> FEATURE:
<223> OTHER INFORMATION: Synthetic construct

<400> SEQUENCE: 32

Val Arg Gly Lys Ser Cys Cys His Gly Arg Arg Tyr Cys Asn Gly Ala
1 5 10 15

Asp Cys Phe Asn Trp Asp Phe Glu His
20 25

<210> SEQ ID NO 33
<211> LENGTH: 25
<212> TYPE: PRT
<213> ORGANISM: Artificial Sequence
<220> FEATURE:
<223> OTHER INFORMATION: Synthetic construct

```
<400> SEQUENCE: 33

Val Arg Gly Arg Ser Cys Cys Asp Gly Arg Arg Tyr Cys Asn Gly Ala
1               5                   10                  15

Asp Cys Phe Asn Trp Asp Phe Glu His
            20                  25


<210> SEQ ID NO 34
<211> LENGTH: 18
<212> TYPE: PRT
<213> ORGANISM: Artificial Sequence
<220> FEATURE:
<223> OTHER INFORMATION: Synthetic construct

<400> SEQUENCE: 34

Thr Arg Gly Lys Tyr Cys Thr Ala Arg Asp Tyr Tyr Asn Trp Asp Phe
1               5                   10                  15

Glu His


<210> SEQ ID NO 35
<211> LENGTH: 18
<212> TYPE: PRT
<213> ORGANISM: Artificial Sequence
<220> FEATURE:
<223> OTHER INFORMATION: Synthetic construct

<400> SEQUENCE: 35

Thr Arg Gly Lys Tyr Cys Thr Ala Arg Asp Tyr Tyr Asn Trp Asp Phe
1               5                   10                  15

Glu Tyr


<210> SEQ ID NO 36
<211> LENGTH: 14
<212> TYPE: PRT
<213> ORGANISM: Artificial Sequence
<220> FEATURE:
<223> OTHER INFORMATION: Synthetic construct

<400> SEQUENCE: 36

Thr Arg Gly Lys Asn Cys Asp Asp Asn Trp Asp Phe Glu His
1               5                   10


<210> SEQ ID NO 37
<211> LENGTH: 14
<212> TYPE: PRT
<213> ORGANISM: Artificial Sequence
<220> FEATURE:
<223> OTHER INFORMATION: Synthetic construct

<400> SEQUENCE: 37

Thr Arg Gly Lys Asn Cys Asn Tyr Asn Trp Asp Phe Glu His
1               5                   10


<210> SEQ ID NO 38
<211> LENGTH: 21
<212> TYPE: PRT
<213> ORGANISM: Artificial Sequence
<220> FEATURE:
<223> OTHER INFORMATION: Synthetic construct

<400> SEQUENCE: 38

Ala Arg His Arg Ala Asp Tyr Asp Phe Trp Asn Gly Asn Asn Leu Arg
1               5                   10                  15

Gly Tyr Phe Asp Pro
```

20

<210> SEQ ID NO 39
<211> LENGTH: 21
<212> TYPE: PRT
<213> ORGANISM: Artificial Sequence
<220> FEATURE:
<223> OTHER INFORMATION: Synthetic construct

<400> SEQUENCE: 39

Ala Arg His Arg Ala Asp Tyr Asp Phe Trp Gly Gly Ser Asn Leu Arg
1 5 10 15

Gly Tyr Phe Asp Pro
20

<210> SEQ ID NO 40
<211> LENGTH: 21
<212> TYPE: PRT
<213> ORGANISM: Artificial Sequence
<220> FEATURE:
<223> OTHER INFORMATION: Synthetic construct

<400> SEQUENCE: 40

Ala Arg His Arg Ala Asn Tyr Asp Phe Trp Gly Gly Ser Asn Leu Arg
1 5 10 15

Gly Tyr Phe Asp Pro
20

<210> SEQ ID NO 41
<211> LENGTH: 15
<212> TYPE: PRT
<213> ORGANISM: Artificial Sequence
<220> FEATURE:
<223> OTHER INFORMATION: Synthetic construct

<400> SEQUENCE: 41

Val Thr Met Ser Gly Tyr His Val Ser Asn Thr Tyr Leu Asp Ala
1 5 10 15

<210> SEQ ID NO 42
<211> LENGTH: 9
<212> TYPE: PRT
<213> ORGANISM: Artificial Sequence
<220> FEATURE:
<223> OTHER INFORMATION: Synthetic construct

<400> SEQUENCE: 42

Ala Arg Gly Arg Val Tyr Ser Asp Tyr
1 5

<210> SEQ ID NO 43
<211> LENGTH: 21
<212> TYPE: PRT
<213> ORGANISM: Artificial Sequence
<220> FEATURE:
<223> OTHER INFORMATION: Synthetic construct

<400> SEQUENCE: 43

Ala Arg His Arg Ala Asp Phe Asp Phe Trp Asn Arg Gly Asn Leu Arg
1 5 10 15

Gly Tyr Phe Asp Pro
20

<210> SEQ ID NO 44
<211> LENGTH: 21

<212> TYPE: PRT
<213> ORGANISM: Artificial Sequence
<220> FEATURE:
<223> OTHER INFORMATION: Synthetic construct

<400> SEQUENCE: 44

```
Ala Arg His Arg Ala Asp Tyr Asp Phe Trp Asn Gly Asn Asn Leu Arg
1               5                   10                  15

Gly Tyr Phe Asp Pro
            20
```

<210> SEQ ID NO 45
<211> LENGTH: 21
<212> TYPE: PRT
<213> ORGANISM: Artificial Sequence
<220> FEATURE:
<223> OTHER INFORMATION: Synthetic construct

<400> SEQUENCE: 45

```
Ala Arg His Arg Ala Gly Tyr Asp Phe Trp Ser Gly Ser Asn Leu Arg
1               5                   10                  15

Gly Tyr Phe Asp Pro
            20
```

<210> SEQ ID NO 46
<211> LENGTH: 21
<212> TYPE: PRT
<213> ORGANISM: Artificial Sequence
<220> FEATURE:
<223> OTHER INFORMATION: Synthetic construct

<400> SEQUENCE: 46

```
Ala Arg His Arg Ala Asn Tyr Asp Phe Trp Gly Gly Ser Asn Leu Arg
1               5                   10                  15

Gly Tyr Phe Asp Pro
            20
```

<210> SEQ ID NO 47
<211> LENGTH: 21
<212> TYPE: PRT
<213> ORGANISM: Artificial Sequence
<220> FEATURE:
<223> OTHER INFORMATION: Synthetic construct

<400> SEQUENCE: 47

```
Ala Arg His Arg Ala Asp Tyr Asp Phe Trp Gly Gly Ser Asn Leu Arg
1               5                   10                  15

Gly Tyr Phe Asp Pro
            20
```

<210> SEQ ID NO 48
<211> LENGTH: 47
<212> TYPE: DNA
<213> ORGANISM: Artificial Sequence
<220> FEATURE:
<223> OTHER INFORMATION: Synthetic construct; N's represent the antigen barcode
<220> FEATURE:
<221> NAME/KEY: misc_feature
<222> LOCATION: (22)..(34)
<223> OTHER INFORMATION: n is a, c, g, or t

<400> SEQUENCE: 48

```
ccttggcacc cgagaattcc annnnnnnnn nnnncccata taagaaa                47
```

<210> SEQ ID NO 49
<211> LENGTH: 13
<212> TYPE: DNA
<213> ORGANISM: Artificial Sequence
<220> FEATURE:
<223> OTHER INFORMATION: Synthetic construct

<400> SEQUENCE: 49
catgattggc tca 13

<210> SEQ ID NO 50
<211> LENGTH: 13
<212> TYPE: DNA
<213> ORGANISM: Artificial Sequence
<220> FEATURE:
<223> OTHER INFORMATION: Synthetic construct

<400> SEQUENCE: 50
tgtccggcaa taa 13

<210> SEQ ID NO 51
<211> LENGTH: 5
<212> TYPE: PRT
<213> ORGANISM: Artificial Sequence
<220> FEATURE:
<223> OTHER INFORMATION: Synthetic construct

<400> SEQUENCE: 51

Gln His Arg Glu Thr
1 5

<210> SEQ ID NO 52
<211> LENGTH: 5
<212> TYPE: PRT
<213> ORGANISM: Artificial Sequence
<220> FEATURE:
<223> OTHER INFORMATION: Synthetic construct

<400> SEQUENCE: 52

Gln His Arg Glu Thr
1 5

<210> SEQ ID NO 53
<211> LENGTH: 5
<212> TYPE: PRT
<213> ORGANISM: Artificial Sequence
<220> FEATURE:
<223> OTHER INFORMATION: Synthetic construct

<400> SEQUENCE: 53

Gln His Arg Glu Thr
1 5

<210> SEQ ID NO 54
<211> LENGTH: 5
<212> TYPE: PRT
<213> ORGANISM: Artificial Sequence
<220> FEATURE:
<223> OTHER INFORMATION: Synthetic construct

<400> SEQUENCE: 54

Gln His Arg Glu Thr
1 5

<210> SEQ ID NO 55
<211> LENGTH: 5
<212> TYPE: PRT

<213> ORGANISM: Artificial Sequence
<220> FEATURE:
<223> OTHER INFORMATION: Synthetic construct

<400> SEQUENCE: 55

Gln Phe Leu Glu Asn
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic construct

<400> SEQUENCE: 56

Gln Asp Arg Gln Ser
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic construct

<400> SEQUENCE: 57

Gln Gln Phe Glu Phe
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic construct

<400> SEQUENCE: 58

Gln Gln Phe Glu Phe
1               5

<210> SEQ ID NO 59
<211> LENGTH: 5
<212> TYPE: PRT
<213> ORGANISM: Artificial Sequence
<220> FEATURE:
<223> OTHER INFORMATION: Synthetic construct

<400> SEQUENCE: 59

Gln Cys Leu Glu Ala
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic construct

<400> SEQUENCE: 60

Gln Cys Leu Glu Ala
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic construct

<400> SEQUENCE: 61

Gln Ser Phe Glu Gly
1 5

<210> SEQ ID NO 62
<211> LENGTH: 5
<212> TYPE: PRT
<213> ORGANISM: Artificial Sequence
<220> FEATURE:
<223> OTHER INFORMATION: Synthetic construct

<400> SEQUENCE: 62

Gln Cys Met Glu Gly
1 5

<210> SEQ ID NO 63
<211> LENGTH: 5
<212> TYPE: PRT
<213> ORGANISM: Artificial Sequence
<220> FEATURE:
<223> OTHER INFORMATION: Synthetic construct

<400> SEQUENCE: 63

Gln Cys Phe Glu Gly
1 5

<210> SEQ ID NO 64
<211> LENGTH: 5
<212> TYPE: PRT
<213> ORGANISM: Artificial Sequence
<220> FEATURE:
<223> OTHER INFORMATION: Synthetic construct

<400> SEQUENCE: 64

Gln Gln Tyr Glu Phe
1 5

<210> SEQ ID NO 65
<211> LENGTH: 5
<212> TYPE: PRT
<213> ORGANISM: Artificial Sequence
<220> FEATURE:
<223> OTHER INFORMATION: Synthetic construct

<400> SEQUENCE: 65

Gln Gln Tyr Glu Phe
1 5

<210> SEQ ID NO 66
<211> LENGTH: 5
<212> TYPE: PRT
<213> ORGANISM: Artificial Sequence
<220> FEATURE:
<223> OTHER INFORMATION: Synthetic construct

<400> SEQUENCE: 66

Gln Gln Tyr Glu Phe
1 5

<210> SEQ ID NO 67
<211> LENGTH: 5
<212> TYPE: PRT
<213> ORGANISM: Artificial Sequence
<220> FEATURE:

<223> OTHER INFORMATION: Synthetic construct

<400> SEQUENCE: 67

Gln Gln Tyr Glu Phe
1 5

<210> SEQ ID NO 68
<211> LENGTH: 9
<212> TYPE: PRT
<213> ORGANISM: Artificial Sequence
<220> FEATURE:
<223> OTHER INFORMATION: Synthetic construct

<400> SEQUENCE: 68

Gln Gln Tyr Gly Ser Ser Pro Thr Thr
1 5

<210> SEQ ID NO 69
<211> LENGTH: 9
<212> TYPE: PRT
<213> ORGANISM: Artificial Sequence
<220> FEATURE:
<223> OTHER INFORMATION: Synthetic construct

<400> SEQUENCE: 69

Gln Gln Tyr Gly Thr Ser Pro Thr Thr
1 5

<210> SEQ ID NO 70
<211> LENGTH: 9
<212> TYPE: PRT
<213> ORGANISM: Artificial Sequence
<220> FEATURE:
<223> OTHER INFORMATION: Synthetic construct

<400> SEQUENCE: 70

Gln Gln Tyr Gly Thr Ser Pro Thr Thr
1 5

<210> SEQ ID NO 71
<211> LENGTH: 9
<212> TYPE: PRT
<213> ORGANISM: Artificial Sequence
<220> FEATURE:
<223> OTHER INFORMATION: Synthetic construct

<400> SEQUENCE: 71

Gln Gln Tyr Ala Asn Ser Pro Leu Thr
1 5

<210> SEQ ID NO 72
<211> LENGTH: 10
<212> TYPE: PRT
<213> ORGANISM: Artificial Sequence
<220> FEATURE:
<223> OTHER INFORMATION: Synthetic construct

<400> SEQUENCE: 72

Gln Gln Ser Gly Thr Ser Pro Pro Trp Thr
1 5 10

<210> SEQ ID NO 73
<211> LENGTH: 9
<212> TYPE: PRT
<213> ORGANISM: Artificial Sequence
<220> FEATURE:
<223> OTHER INFORMATION: Synthetic construct

<400> SEQUENCE: 73

Gln Gln Tyr Gly Thr Ser Pro Thr Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic construct

<400> SEQUENCE: 74

Gln Gln Tyr Gly Ser Ser Pro Thr Thr
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic construct

<400> SEQUENCE: 75

Gln Gln Tyr Gly Ser Ser Pro Ala Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic construct

<400> SEQUENCE: 76

Gln Gln Tyr Gly Thr Ser Pro Thr Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic construct

<400> SEQUENCE: 77

Gln Gln Tyr Gly Thr Ser Pro Thr Thr
1               5

<210> SEQ ID NO 78
<211> LENGTH: 13
<212> TYPE: DNA
<213> ORGANISM: Artificial Sequence
<220> FEATURE:
<223> OTHER INFORMATION: Synthetic construct

<400> SEQUENCE: 78
gatcgtaata cca                                                        13

<210> SEQ ID NO 79
<211> LENGTH: 20
<212> TYPE: DNA
<213> ORGANISM: Artificial Sequence
<220> FEATURE:
<223> OTHER INFORMATION: Synthetic construct

<400> SEQUENCE: 79
ccttggcacc cgagaattcc 20